(12) United States Patent
Raftery et al.

(10) Patent No.: US 8,653,006 B2
(45) Date of Patent: Feb. 18, 2014

(54) METABOLITE BIOMARKERS FOR THE DETECTION OF ESOPHAGEAL CANCER USING NMR

(75) Inventors: M. Daniel Raftery, West Lafayette, IN (US); Jian Zhang, West Lafayette, IN (US); Zane Hammoud, Northville, MI (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/226,256

(22) Filed: Sep. 6, 2011

(65) Prior Publication Data

US 2012/0142542 A1 Jun. 7, 2012

Related U.S. Application Data

(60) Provisional application No. 61/402,729, filed on Sep. 3, 2010, provisional application No. 61/403,910, filed on Sep. 23, 2010.

(51) Int. Cl.
  *C40B 30/00* (2006.01)
  *C40B 40/12* (2006.01)
  *C40B 40/04* (2006.01)

(52) U.S. Cl.
  USPC .............................................. 506/7; 436/64

(58) Field of Classification Search
  None
  See application file for complete search history.

(56) References Cited

FOREIGN PATENT DOCUMENTS

| WO | WO 2011/046597 | 4/2011 |
|---|---|---|
| WO | WO 2011/119772 | 9/2011 |

OTHER PUBLICATIONS

Gagajewski et al., "Measurement of Chemical Analytes in Vitreous Humor: Stability and Precision Studies" Journal of Forensic Science, vol. 49, No. 2, Mar. 2004.*
Solga, et al., "Breath biomarkers and non-alcoholic fatty liver disease: Preliminary observations" Biomarkers, 11(2): pp. 174-183, Mar.-Apr. 2006.*
Meky et al., "Development of a urinary biomarker of human exposure to deoxynivalenol", Food and Chemical Toxicology, vol. 41, p. 265-273 (2003).*
Wu et al., "Metabolomic study for diagnostic model of oesophageal cancer using gas chromatography/mass spectrometry", Journal of Chromatography B, p. 3111-3117 (Aug. 7, 2009).*
Zhang et al., "Moving cancer diagnostics from bench to bedside", TRENDS in Biotechnology, vol. 25, No. 4, p. 166-173 (2007).*
Bird-Lieberman, E.L., et al., "Early Diagnosis of cesophageal cancer," British Journal of Cancer, 2009, 101, 1-6.
Carrola, J. et al., "Metabolic signatures of lung cancer in biofluids: NMR-based metabonomics of urine," J Proteome Res. Jan. 7, 2011; 10(1):221-30.
Cho, S.-H., et al., Evaluation of urinary nucleosides in breast cancer patients before and after tumor removal. Clinical Biochemistry 42 (2009) 540-543.
Djukovic, D. et al., "Targeted serum metaboilite of nucleosides in asophageal adenocarcinoma," Rapid Commun. Mass Spectrom, Oct. 30, 2010; 24(20): 3057-62. Abstract.
Duffy, M. and Crown, J., "A personalized approach to cancer treatment: how biomarkers can help." Clinical Chemistry, 2008, 54:11, 1770-79.
Enzinger, P, et al., Esophageal Cancer, N. Engl. J. Med. 349:23, Dec. 4, 2003.
Fukui, Y. and Itoh, K., A plasma metabolomics investigation of colorectal cancer patients by liquid chromatography-mass spectrometry, Open Analystical Chemistry J. 2010, 4, 1-9.
Henneges, C, et al., Prediction of breast cancer by profiling urinary RNA metabolites using Support Vector Machine-based feature selection, BMC Cancer, 2009, 9:104.
Jordan, K.W. et al. "Comparison of squamous cell carcinoma and adenocarcinoma," Lung Cancer, Apr. 2010; 68(1):44-50.
Lynch, J, et al., Novel Diagnostic Test for Acute Stroke, Stroke, 2004, 35:57-63.
Psychogios, N. et al. "The Human Serum Metabolome," PloS ONE 6(2): e16957. doi:10.1371/journal.pone.0016957.
Reid, B., et al., "Barrett's oesophagus and oesophageal adenocarinoma: time for a new synthesis," 2010, Nature Reviews Cancers, vol. 10, Februar, 86-101.
Sitter, B., et al., Quantification of Metabolites in Breast Cancer Patents with Different Clinical Prognosis Using HR MAS MR Spectroscopy, MNR Biomed. 2010, 23: 424-431.
Sova, H, et al., 8-Hydroxydeoxyguanosina: a new potential independent prognostic factor in breast cancer. British Journal of Cancer (2010) 102, 1018-1023.
Sugimoto, M, et al., Capillary electrophoresis mass spectrometry-based saliva metavolomics identified oral, break and pancreatic cancer-specific profiles, Metabolomics. (2010) 6:78-95.
Szymanska, E. et. al., Altered levels of nucleoside metabolife profiles in urogenital tract cancer measured by capillary electrophoresis, journal of Pharmaceutical and Biomedical Analysis 53 (2010) 1305-1312.
Walenta, S., et al. "High lactate levels predict likeihood of metastases, tumor recurrence, and restricted patient survival in human cervical cancer," Cancer Res, 2000: 60: 916-921.
Woo, H.M., et al., Mass spectrometry based metabolimic approaches in urinary biomarker study of women's cancers. Clinica Chimica Acta, vol. 400, Issies 1-2, Feb. 2009, pp. 63-69.
Wu, H., et al., "Metabolomic study for diagnostic model of oesophageal cancer using gas chromatography/mass spectrometry." J. Chromatogr. B 877 (2009) 3111-3117.
Yakoub, D., "Metabolic profiling detects field effects in nondyspiastic tissue from esophageal cancer patients," Cancer Res; 70(22) Nov. 15, 2010, 9130-9136.

(Continued)

*Primary Examiner* — Stephanie K Mummert
*Assistant Examiner* — Jonah Smith
(74) *Attorney, Agent, or Firm* — Bowditch & Dewey, LLP; Roger P. Zimmerman

(57) ABSTRACT

Methods for the detection and screening of esophageal adenocarcinoma (EAC) patients and for the monitoring of EAC treatment using a panel or panels of small molecule metabolite biomarkers are disclosed. In other aspects, methods for detection and screening for the progression of high-risk conditions (BE and HGD) to EAC and to monitoring treatment using a panel or panels of small molecule metabolite biomarkers are disclosed. The biomarkers are sensitive and specific for the detection of EAC, and can also be used to classify Barrett's esophagus (BE) and high-grade dysplasia (HGD), which are widely regarded as precursors of EAC.

5 Claims, 50 Drawing Sheets

(56) References Cited

OTHER PUBLICATIONS

Yousef, F., et al., "The incidence of esophageal cancer and high-grade dysplasia in Barrett's esophagus: a systematic review and meta-analysis." Am J Epidemiol 2008;168:237-249.

Zhang, J, et al., Detection of Metabolic-based Biomarkers for Human Esophageal Cancer Combing NMR and LC-MS, 2012, PLoSONE 7(1): e30161. doi:10.1371/journal.pone.0030181.

Zhang, Z, et al., "Serum and Urinary Metabonomic Study of Human Osteosarcoma." Journal of Profeome Research 2010, 9, 4861-4868.

Zheng, Y.F., et al., Urinary nucleosides as biological markers for patients with colorectal cancer., World J Gastroenterol, 2005:11(25):3871-3876.

David S. Wishart, Timothy Jewison, An Chi Guo, Michael Wilson, Craig Knox, Yifeng Liu, Yannick Djoumbou, Rupasri Mandal, Farid Aziat, Edison Dong, Souhaila Bouatra, Igor Sinelnikov, David Arndt, Jianguo Xia, Philip Liu, Faizath Yallou, Trent Bjorndahl, Rolando Perez-Pineiro, Roman Eisner, Felicity Allen, Vanessa Neveu, Russ Greiner, & Augustin Scalbert, JMDB 3.0—The Human Metabolme Database in 2013, Nucleic Acids Research, 2013, vol. 41, Datebase issue D801-D807.

* cited by examiner

Chemical shift (ppm)

METABOLITE BIOMARKERS FOR THE DETECTION OF ESOPHAGEAL CANCER USING NMR

RELATED APPLICATIONS

This application claims benefit of U.S. Provisional Patent Application 61/402,729, filed Sep. 3, 2010, and U.S. Provisional Patent Application 61/403,910, filed Sep. 23, 2010, the entire contents of which are incorporated by reference for all purposes.

TECHNICAL FIELD

The present disclosure generally relates to small molecule biomarkers comprising a set of metabolite species that is effective for the early detection of esophageal cancer, including methods for identifying such biomarkers within biological samples.

BACKGROUND

Esophageal cancer is a leading cause of death from cancer worldwide. The two principal types of esophageal cancer are squamous cell carcinoma and adenocarcinoma. Both are relatively uncommon in the U.S., comprising approximately 1% of all cancers. However, the incidence of adenocarcinoma is rising at a rapid rate. According to a report from American Cancer Society, 12,300 new cases and 12,100 deaths were reported in 2000, and the corresponding numbers for 2009 are 16,470 and 14,530, respectively. The 5-year survival rates for localized and all stages combined are 34% and 17%, respectively. Moreover, there is no currently reliable method for early detection or for the prediction of treatment outcome.

Barrett's esophagus (BE), high-grade dysplasia (HGD), and invasive cancer are thought to comprise a multi-step process in the development of esophageal adenocarcinoma (EAC). HGD has been considered as the immediate precursor of invasive adenocarcinoma. Since most patients with HGD are usually bearing or developing cancer, HGD has been regarded as a marker of progression to carcinoma. However, no intervention currently exists that prevents the progression of BE or HGD to esophageal cancer. The traditional methods for diagnosing esophageal cancer include endoscopy and barium swallow, but the poor specificity and sensitivity of these methods results in their detection only at an advanced stage. Recently, prognostic and predictive protein and genetic markers have been introduced to aid in the diagnosis of esophageal cancer. However, biomarkers effective at a potentially curative stage are lacking.

Metabotomics (or metabolite profiling) is the study of concentrations and fluxes of low molecular weight metabolites present in biofluids or tissues that provide detailed information on biological systems and their current status. The field of metabolomics emphasizes the multiplexed analysis of known and unknown metabolites in complex biological matrices such as pathological and normal tissue and biological fluids ("biofluids"). In various forms of metabolomics, the low molecular weight metabolites are detected and quantified by techniques such as nuclear magnetic resonance (NMR) spectrometry, gas chromatography-mass spectrometry (GC-MS), liquid chromatography-mass spectrometry (LC-MS), and capillary electrophoresis-mass spectrometry. Metabolomics aims to improve the molecular level understanding of metabolic pathways associated with many diseases or other biological states in a system biology approach.

Early diagnostic methods that offer high sensitivity and specificity for detecting esophageal cancer are in great demand. We have found that tests based on metabolic profiles that use a combination of the metabolic biomarkers that were identified using NMR with the metabolic biomarkers that were identified using LC-MS have improved sensitivity and selectivity compared to tests based on metabolic biomarkers that were identified either method alone.

SUMMARY OF THE INVENTION

The present disclosure provides methods for the detection and screening of esophageal adenocarcinoma (EAC) patients and for the monitoring of EAC treatment using a panel or panels of small molecule metabolite biomarkers. In other aspects, the present disclosure is directed to the detection and screening for the progression of high-risk conditions (BE and HGD) to EAC and to monitoring treatment using a panel or panels of small molecule metabolite biomarkers The biomarkers are sensitive and specific for the detection of EAC, and can be used to classify Barrett's esophagus (BE) and high-grade dysplasia (HGD), which are widely regarded as precursors of EAC.

A method of determining a stage in the progression of an esophageal adenocarcinoma a subject is disclosed, comprising the steps of: measuring the concentration of at least one metabolic biomarker in a sample of a biofluid from the subject, wherein the metabolic biomarker is a component of a panel of a plurality of biomarkers, and wherein a change in the concentration of the metabolic biomarker is characteristic of a transition from a first condition to a stage in the progression of esophageal adenocarcinoma, thereby determining the stage in the progression of the esophageal adenocarcinoma. In preferred embodiments, the method is based on metabolic profiles that use a combination of the metabolic biomarkers that were identified using NMR with the metabolic biomarkers that were identified using LC-MS. In some embodiments, the method further comprising the steps of measuring the concentration of at least one metabolic biomarker in a sample of a biofluid from a control source, wherein the metabolic biomarker is a component of a panel of a plurality of biomarkers; constructing a partial least squares model using the measured concentration of each metabolic biomarker in the sample from the subject for each metabolic biomarker of the plurality of biomarkers in the panel and the measured concentration of each metabolic biomarker in the sample from the subject for each metabolic biomarker of the plurality of biomarkers in the panel a control source; and determining the stage in the progression of the esophageal adenocarcinoma in view of the constructed partial least squares model. In some embodiments, the stage is selected from normal, Barrett's esophagus, high grade dysplasia, esophageal adenocarcinoma, early stage esophageal adenocarcinoma, or late stage esophageal adenocarcinoma.

In certain embodiments, the panel of metabolic markers comprises 2 to 18 compounds selected from the group consisting of lactic acid, valine, leucine, methionine, carnitine, tyrosine, tryptophan, 5-hydroxytryptophan, myristic acid, margaric acid, linolenic acid, linoleic acid, pyroglutamic acid, glutamine, β-hydroxybutyrate, citrate, lysine, creatinine, α-glucose, proline, histidine, alanine, glutamate, and mixtures thereof. In other embodiments the panel is selected from the group consisting of a) the panel consisting of glutamine, β-hydroxybutyrate, citrate, lysine, creatinine, lactate, and α-glucose; b) the panel consisting of glutamine, β-hydroxybutyrate, citrate, lysine, creatinine, lactate, α-glucose, leucine, valine, methionine, carnitine, tyrosine, tryptophan, 5-hydroxytryptophan, myristic acid, margaric acid, linolenic acid, and linoleic acid; c) the panel consisting of β-hydroxybutyrate, citrate, creatinine, lactate, and α-glucose; d) the panel consisting of glutamine, β-hydroxybutyrate, citrate, lysine, creatinine, lactate, α-glucose, leucine, acetone, acetoacetate and asparagine; e) the panel consisting of glutamine, β-hydroxybutyrate, citrate, lysine, creatinine, lactate, α-glucose, acetoacetate and asparagine; f) the panel consisting of glutamine, lysine, creatinine, acetoacetate and asparagine; g) the panel consisting of lysine, lactate, leucine, valine, methionine, tyrosine, myristic acid, margaric acid, linolenic acid, pyroglutamic acid, praline, histidine, alanine and glutamate; and h) the panel consisting of lactate, pyroglutamic acid, and proline. In preferred embodiments, the panel of metabolic biomarkers includes biomarkers that have been identified by a plurality of methods selected from nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry. In certain preferred embodiments, the panel of metabolic biomarkers includes biomarkers that have been identified by nuclear magnetic resonance (NMR) spectrometry and liquid chromatography-mass spectrometry (LC-MS).

In further embodiments, the panel is selected from the group consisting of a) the panel consisting of lactate, valine, leucine, methionine, tyrosine, tryptophan, myristic acid and linoleic acid; b) the panel consisting of glutamine, β-hydroxybutyrate, citrate, and lysine; c) the panel consisting of lactate, valine, leucine, methionine, tyrosine, tryptophan, myristic acid, linoleic acid, glutamine, β-hydroxybutyrate, lysine and citrate; d) the panel consisting of glutamine, β-hydroxybutyrate, citrate, lysine, creatinine, lactate, α-glucose, leucine, acetone, acetoacetate and asparagine; and e) the panel consisting of lactate, valine, leucine, methionine, carnitine, tyrosine, tryptophan, 5-hydroxytryptophan, myristic acid, linolenic acid and linoleic acid.

In other embodiments, the panel comprises a) at least one compound selected from the group consisting of glutamine, valine, leucine, methionine, lysine, tyrosine, tryptophan, β-hydroxybutyrate, citrate, lysine, creatinine, lactate, and α-glucose; b) at least one compound selected from the group consisting of myristic acid, margaric acid; linolenic acid, linoleic acid and β-hydroxybutyrate; and c) at least one compound selected from the group consisting of citrate, lactic acid, and α-glucose.

A method of detecting the esophageal cancer status within a biological sample is disclosed, comprising measuring one or more metabolite species within the sample by subjecting the sample to a nuclear magnetic resonance spectrometry analysis, the analysis producing a spectrum containing individual spectral peaks representative of the one or more metabolite species contained within the sample; identifying the at least one or more metabolite species contained within the sample; and correlating the measurement of the one or more metabolite species with an esophageal cancer status. In certain embodiments, one or multiple metabolite species is selected from the group consisting of leucine, β-hydroxybutyrate, lysine, glutamine, acetone, acetoacetate, citrate, unknown compound 1 appearing at 2.63 ppm, asparagine, creatinine, lactate, α-glucose, unsaturated lipids, the following lipid species: C=C—CH2-C=C, CH2-CO, CH2-C=C, CH2-CH2-C=C, CH2-CH2-CO, the lipoproteins VLDL2/LDL2, VLD1/LDL1; and combinations thereof. Typically, the sample comprises a biofluid, such as blood or serum.

In other aspects, a biomarker for detecting esophageal cancer is disclosed, comprising at least one metabolite species or parts thereof, selected from the group consisting of leucine, β-hydroxybutyrate, lysine, glutamine, acetone, acetoacetate, citrate, unknown compound 1 appearing at 2.63 ppm, asparagine, creatinine, lactate, α-glucose, unsaturated lipids, compounds characterized by NMR signals from the following lipid species: C=C—CH2-C=C, CH2-CO, CH2-C=C, CH2-CH2-C=C, CH2-CH2-CO, compounds characterized by NMR signals from the following lipoprotein signals: VLDL2/LDL2, VLDL1/LDL1; and combinations thereof.

A panel of biomarkers is disclosed comprising 2 to 18 compounds selected from the group consisting of lactic acid, valine, leucine, methionine, carnitine, tyrosine, tryptophan, 5-hydroxytryptophan, myristic acid, margaric acid, linolenic acid, linoleic acid, pyroglutamic acid, glutamine, β-hydroxybutyrate, citrate, lysine, creatinine, α-glucose, proline, histidine, alanine, glutamate, and mixtures thereof.

A kit is disclosed for the analysis of a sample of a biofluid of a subject, comprising aliquots of standards of each compound of a panel of metabolic biomarkers; an aliquot of an internal standard; and an aliquot of a control biofluid. Typically, the kit includes instructions for use. Generally, the control biofluid is serum from a control source that is in the same species as the subject. In certain embodiments, the internal standard is selected from the group consisting of trimethyisitylpropionic acid-$d_4$ sodium salt, tridecanoic acid and chlorophenylalanine.

In certain embodiments, the panel of metabolic markers comprises 2 to 18 compounds selected from the group consisting of lactic acid, valine, leucine, methionine, carnitine, tyrosine, tryptophan, 5-hydroxytryptophan, myristic acid, margaric acid, linolenic acid, linoleic acid, pyroglutamic acid, glutamine, β-hydroxybutyrate, citrate, lysine, creatinine, α-glucose, proline, histidine, alanine, glutamate, and mixtures thereof. In other embodiments the panel is selected from the group consisting of a) the panel consisting of glutamine, β-hydroxybutyrate, citrate, lysine, creatinine, lactate, and α-glucose; b) the panel consisting of glutamine, β-hydroxybutyrate, citrate, lysine, creatinine, lactate, α-glucose, leucine, valine, methionine, carnitine, tyrosine, tryptophan, 5-hydroxytryptophan, myristic acid, margaric acid, linolenic acid, and linoleic acid; c) the panel consisting of β-hydroxybutyrate, citrate, creatinine, lactate, and α-glucose; d) the panel consisting of glutamine, β-hydroxybutyrate, citrate, lysine, creatinine, lactate, α-glucose, leucine, acetone, acetoacetate and asparagine; e) the panel consisting of glutamine, β-hydroxybutyrate, citrate, lysine, creatinine, lactate, α-glucose, acetoacetate and asparagine; f) the panel consisting of glutamine, lysine, creatinine, acetoacetate and asparagine; g) the panel consisting of lysine, lactate, leucine, valine, methionine, tyrosine, myristic acid, margaric acid, linolenic acid, pyroglutamic acid, proline, histidine, alanine and glutamate; and h) the panel consisting of lactate, pyroglutamic acid, and proline.

In further embodiments, the panel is selected from the group consisting of a) the panel consisting of lactate, valine, leucine, methionine, tyrosine, tryptophan, myristic acid and linoleic acid; b) the panel consisting of glutamine, β-hydroxybutyrate, citrate, and lysine; c) the panel consisting of lactate, valine, leucine, methionine, tyrosine, tryptophan, myristic acid, linoleic acid, glutamine, β-hydroxybutyrate, lysine and citrate; d) the panel consisting of glutamine, β-hydroxybutyrate, citrate, lysine, creatinine, lactate, α-glucose, leucine, acetone, acetoacetate and asparagine; and e) the panel consisting of lactate, valine, leucine, methionine, carnitine, tyrosine, tryptophan, 5-hydroxytryptophan, myristic acid, linolenic acid and linoleic acid.

In other embodiments, the panel comprises a) at least one compound selected from the group consisting of glutamine, valine, leucine, methionine, lysine, tyrosine, tryptophan, β-hydroxybutyrate, citrate, lysine, creatinine, lactate, and α-glucose; b) at least one compound selected from the group consisting of myristic acid, margaric acid; linolenic acid, linoleic acid and β-hydroxybutyrate; and c) at least one compound selected from the group consisting of citrate, lactic acid, and α-glucose.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, in which corresponding reference characters indicate corresponding parts throughout the several views.

FIG. 4A, glutamine; FIG. 4B, β-hydroxybutyrate; FIG. 4C, citrate; FIG. 4D, unknown; FIG. 4E, lysine; FIG. 4F, creatinine; FIG. 4G, lactate; and FIG. 4H, α-glucose.

FIG. 7A, leucine; FIG. 7S, unsaturated lipids.

FIG. 8A shows the results of the PLS-DA model from the 12 metabolite markers from LC-MS analyses; FIG. 8B shows the ROC curve using the cross-validated predicted class values (AUROC=0.82); FIG. 8C shows the PLS-DA prediction of BE and HGD samples from the LC-MS model comparing EAC and normal controls.

FIG. 8D shows the results of the PLS-DA model using the 8 metabolite markers from NMR analyses; FIG. 8E shows the ROC curve using the cross-validated predicted class values (AUROC=0.86); FIG. 8F shows the PLS-DA prediction of BE and HGD samples from the NMR model comparing EAC and normal controls.

FIG. 8G shows the results of the PLS-DA model using the combination of the 12 LC-MS- and the 8 NMR-detected metabolite markers; FIG. 8H shows the ROC curve using the cross-validated predicted class values (AUROC=0.95); FIG. 8I shows the PLS-DA prediction of BE and HGD samples from the LC-MS AND NMR model comparing EAC and normal controls.

FIG. 9A shows the results of the PLS-DA model from the 7 metabolite markers from LC-MS analyses; FIG. 9B shows the ROC curve using the cross-validated predicted class values (AUROC=0.87); FIG. 9C shows the PLS-DA prediction for normal controls samples from the LC-MS model comparing EAC and BE+HGD.

FIG. 9D shows the results of the PLS-DA model using the 8 metabolite markers from NMR analyses; FIG. 9E shows the ROC curve using the cross-validated predicted class values (AUROC=0.72); FIG. 9F shows the PLS-DA prediction of normal controls samples from the NMR model comparing EAC and BE+HGD.

FIG. 9G shows the results of the PLS-DA model using the combination of the 7 LC-MS- and the 8 NMR-detected metabolite markers; FIG. 9H shows the ROC curve using the cross-validated predicted class values (AUROC=0.82); FIG. 9I shows the PLS-DA prediction of normal controls samples from the LC-MS AND NMR model comparing EAC and BE+HGD.

FIG. 10B, valine; FIG. 10C, leucine; FIG. 10D, methionine; FIG. 10E, tyrosine; FIG. 10F, tryptophan; FIG. 10G, myristic acid; FIG. 10H, linoleic acid; FIG. 10I, β-hydroxybutyrate; FIG. 10J, lysine; FIG. 10K, glutamine; and FIG. 10L, citrate.

FIG. 11A shows the results of the performance comparison of metabolic profiles between EAC patients and normal controls; FIG. 11B shows the ROC curve using the cross-validated predicted class values (AUROC=0.92); FIG. 11C shows the PLS-DA prediction for BE+HGD samples from the model comparing EAC and normal controls. FIG. 11D shows the results of the performance comparison of metabolic profiles between EAC patients and normal controls; FIG. 11E shows the ROC curve using the cross-validated predicted class values (AUROC=0.78); FIG. 11F shows the PLS-DA prediction for normal controls samples from the model comparing EAC and BE+HGD patients.

FIG. 12A, lactic acid; FIG. 12B, valine; FIG. 12C, leucine; FIG. 12D, methionine; FIG. 12E, carnitine; FIG. 12F, tyrosine; FIG. 12G, tryptophan; FIG. 12H, 5-hydroxytryptophan; FIG. 12I, myristic acid; FIG. 12J, margaric acid; FIG. 12K, linolenic acid; and FIG. 12L, linoleic acid.

FIG. 13A shows the results of the PLS-DA model for comparing normal controls and high-risk (BE+HGD) patients using the one metabolite biomarker from LC-MS analyses; FIG. 13B shows the ROC curve using the cross-validated predicted class values (AUROC=0.76); FIG. 13C shows the PLS-DA prediction for EAC samples using the same metabolite and cutoff.

FIG. 13D shows the results of the PLS-DA model comparing normal controls and high-risk (BE+HGD) patients using the 4 metabolite markers identified by NMR analyses; FIG. 13E shows the ROC curve using the cross-validated predicted class values (AUROC=0.80); FIG. 13F shows the PLS-DA prediction for EAC samples from the NMR model comparing normal controls and high-risk (BE+HGD) patients.

FIG. 13G shows the results of the PLS-DA model using the combination of the five LC-MS and NMR detected metabolite markers; FIG. 13H shows the ROC curve using the cross-validated predicted class values (AUROC=0.80); FIG. 13I shows the PLS-DA prediction for EAC samples from the LC-MS AND NMR model comparing normal controls and high-risk (BE+HGD) patients.

DETAILED DESCRIPTION OF EXEMPLARY EMBODIMENTS

Figure 1A:
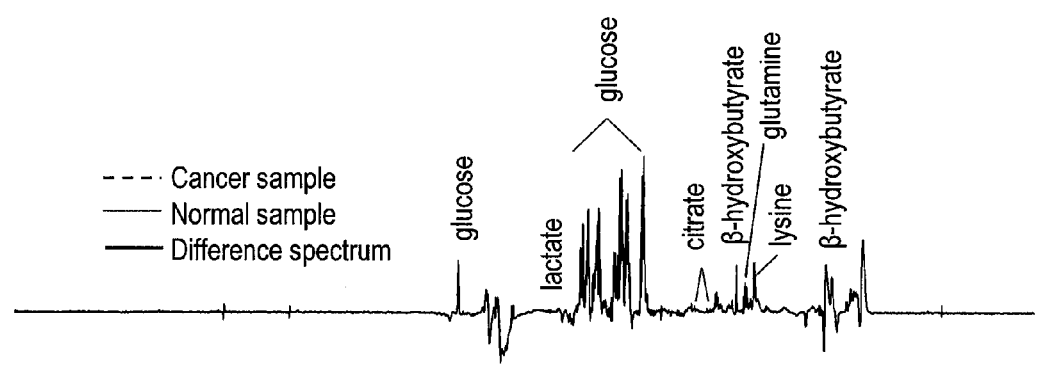
FIG. 1A shows a typical $^1$H NMR CPMG difference spectrum comparing the spectra from a healthy volunteer and an esophageal cancer patient, indicating the peaks associated with several exemplary compounds.

In certain aspects, the present disclosure is directed to methods for the detection and screening of esophageal adenocarcinoma (EAC) patients and to the monitoring of EAC treatment using a panel or panels of small molecule metabolite biomarkers. In other aspects, the present disclosure is directed to the detection and screening for the progression of high-risk conditions (BE+HGD) to EAC and to monitoring treatment using a panel or panels of small molecule metabolite biomarkers. The biomarkers are sensitive and specific for the detection of EAC, and can be used to classify Barrett's esophagus (BE) and high-grade dysplasia (HGD), which are widely regarded as precursors of EAC.

The present disclosure describes the use of $^1$H NMR, LC-MS and multivariate statistical analysis to detect molecular changes in human blood serum samples by comparing the metabolic profiles of patients with BE, HGD, and EAC, as well as normal controls, to identify a metabolite profile of, and biomarkers for EAC, as well as methods for monitoring the progression of EAC. The sensitivity and specificity of the study were evaluated for not only EAC, but also Barrett's esophagus (BE) and high-grade dysplasia (HGD).

The present disclosure provides monitoring tests based on panels of selected biomarkers that have been selected as being effective in detecting BE, HGD and EAC, as well as the progression of EAC. The tests have high degrees of clinical sensitivity and clinical specificity. The tests are based on biological sample classification methods that use a combination of nuclear magnetic resonance ("NMR") and mass spectrometry ("MS") techniques. More particularly, the present teachings take advantage of the combination of NMR and liquid chromatography-mass spectrometry ("LC-MS") to identify small molecule biomarkers comprising a set of metabolite species found in patient serum samples.

Unless defined otherwise, all technical and scientific terms used herein have the meaning commonly understood by a person skilled in the art to which this invention belongs. Numbers in scientific notation are expressed as product of a coefficient between 1 and 10 and ten raised to an integer power (e.g., $9.6 \times 10^{-4}$), or abbreviated as the coefficient followed by "E," followed by the exponent (e.g., 9.6E-04).

As used herein, "metabolite" refers to any substance produced or used during all the physical and chemical processes within the body that create and use energy, such as: digesting food and nutrients, eliminating waste through urine and feces, breathing, circulating blood, and regulating temperature. The term "metabolic precursors" refers to compounds from which the metabolites are made. The term "metabolic products" refers to any substance that is part of a metabolic pathway (e.g. metabolite, metabolic precursor).

As used herein, "biological sample" refers to a sample obtained from a subject. In preferred embodiments, biological sample can be selected, without limitation, from the group of biological fluids ("biofluids") consisting of blood, plasma, serum, sweat, saliva, including sputum, urine, and the like. As used herein, "serum" refers to the fluid portion of the blood obtained after removal of the fibrin clot and blood cells, distinguished from the plasma in circulating blood. As used herein, "plasma" refers to the fluid, non-cellular portion of the blood, as distinguished from the serum, which is obtained after coagulation.

As used herein, "subject" refers to any warm-blooded animal, particularly including a member of the class Mammalia such as, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female. As used herein, "normal control subjects" or "normal controls" means healthy subjects who are clinically free of cancer. "Normal control sample" or "control sample" refers to a sample of biofluid that has been obtained from a normal control subject.

As used herein, "detecting" refers to methods which include identifying the presence or absence of substance(s) in the sample, quantifying the amount of substance(s) in the sample, and/or qualifying the type of substance. "Detecting" likewise refers to methods which include identifying the presence or absence of BE, HGD and EAC or the progression of EAC.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

It is to be understood that this invention is not limited to the particular component parts of a device described or process steps of the methods described, as such devices and methods may vary. It is also to be understood that the terminology used herein is for purposes of describing particular embodiments only, and is not intended to be limiting. As used in the specification and the appended claims, the singular forms "a," "an," and "the" include plural referents unless the context clearly indicates otherwise. The terms "comprises," "comprising," and the like are intended to have the broad meaning ascribed to them in U.S. Patent Law and can mean "includes," "including" and the like.

Metabolite profiling uses high-throughput analytical methods such as nuclear magnetic resonance spectroscopy and mass spectroscopy for the quantitative analysis of hundreds of small molecules (less than ~1000 Daltons) present in biological samples. Owing to the complexity of the metabolic profile, multivariate statistical methods are extensively used for data analysis. The high sensitivity of metabolite profiles to even subtle stimuli can provide the means to detect the early onset of various biological perturbations in real time.

While these metabolite profiles were discovered using platforms of NMR and LC-MS methods, one of ordinary skill in the art will recognize that these identified biomarkers can be detected by alternative methods of suitable sensitivity, such as HPLC, immunoassays, enzymatic assays or clinical chemistry methods.

In one embodiment of the invention, samples may be collected from individuals over a longitudinal period of time. Obtaining numerous samples from an individual over a period of time can be used to verify results from earlier detections and/or to identity an alteration in marker pattern as a result of, for example, pathology. In preferred embodiments, the present disclosure provides methods of monitoring the (progression of BE, HGD and EAC. In certain embodiments, the present disclosure provides methods of assessing the effectiveness of the treatment of BE, HGD and EAC.

In one embodiment of the invention, the samples are analyzed without additional preparation and/or separation procedures. In another embodiment of the invention, sample preparation and/or separation can involve, without limitation, any of the following procedures, depending on the type of sample collected and/or types of metabolic products searched: removal of high abundance polypeptides (e.g., albumin, and transferrin); addition of preservatives and calibrants, desalting of samples; concentration of sample substances; protein digestions; and fraction collection. In yet another embodiment of the invention, sample preparation techniques concentrate information-rich metabolic products and deplete polypeptides or other substances that would carry little or no information such as those that are highly abundant or native to serum.

In another embodiment of the invention, sample preparation takes place in a manifold or preparation/separation device. Such a preparation/separation device may, for example, be a microfluidics device, such as a cassette. In yet another embodiment of the invention, the preparation/separation device interfaces directly or indirectly with a detection device. Such a preparation/separation device may, for example, be a fluidics device.

In another embodiment of the invention, the removal of undesired polypeptides (e.g., high abundance, uninformative, or undetectable polypeptides) can be achieved using high affinity reagents, high molecular weight filters, column purification, ultracentrifugation and/or electrodialysis. High affinity reagents include antibodies that selectively bind to high abundance polypeptides or reagents that have a specific pH, ionic value, or detergent strength. High molecular weight fitters include membranes that separate molecules on the basis of size and molecular weight. Such filters may further employ reverse osmosis, nanofiltration, ultrafiltration and microfiltration.

Ultracentrifugation constitutes another method for removing undesired polypeptides. Ultracentrifugation is the centrifugation of a sample at about 60,000 rpm while monitoring with an optical system the sedimentation (or lack thereof) of particles. Finally, electrodialysis is an electromembrane process in which ions are transported through ion permeable membranes from one solution to another under the influence of a potential gradient. Since the membranes used in electrodialysis have the ability to selectively transport ions having positive or negative charge and reject ions of the opposite charge, electrodialysis is useful for concentration, removal, or separation of electrolytes.

In another embodiment of the invention, the manifold or microfluidics device performs electrodialysis to remove high molecular weight polypeptides or undesired polypeptides. Electrodialysis can be used first to allow only molecules under approximately 35 30 kD to pass through into a second chamber. A second membrane with a very small molecular weight cutoff (roughly 500 D) allows smaller molecules to exit the second chamber.

Upon preparation of the samples, metabolic products of interest may be separated in another embodiment of the invention. Separation can take place in the same location as the preparation or in another location. In one embodiment of the invention, separation occurs in the same microfluidics device where preparation occurs, but in a different location on the device. Samples can be removed from an initial manifold location to a microfluidics device using various means, including an electric field. In another embodiment of the invention, the samples are concentrated during their migration to the microfluidics device using reverse phase beads and an organic solvent elution such as 50% methanol. This elutes the molecules into a channel or a well on a separation device of a microfluidics device.

Chromatography constitutes another method for separating subsets of substances. Chromatography is based on the differential absorption and elution of different substances. Liquid chromatography (LC), for example, involves the use of fluid carrier over a non-mobile phase. Conventional LC columns have an in inner diameter of roughly 4.6 mm and a flow rate of roughly 1 ml/min. Micro-LC has an inner diameter of roughly 1.0 mm and a flow rate of roughly 40 µl/min. Capillary LC utilizes a capillary with an inner diameter of roughly 300 µm and a flow rate of approximately 5 µl/min. Nano-LC is available with an inner diameter of 50 µm-1 mm and flow rates of 200 nl/min. The sensitivity of nano-LC as compared to HPLC is approximately 3700 fold. Other types of chromatography suitable for additional embodiments of the invention include, without limitation, thin-layer chromatography (TLC), reverse-phase chromatography, high-performance liquid chromatography (HPLC), and gas chromatography (GC).

In another embodiment of the invention, the samples are separated using capillary electrophoresis separation. This will separate the molecules based on their electrophoretic mobility at a given pH (or hydrophobicity). In another embodiment of the invention, sample preparation and separation are combined using microfluidics technology. A microfluidic device is a device that can transport liquids including various reagents such as analytes and elutions between different locations using microchannel structures.

Suitable detection methods are those that have a sensitivity for the detection of an analyte in a biofluid sample of at least 50 µM. In certain embodiments, the sensitivity of the detection method is at least 1 µM. In other embodiments, the sensitivity of the detection method is at least 1 nM.

In one embodiment of the invention, the sample may be delivered directly to the detection device without preparation and/or separation beforehand. In another embodiment of the invention, once prepared and/or separated, the metabolic products are delivered to a detection device, which detects them in a sample. In another embodiment of the invention, metabolic products in elutions or solutions are delivered to a detection device by electrospray ionization (ESI). In yet another embodiment of the invention, nanospray ionization (NSI) is used. Nanospray ionization is a miniaturized version of ESI and provides low detection limits using extremely limited volumes of sample fluid.

In another embodiment of the invention, separated metabolic products are directed down a channel that leads to an electrospray ionization emitter, which is built into a microfluidic device (an integrated ESI microfluidic device). Such integrated ESI microfluidic device may provide the detection device with samples at flow rates and complexity levels that are optimal for detection. Furthermore, a microfluidic device may be aligned with a detection device for optimal sample capture.

Suitable detection devices can be any device or experimental methodology that is able to detect metabolic product presence and/or level, including, without limitation, IR (infrared spectroscopy), NMR (nuclear magnetic resonance), including variations such as correlation spectroscopy (COSy), nuclear Overhauser enact spectroscopy (NOESY), and rotating frame nuclear Overhauser effect spectroscopy (ROESY), and Fourier Transform, 2-D PAGE technology, Western blot technology, tryptic mapping, in vitro biological assay, immunological analysis, LC-MS (liquid chromatography-mass spectrometry), LC-TOF-MS, LC-MS/MS, and MS (mass spectrometry).

For analysis relying on the application of NMR spectroscopy, the spectroscopy may be practiced as one-, two-, or multidimensional NMR spectroscopy or by other NMR spectroscopic examining techniques, among others also coupled with chromatographic methods (for example, as LC-NMR). In addition to the determination of the metabolic product in question, $^1$H-NMR spectroscopy offers the possibility of determining further metabolic products in the same investigative run. Combining the evaluation of a plurality of metabolic products in one investigative run can be employed for so-called "pattern recognition". Typically, the strength of evaluations and conclusions that are based on a profile of selected metabolites, i.e., a panel of identified biomarkers, is improved compared to the isolated determination of the concentration of a single metabolite.

For immunological analysis, for example, the use of immunological reagents (e.g. antibodies), generally in conjunction with other chemical and/or immunological reagents, induces reactions or provides reaction products which then permit detection and measurement of the whole group, a subgroup or a subspecies of the metabolic product(s) of interest. Suitable immunological detection methods with high selectivity and high sensitivity (10-4000 pg, or 0.02-2 pmoles), e.g., Baldo, B. A., et al, 1991, A Specific, Sensitive and High-Capacity Immunoassay for PAF, Lipids 26(12): 1136-1139, that are capable of detecting 0.5-21 ng/ml of an analyte in a biofluid sample (Cooney, S. J., et al., Quantitation by Radioimmunoassay of PAF in Human Saliva), Lipids 26(12): 1140-1143).

In one embodiment of the invention, mass spectrometry is relied upon to detect metabolic products present in a given sample. In another embodiment of the invention, an ESI-MS detection device. Such an ESI-MS may utilizes a time-of-flight (TOF) mass spectrometry system. Quadrupole mass spectrometry, ion trap mass spectrometry, and Fourier transform ion cyclotron resonance (FTICR-MS) are likewise contemplated in additional embodiments of the invention.

In another embodiment of the invention, the detection device interfaces with a separation/preparation device or microfluidic device, which allows for quick assaying of many, if not all, of the metabolic products in a sample. A mass spectrometer may be utilized that will accept a continuous sample stream for analysis and provide high sensitivity throughout the detection process (e.g., an ESI-MS). In another embodiment of the invention, a mass spectrometer interfaces with one or more etectrosprays, two or more electrosprays, three or more electrosprays or four or more electrosprays. Such electrosprays can originate from a single or multiple microfluidic devices.

In another embodiment of the invention, the detection system utilized allows for the capture and measurement of most or all of the metabolic products introduced into the detection device. In another embodiment of the invention, the detection system allows for the detection of change in a defined combination ("profile," "panel," "ensemble," or "composite") of metabolic products.

Profiles of metabolites in blood serum were constructed using NMR spectroscopy, LC-MS, and statistical analysis methods. The metabolite biomarkers discovered were selected to build a predictive model that was then used to test the classification accuracy.

Good sensitivity and selectivity were shown using the markers to predict the classification of healthy and disease samples. A pathway analysis indicated that altered energy metabolism and changes in the TCA cycle were the dominant factors in EAC biochemistry. The markers can be adapted for use on various diagnostics workstations or platforms in different formats (clinical chemistry, immunoassay, etc).

Example 1

$^1$H NMR-based metabolite profiling analysis is shown to be an effective approach for differentiating EAC patients and healthy subjects. Eight metabolites showed significant differences in their levels between cancer and control based on the Student's t-test, as shown in Table 4 and FIG. 3A-3D, A PLS-DA model built on these metabolites provided excellent classification between cancer and control, with the area under the receiver operating characteristic curve (AUROC) of >0.85 for both training and validation sample sets. Evaluated by the same model, the BE samples were of mixed classification and HGD samples were mostly classified as EAC samples. A pathway study indicated that altered energy metabolism and changes in the TCA cycle were the dominant factors in EAC biochemistry.

Chemicals.

Deuterium oxide ($D_2O$, 99.9% D) was purchased from Cambridge Isotope Laboratories, Inc. (Andover, Mass.). Trimethylsilylpropionic acid-$d_4$ sodium salt (TSP), tridecanoic acid, chlorophenylalanine, lactic acid, valine, leucine, methionine, carnitine, tyrosine, tryptophan, myristic acid, margaric acid, linolenic acid, linoleic acid and pyroglutamic acid were purchased from Sigma-Aldrich (analytical grade, St. Louis, Mo.). 5-hydroxytryptophan was purchased from Alfa-Aesar (analytical grade, Ward Hill, Mass.). HPLC-grade methanol and acetic acid were purchased from Fisher Scientific (Pittsburgh, Pa.). Deionized water was obtained from an EASYpure II UV water purification system (Barnstead International, Dubuque, Iowa).

Serum Sample Collection and Storage.

All samples were collected following the protocol approved by Indiana University School of Medicine and Purdue University institutional Review Boards. All subjects included in the study provided informed consent according to institutional guidelines. The clinicopathologic characteristics of the esophageal cancer patients are provided in Table 1, below. Whole blood samples were collected from patients with histologically documented BE (n=5), BE with HGD ("HGD," n=11), and adenocarcinoma (n=68). Blood samples from 34 healthy volunteers served as controls. Each blood sample was allowed to clot for 45 min and then centrifuged at 2,000 rpm for 10 min. The serum was collected, aliquoted in a separate vial, frozen, and shipped over dry ice to Purdue University (West Lafayette, Ind.), where they were stored at −80° C. until use.

Due to the limited amounts of some samples, 1 EAC, 2 HGD and 2 BE samples were removed for the LC-MS experiments and further analysis in Example 2, and the corresponding NMR data was also excluded from the combined analysis and discussion. The demographic and clinical parameters for the reduced set of 67 esophageal adenocarcinoma (EAC) patients are summarized in Table 2, below.

Sample Preparation and Data Acquisition.

For LC-MS analysis, frozen serum samples were thawed, and the protein was precipitated by mixing 100 µL serum and 200 µL methanol. Two internal standards, tridecanoic acid and chlorophenylalanine were also included to monitor the extraction efficiency. The supernatant solution obtained after protein removal was dried under vacuum and the obtained residue was reconstituted in 15 µL methanol/water (1:1) solution. Separately, a pooled sample was obtained by mixing together 20 human serum samples randomly selected from all the samples, and the metabolites were extracted using the same procedure as above. This pooled sample, referred to as the quality control (QC) matrix sample, was subjected to analysis periodically between every 10 samples. QC sample data also served as technical replicates throughout the data set to assess process reproducibility. LC-MS analysis was performed using an Agilent LC-QTOF system (Agilent Technologies, Santa Clara, Calif.) consisting of an Agilent 1200 SL liquid chromatography system coupled online with an Agilent 6520 time-of-flight mass spectrometer. A 3 µL aliquot of reconstituted sample was injected onto a 2.1×50 mm Agilent Zorbax Extend-C18 1.8 µm particle column with a 2.1× 30 mm Agilent Zorbax SB-C8 3.5 µm particle guard column, which were both heated to 60° C. Serum metabolites were gradient-eluted at 600 µL/min using mobile phase A: 0.2% acetic acid in water and mobile phase B: 0.2% acetic acid in methanol (2% to 98% B in 13 min., 98% B for 6 min). Electrospray ionization (ESI) was used in positive mode. The MS interface capillary was maintained at 325° C., with a sheath gas flow of 9 L/min. The spray voltage for positive ion injection was 4.0 kV. The mass analyzer was scanned over a range of 50-1000 m/z. Agilent MassHunter Workstation LC-TOF and QTOF Acquisition software (B.02.01) was used for automatic peak detection and mass spectrum deconvolution.

For NMR studies, frozen serum samples were thawed, and 200 µL was mixed with 350 µL of $D_2O$. Resulting solutions were transferred to 5-mm NMR tubes. A 60 µL solution of TSP (0.12 mg/mL) in a sealed capillary was utilized as an internal standard, which acted as the chemical shift reference ($\delta$=0.00). All $^1H$ NMR experiments were carried out at 25° C. on a Bruker DRX-500 spectrometer equipped with a triple resonance $^1H$ inverse detection probe with triple axis magnetic field gradients. $^1H$ NMR spectra were acquired using the standard one-dimensional CPMG (Carr-Purcell-Meiboom-Gill) pulse sequence with water signal (presaturation. Each dataset was averaged over 64 transients using 16K time domain points, acquired using a spectral width of 6,000 Hz. The data were Fourier transformed after multiplying by an exponential window function with a line broadening of 1 Hz, and the spectra were phase and baseline corrected using Bruker TopSpin software (version 3.0).

Data analysis LC-MS data was processed using Agilent's MassHunter Qualitative Analysis software (version B.03.01) for compound identification, A list of ion intensities for each detected peak was generated using a retention time (RT) index and m/z data as the identifiers for each ion. Agilent MassHunter Workstation Mass Profiler Professional software (version B.02.00) was then used for compound peak alignment. A filter was set to remove any metabolite signals that had missing peaks (ion intensity=1) in more than 10% of the samples in any group. Peaks from internal standards were also removed. Finally, the Agilent Formula Database (Agilent, 2010) was used for compound identification by matching the mass spectrum and RT to a database of metabolite compounds. Unpaired Student's t-test analysis of the data was performed to assess the differences of detected compound intensities among EAC, BE and HGD samples, and normal controls. Metabolites with low p-values ($<0.05$) were selected as potential biomarker candidates and verified from the mass spectra and RTs of authentic commercial compounds nm separately. The fold change (FC) for each metabolite was calculated to determine metabolite's variation between the groups.

NMR spectral regions were binned to 4K buckets of equal width (1.5 Hz) to minimize errors due to any fluctuations of chemical shifts arising from pH or ion concentration variations. Each spectrum was aligned to the methyl peak of alanine at 1.48 ppm, and normalized using the integrated TSP signal. Spectral regions of 0.3 to 10.0 ppm were used for the analysis after deleting the water and urea signals (4.5 to 6.0 ppm). Univariate analysis was performed by applying the unpaired Student's t-test to identify significantly different spectral bins among EAC, BE and HGD patients, and normal controls. Bins that showed significant differences between various patient/controls groups were then assigned to the corresponding metabolites by comparing chemical shifts and multiplicities of peaks to the literature or online databases. The characteristic spectral regions for each metabolite were integrated, and p-values and fold changes between different groups were calculated.

To better visualize the differences between spectra, partial least-squares (PLS), a robust supervised method to detect subtle changes between group variations, was employed. In Example 1, PLS fits to data matrices X (which consists of NMR spectra) and Y (that is set to "1" for cancer and "0" for control), were performed to display these data as score plots and loading plots. The NMR spectral signals or variables, were auto scaled (by subtracting the mean value of each variable and dividing by its standard deviations) prior to all statistical analyses. The score plot shows the possible relationships (or clustering) among the samples to estimate the classification; each orthogonal axis is named a latent variable (LV). Corresponding loading plot of each UV contains the weight or contribution of each variable in the modeling. To explore potential biomarker candidates, univariate analysis was performed by calculating the p-value (unpaired Student's t-test), and a Benjamini-Hochberg correction was followed in order to control false discovery errors originating from multiplicity. Subsequently, a partial least-squares discriminant analysis (PLS-DA) model was built to evaluate the biomarker candidates when combined as a metabolite profile. Predictions were made visually using a Y-predicted scatter plot with a cut-off value chosen for potential class membership. The NMR data were imported into Matlab (R2008a, Mathworks, Natick Mass.) installed with a PLS toolbox (version 4.1, Eigenvector Research, Inc) for PLS and PLS-DA analysis.

For Example 2, below, the MS/NMR data of the selected statistically significant metabolites (with p<0.05) were imported into Matlab (R2008a, Mathworks, Natick, Mass.) installed with a PLS toolbox (version 4.1, Eigenvector Research, Inc., Wenatchee, Wash.) for DA analyses. The X matrix, consisting of the MS/NMR spectral data, was autoscaled prior to all statistical analyses. Depending on the group, each subject was assigned a "0" (i.e., patient) and "1," (i.e., normal control) to serve as the (one-dimensional) Y matrix. Leave-one-out cross validation (CV) was chosen, and the number of latent variables (LVs) was selected according to the minimum root mean square error of CV procedure. Predictions were made visually using a Y-predicted scatter plot with a cut-off value chosen to minimize errors in class membership. The R statistical package (version 2.8.0) was used to generate receiver operating characteristics (ROC) curves, calculate and compare sensitivity, specificity and area under the ROC curve (AUROC).

TABLE 1

Clinicopathologic characteristics of esophageal cancer patients

| Training Group (G1) | | | | Test Group (G2) | | | |
|---|---|---|---|---|---|---|---|
| Patient no. | Age | Sex | Clinical Stage | Patient no. | Age | Sex | Clinical Stage |
| 1 | 69 | F | T3N1 | 1 | 66 | M | T3N1 |
| 2 | 69 | M | T1N0 | 2 | 60 | M | T3N1 |
| 3 | 63 | M | T3N1 | 3 | 64 | M | T3N1 |
| 4 | 71 | M | T1N0 | 4 | 58 | F | T4N1 |
| 5 | 77 | M | T3N1 | 5 | 68 | M | M |
| 6 | 49 | M | M | 6 | 46 | M | M1a |
| 7 | 78 | M | T3N1 | 7 | 78 | M | T3N1 |
| 8 | 61 | M | M | 8 | 78 | M | T1N0 |
| 9 | 69 | M | T1N0 | 9 | 66 | M | T3N1 |
| 10 | 57 | F | T1N0 | 10 | 53 | M | T2N0 |
| 11 | 65 | M | T3N1M1a | 11 | 54 | F | T3N1M1a |
| 12 | 60 | F | T2N0 | 12 | 62 | M | T1N0 |
| 13 | 68 | M | unknown | 13 | 59 | F | unknown |
| 14 | 51 | M | unknown | 14 | 75 | M | T3N0 |
| 15 | 47 | F | T3N0 | 15 | 78 | M | T2N1 |
| 16 | 56 | M | T2N1M1a | 16 | 72 | M | T3N0 |
| 17 | 71 | M | T2Nx | 17 | 77 | F | T3N0 |
| 18 | 58 | M | unknown | 18 | 72 | M | unknown |
| 19 | 91 | M | T3N0 | 19 | 82 | F | T3N1M1b |
| 20 | 74 | M | T3N1M1a | 20 | 58 | M | T3N1 |
| 21 | 62 | M | T3N1 | 21 | 67 | M | T3N1 |
| 22 | 64 | M | T3N1 | 22 | 67 | M | T3N1M1 |
| 23 | 53 | M | T2N1M1 | 23 | 77 | M | T1N0 |
| 24 | 54 | M | T2N1M1a | 24 | 62 | M | T3N1 |
| 25 | 64 | F | T3N1 | 25 | 67 | M | T3Nx |
| 26 | 72 | M | T3N1M1a | 26 | 54 | M | T3N1 |
| 27 | 64 | M | T3N1 | 27 | 72 | M | T3N1 |
| 28 | 71 | M | T2N0 | 28 | 67 | M | T3N1M1 |
| 29 | 65 | M | T3N0 | 29 | 66 | M | unknown |
| 30 | 57 | M | T3N1M1a | 30 | 64 | M | T2N1M1 |
| 31 | 78 | M | T4N1 | 31 | 71 | M | T3N1M1 |
| 32 | 66 | M | T2N1 | 32 | 68 | M | T3 |
| 33 | 74 | M | T3N3M1 | 33 | 62 | F | T2N1 |
| 34 | 63 | M | T3N1 | 34 | 61 | M | T2Nx |

TABLE 2

Demographic and clincial parameters for esophageal adenocarcinoma (EAC) patients

| Parameter | | EAC patients (n = 67) |
|---|---|---|
| Average age (range) | | 65.6 (46-91) |
| Number of males | | 56 |
| Cancer stage | T1 | 7 |
| | T2 | 11 |
| | T3 | 36 |
| | T4 | 2 |
| | N0 | 16 |
| | N1 | 37 |
| | M | 18 |

Figure 1B:
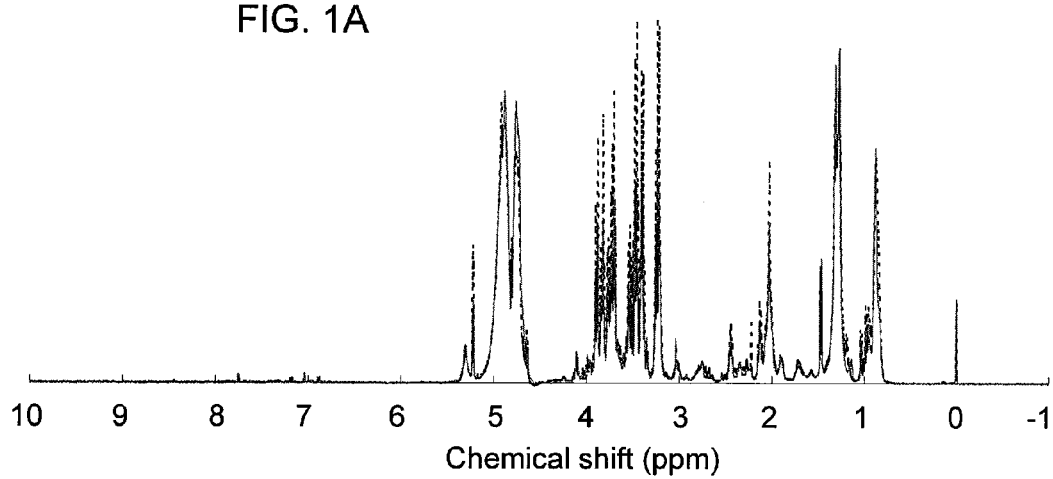
FIG. 1B shows typical $^1$H NMR CPMG serum spectra from a healthy volunteer ("Normal sample," continuous line) and an esophageal cancer patient ("Cancer Sample," dashed line).
Figure 2:
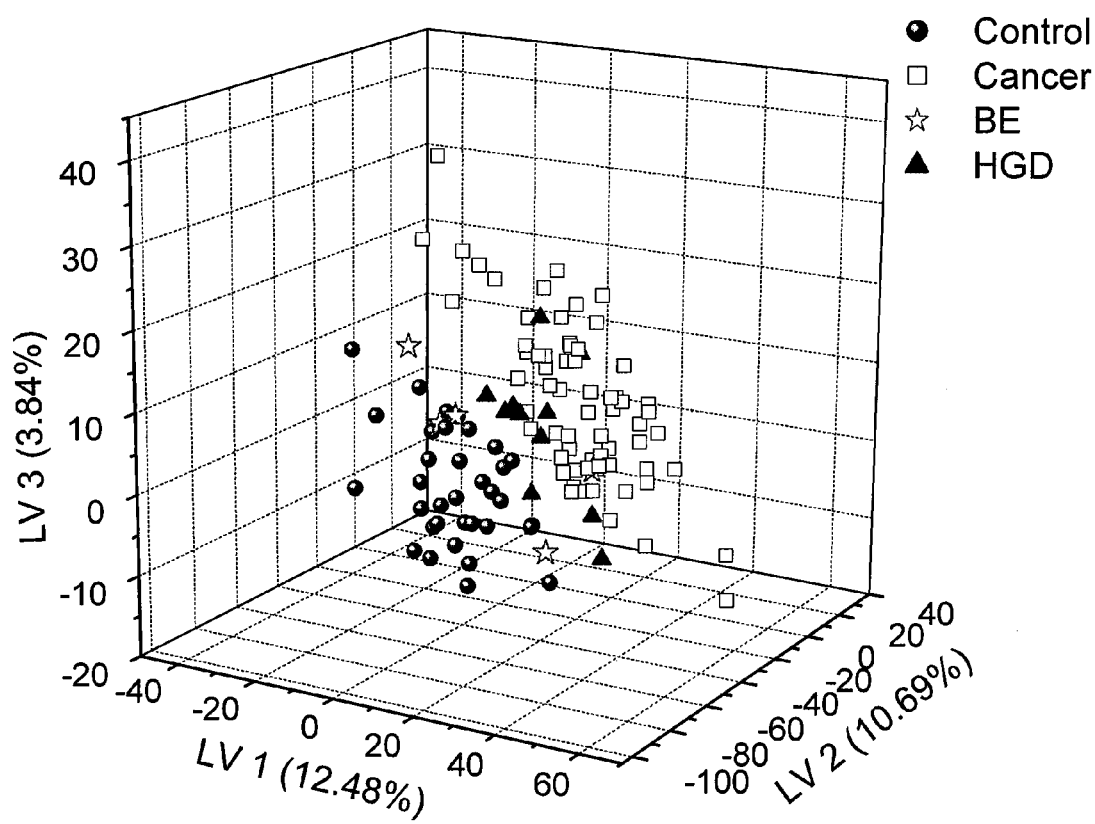
FIG. 2 shows a PLS score plot based on the $^1$H NMR spectra of normal control subjects, BE, HGD and esophageal cancer patients in the three dimensional space defined by latent variables LV1, LV2 and LV3.

FIG. 1A shows a difference spectrum (cancer sample—control sample) of representative $^1$H NMR spectra of samples from the control group and the esophageal cancer group. The original spectra are shown in FIG. 1B, where the solid line indicates the spectrum of the sample from the control group and the dashed line the spectrum of the sample from the esophageal cancer group. The cancer and control samples could be clearly separated when contributions from many signals in the spectra are combined, as illustrated in the PLS score plot shown in FIG. 2, where filled circles represent data from control samples, open squares represent data from EAC samples, stars represent data from BE samples and filled triangles represent data from HGD samples. The BE and samples appeared between the cluster of control samples and the cluster of EAC samples, with HGD samples were generally closer to the cluster of the EAC samples. Review of the PLS loadings indicated that a large number of low level signals contributed and few easily detected signals dominated.

To better explore and evaluate potential biomarker candidates, all the control and EAC samples were randomly and equally divided into 2 groups, G1 as the training group, and G2 as the test group, Table 1, above. As shown in Table 3, for the G1 samples, p-values were calculated for all data points. As shown in Table 3, nineteen spectral regions which showed a statistical difference between cancer and control (uncorrected p-value<0.05) were identified and integrated. The p values along with a Benjamini-Hochberg correction were calculated for the integrated peaks, and 14 peaks with a now corrected p-value<0.05 were short-listed. According to the literature, these peaks belonged to 8 potential biomarker candidates, which were identified as β-hydroxybutyrate, lysine, glutamine, citrate, creatinine, lactate, α-glucose and an unknown compound ("unknown 1"). The same metabolite peaks in G2 were also integrated. Fold-changes were calculated by dividing the average EAC values by the average control values. All the metabolites concentrations collected were increased in the EAC samples, as shown in Table 4, below.

TABLE 3

Summary of spectral regions influencing separation of control samples from EAC samples in the training group.

| chemical shift (δ)† | multi-plicity† | assignment | p-value | Benjamini-Hochberg§ correction |
|---|---|---|---|---|
| 1.20 | d | β-hydroxybutyrate | $4.99 \times 10^{-3}$ | $7.90 \times 10^{-3}$ |
| 1.69 | m | lysine | $6.59 \times 10^{-4}$ | $1.57 \times 10^{-3}$ |
| 1.91 | m | lysine | $4.61 \times 10^{-4}$ | $1.25 \times 10^{-3}$ |
| 2.09 | m | glutamine | $2.22 \times 10^{-2}$ | $3.02 \times 10^{-2}$ |
| 2.31 | m | β-hydroxybutyrate | $2.25 \times 10^{-5}$ | $1.42 \times 10^{-4}$ |

TABLE 3-continued

Summary of spectral regions influencing separation of
control samples from EAC samples in the training group.

| chemical shift (δ)[†] | multi-plicity[†] | assignment | p-value | Benjamini-Hochberg[§] correction |
|---|---|---|---|---|
| 2.35 | m | β-hydroxybutyrate | $2.99 \times 10^{-3}$ | $5.16 \times 10^{-3}$ |
| 2.39 | m | β-hydroxybutyrate | $2.40 \times 10^{-6}$ | $2.28 \times 10^{-5}$ |
| 2.53 | d | citrate | $8.70 \times 10^{-5}$ | $3.31 \times 10^{-4}$ |
| 2.63 | m | Unknown 1 | $1.56 \times 10^{-6}$ | $2.97 \times 10^{-5}$ |
| 2.69 | d | citrate | $6.82 \times 10^{-4}$ | $1.44 \times 10^{-3}$ |
| 3.00 | t | lysine | $3.04 \times 10^{-4}$ | $9.63 \times 10^{-4}$ |
| 4.05 | s | creatinine | $1.50 \times 10^{-2}$ | $2.19 \times 10^{-2}$ |
| 4.11 | q | lactate | $1.40 \times 10^{-3}$ | $2.66 \times 10^{-3}$ |
| 5.22 | d | α-glucose | $3.15 \times 10^{-5}$ | $1.49 \times 10^{-4}$ |

[†]The chemical shift and multiplicity are NMR dependent quantities that indicate the spectral peak position and number of peaks, respectively that allow the spectroscopist to identify the chemical compound (s = singlet; d = doublet; t = triplet; q = quartet; m = complex multiplet).
[§]The Benjamini-Hochberg correction is used to reduce the false discovery rate by adjusting the p-value to take into account the use of multiple variable comparisons.

Figure 3A:
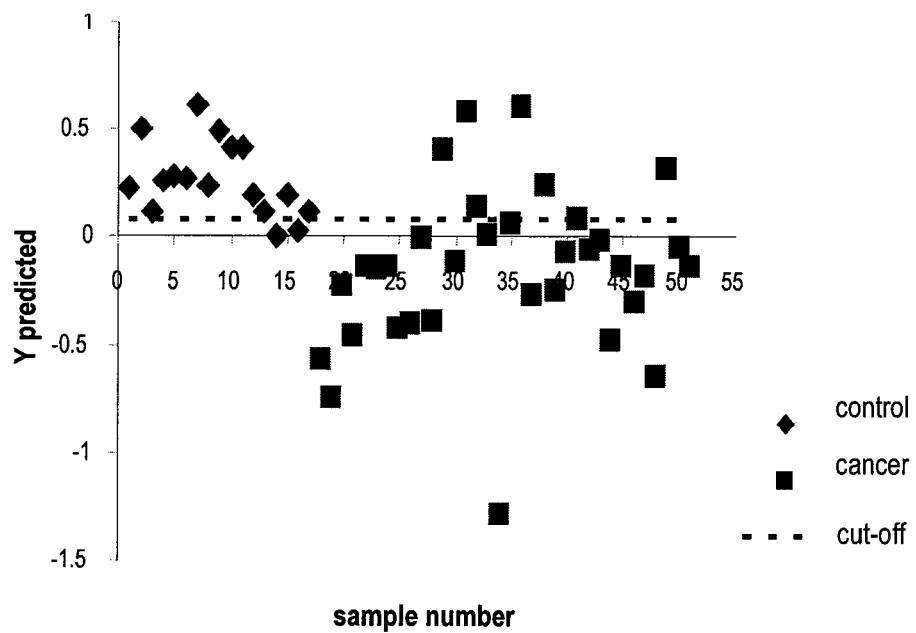
FIG. 3A-FIG. 3D show the results of the PLS-DA model from the 8 metabolite biomarkers for the training group (G1, FIG. 3A) and the test group (G2, FIG. 3C), and ROC curves using the cross-validated predicted class values for G1 (FIG. 3B) and G2 (FIG. 3D).
Figure 3B:
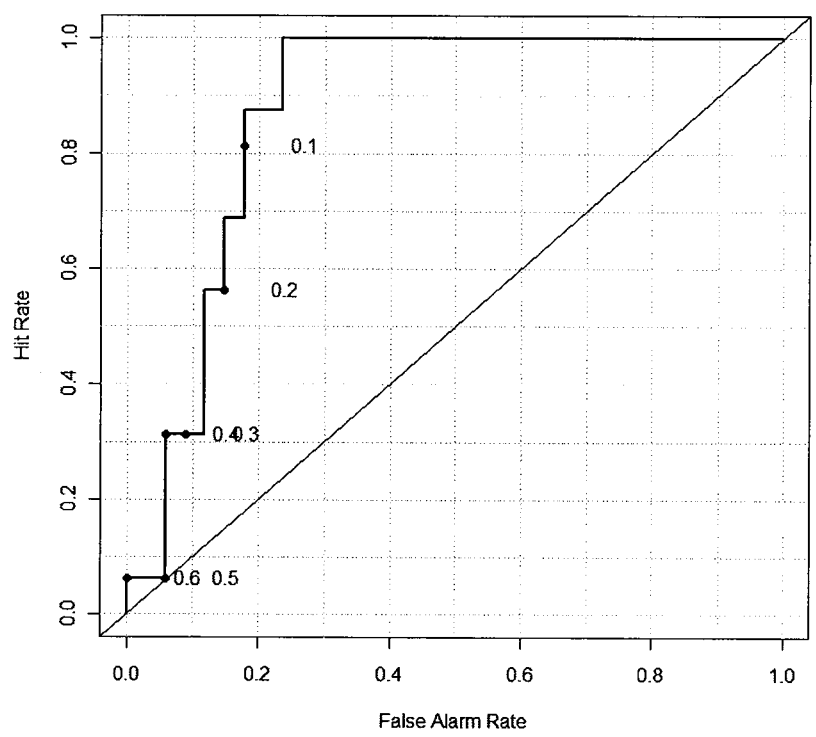
Figure 3C:
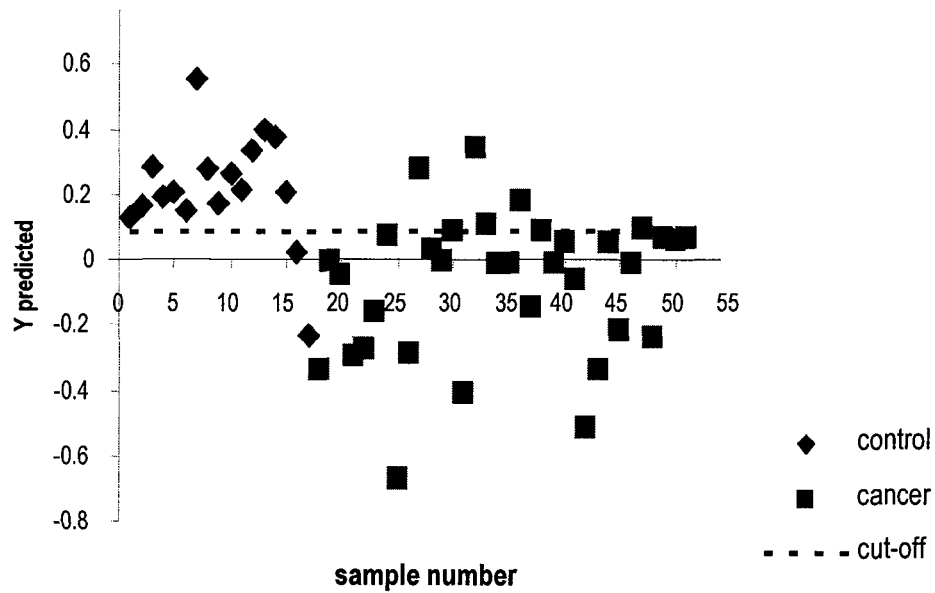
Figure 3D:
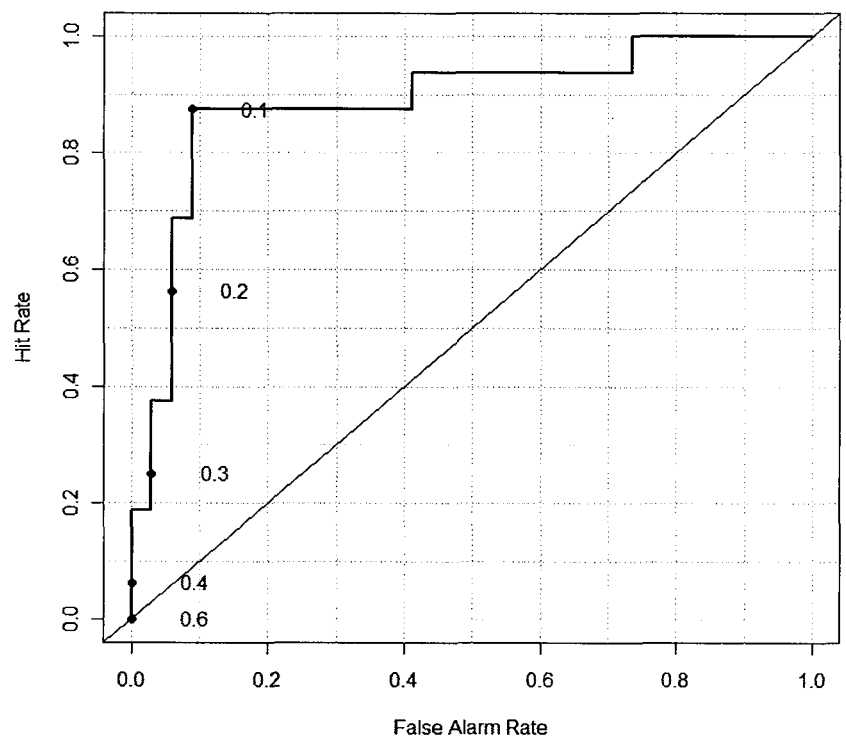

PLS-DA was then used to build a multivariate model to evaluate the utility of a panel of the biomarker candidates taken together. The 8 metabolite biomarkers in the G1 samples were selected as the variables to build the PLS-DA model. Leave-one-out cross-validation was performed to obtain the best model and avoid over-fitting. Three LVs were used and the cross validation error was estimated as 14.7%. The model was then reapplied to the samples in G2. The PLS-DA score plots of G1 and G2 are shown as in FIG. 3A and FIG. 3C, respectively. Most samples were well classified using a cut-off of 0.0855. In FIG. 3B and FIG. 3D, receiver operating characteristic (ROC) curve analysis using the cross-validated predicted Y (predicted class) values was utilized to judge the sensitivity and specificity of the PLS-DA model. The area wider the receiver operating characteristic curve (AUROC) for the G1 and G2 samples were 0.875 and 0.888, respectively. The sensitivity and specificity for EAC detection were 88% and 82% for G1, and 88% and 92% for G2, respectively.

TABLE 4

Metabolites showing a significant separation of control samples from
EAC samples in the training group and their fold change values.

| metabolite | p-value [a] | fold change |
|---|---|---|
| glutamine | $3.02 \times 10^{-2}$ | 1.10 |
| β-hydroxybutyrate | $2.28 \times 10^{-5}$ | 1.31 |
| citrate | $3.31 \times 10^{-4}$ | 1.26 |
| Unknown 1 | $2.97 \times 10^{-5}$ | 1.26 |
| lysine | $9.63 \times 10^{-4}$ | 1.10 |
| creatinine | $2.19 \times 10^{-2}$ | 1.23 |
| lactate | $2.66 \times 10^{-3}$ | 1.28 |
| α-glucose | $1.49 \times 10^{-4}$ | 1.20 |

[a] Benjamini-Hochberg correction was used to control for possible false discovery due to the use of multiple variable comparison. The correction used in this case was corrected using 19 variables.

Since metabolic differences might act as a useful tool to grade tumors compared with the classical individual metabolite-based targeted analysis, p-values and box-and-whisker plot studies were used to evaluate the metabolite biomarker profile as a tool for identifying patients with early stage disease. The p-value results of different group comparisons of control, BE, HGD, and EAC samples are listed in Table 5. The low p-values (p<0.05) for comparison of the metabolite biomarkers for all the control and EAC samples demonstrated that the differences in the concentrations of these compounds were statistically significant. However, comparisons of adjoining stages always produced high and non-significant p values. Comparison of HGD with controls showed that the changes in the concentrations of citrate, creatinine, lactate, α-glucose, and the unknown 1 compound were significant (p<0.05). Comparison of BE to EAC showed that the changes in the concentrations of β-hydroxybutyrate and glutamine were significant.

Figure 4A:
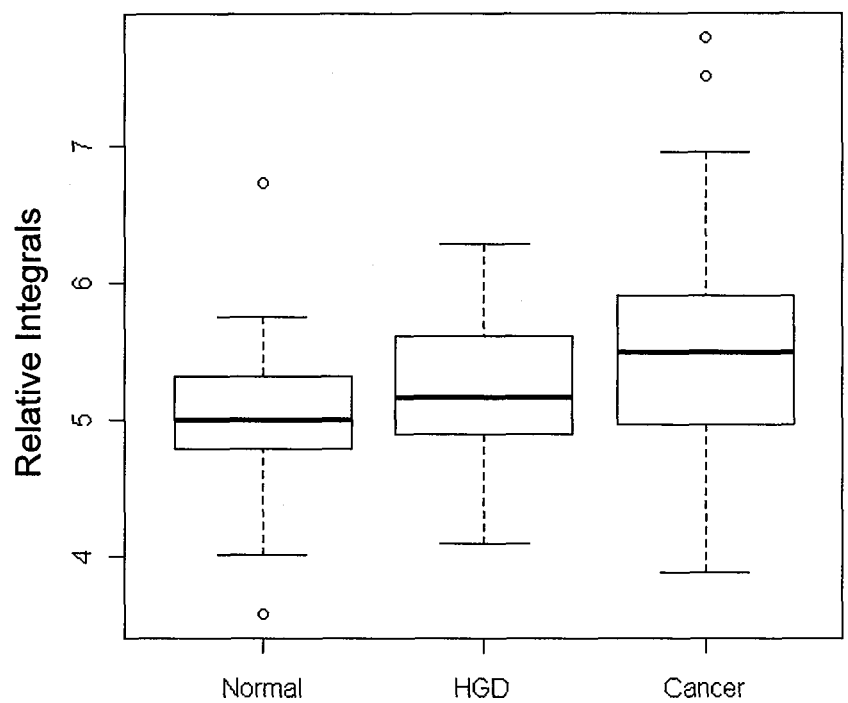
FIG. 4A-FIG. 4H show box-and-whisker plots comparing the groups "Normal," "HGD" and "Cancer" for several biomarkers, in which the y axis for each plot indicates the relative concentration level of each metabolite normalized by the internal standard TSP.
Figure 4B:
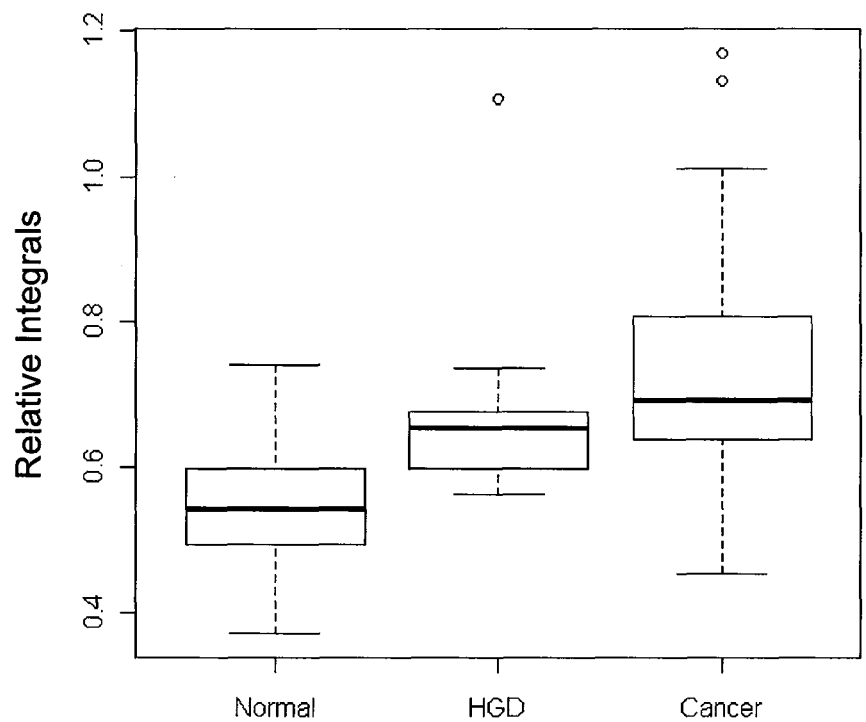
Figure 4C:
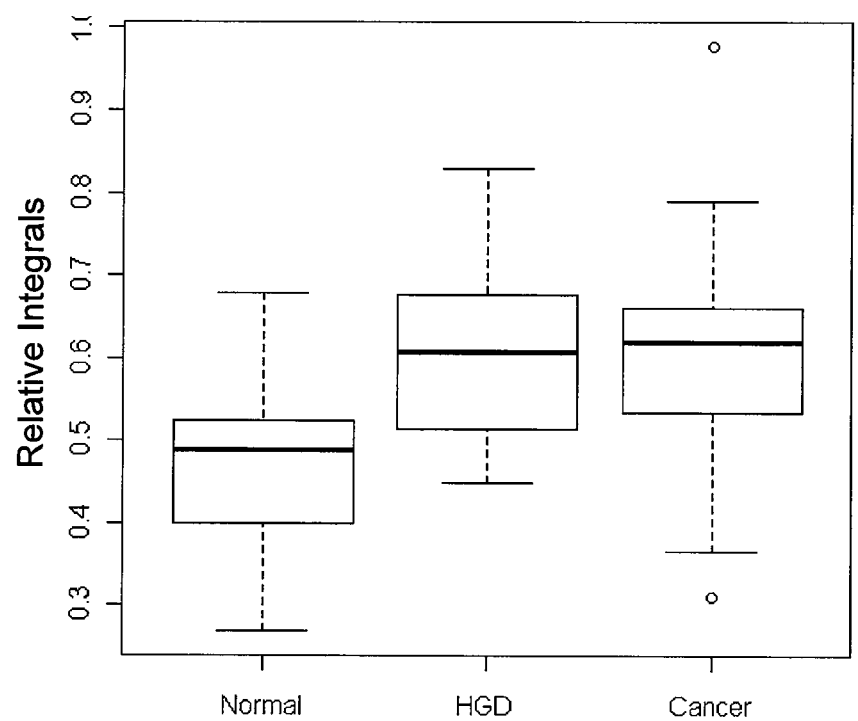
Figure 4D:
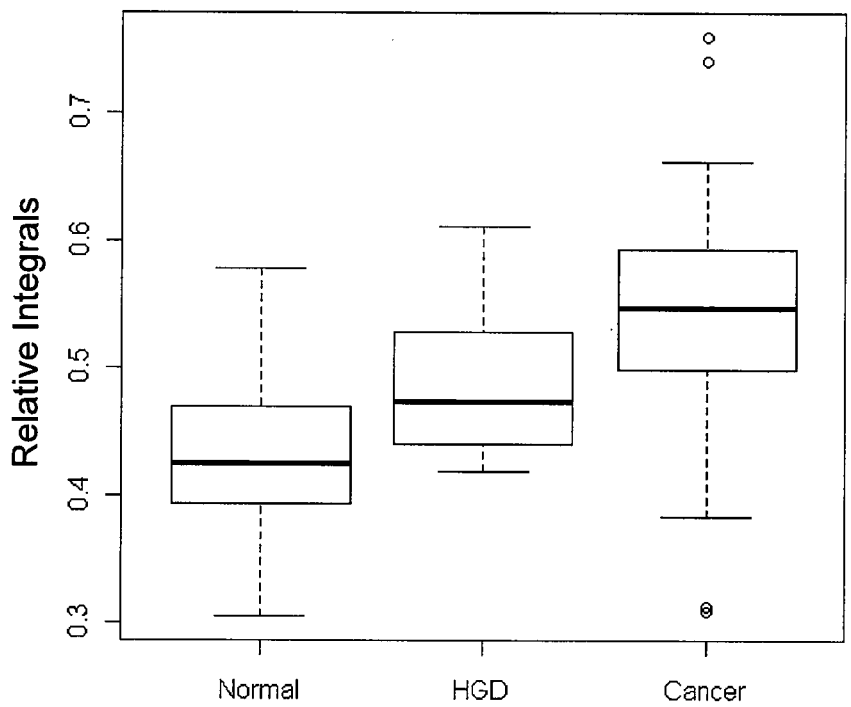
Figure 4E:
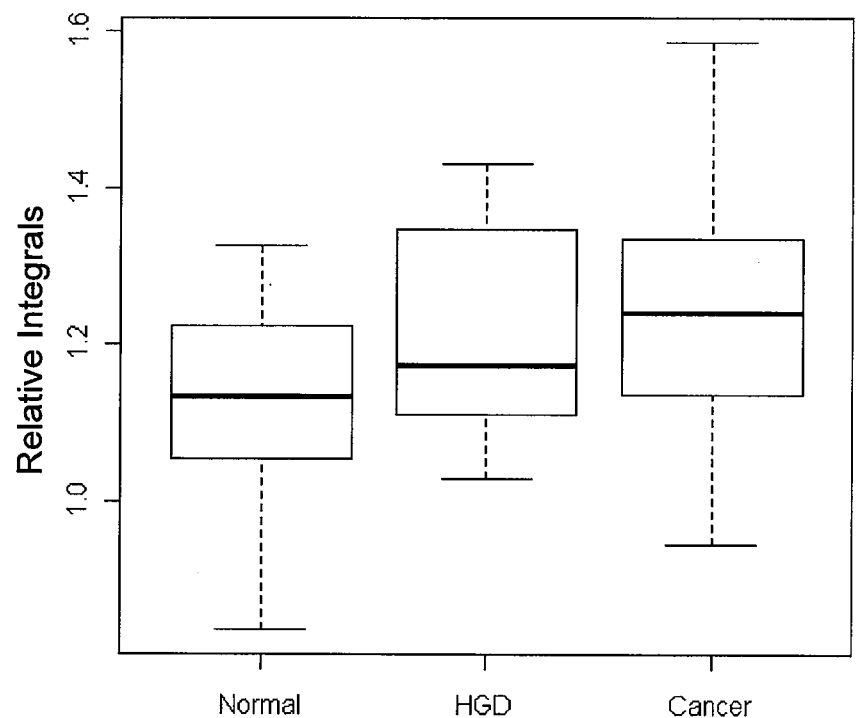
Figure 4F:
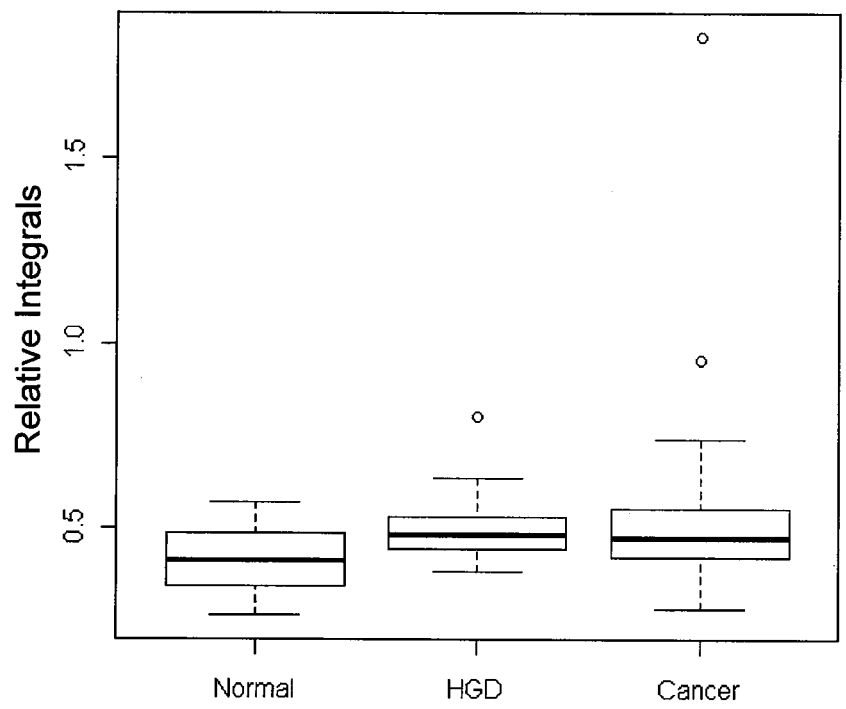
Figure 4G:
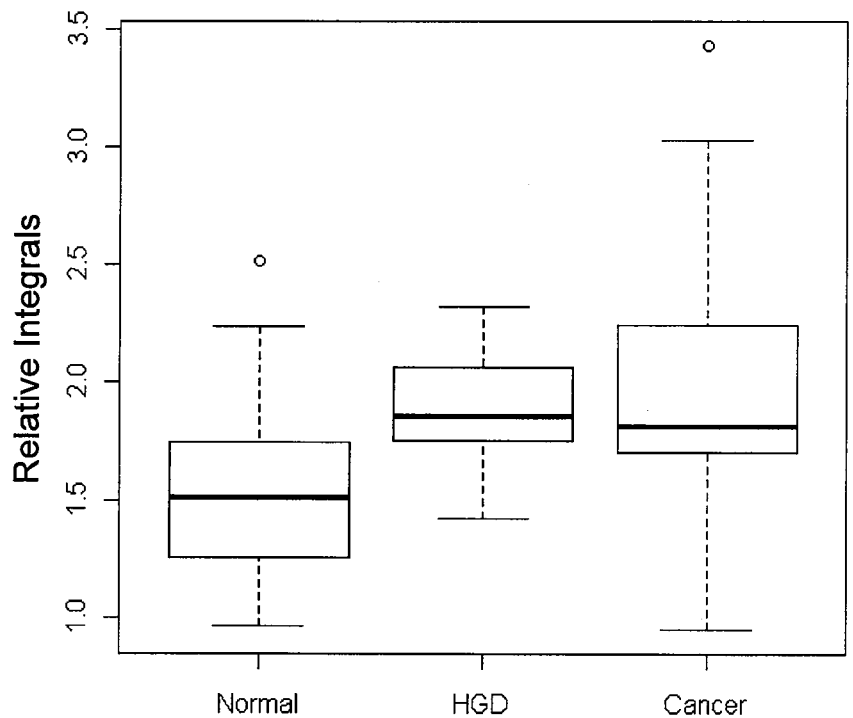
Figure 4H:
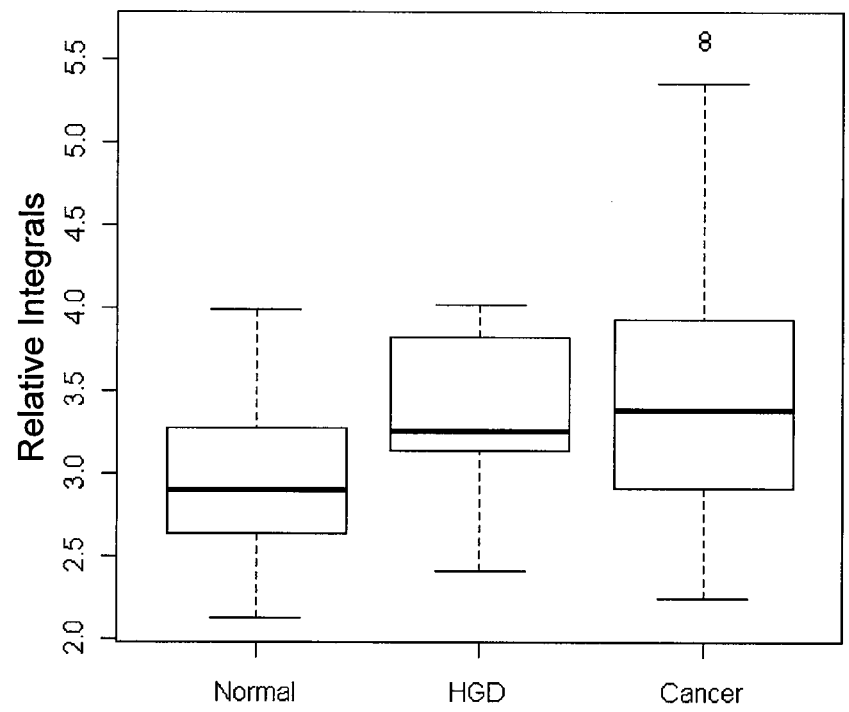

The ranges of each metabolite concentration for control, HGD, and EAC samples are shown as box- and whisker plots in FIG. 4A-FIG. 4G. The BE data were excluded from this plot because of the small number of samples. The same increasing trends of each metabolite showed in the plots from normal controls to HGD and from HGD to EAC. For citrate, creatinine, lactate, and α-glucose, the changes from normal controls to HGD were greater than the ones from HGD to EAC, which were consistent with the p-value results. FIG. 4A-FIG. 4H show box-and-whisker plots comparing the groups "Normal," "HGD" and "Cancer" for several biomarkers, in which the y axis represents the relative concentration level of each metabolite normalized by the internal standard TSP. FIG. 4A, glutamine; FIG. 4B, β-hydroxybutyrate; FIG. 4C, citrate; FIG. 4D, unknown 1; FIG. 4E, lysine; FIG. 4F, creatinine: FIG. 4G, lactate; and FIG. 4H, α-glucose.

Possible age and gender effects were also investigated among the cancer samples (Table 6, below). Large p-values (p≥0.05) were observed for comparisons between male and female patients for each of the eight markers indicating that gender is likely not a significant factor in the classification. Similarly, the p-values obtained in comparisons of younger and older patients are also high, indicating that an age effect is also not likely to be present.

TABLE 5 p-value Results For Different Group Comparisons

| metabolite | N vs BE | N vs HGD | N vs EAC | BE vs HGD | BE vs EAC | HGD vs EAC |
|---|---|---|---|---|---|---|
| glutamine | 1.38E−01 | 3.42E−01 | 3.86E−04 | 6.54E−02 | 2.07E−02 | 1.58E−01 |
| β-hydroxybutyrate | 6.62E−01 | 2.39E−02 | 3.34E−12 | 1.54E−01 | 3.08E−02 | 3.40E−01 |
| citrate | 8.95E−01 | 4.86E−03 | 1.36E−07 | 1.95E−01 | 2.00E−01 | 8.99E−01 |
| Unknown 1 | 4.39E−01 | 1.10E−02 | 4.67E−10 | 5.10E−02 | 1.42E−02 | 6.38E−02 |
| lysine | 2.36E−01 | 6.77E−02 | 1.99E−05 | 9.96E−01 | 7.80E−01 | 6.66E−01 |
| creatinine | 8.59E−01 | 2.10E−02 | 5.46E−04 | 1.05E−01 | 9.77E−02 | 9.32E−01 |
| lactate | 1.74E−01 | 8.21E−04 | 4.82E−07 | 5.29E−01 | 6.09E−01 | 5.65E−01 |
| α-glucose | 3.80E−01 | 2.95E−02 | 2.01E−06 | 5.83E−01 | 6.71E−01 | 4.08E−01 |

[a] Abbreviations: N, normal control; BE, Barrett's esophagus; HGD, high-grade dysplasia; EAC, esophageal adenocarcinoma.

TABLE 6 p-value Results For Different Genders And Ages Of EAC Patients

| metabolite | M vs F | above average age vs below average age [b] |
|---|---|---|
| glutamine | 0.494 | 0.888 |
| β-hydroxybutyrate | 0.559 | 0.329 |
| citrate | 0.063 | 0.083 |
| Unknown 1 | 0.395 | 0.935 |
| lysine | 0.327 | 0.974 |
| creatinine | 0.054 | 0.118 |
| lactate | 0.925 | 0.889 |
| α-glucose | 0.855 | 0.344 |

[a] Abbreviations: M, male patient; F, female patient.
[b] Average age of all EAC patients = 65.6 yr.

Figure 5:
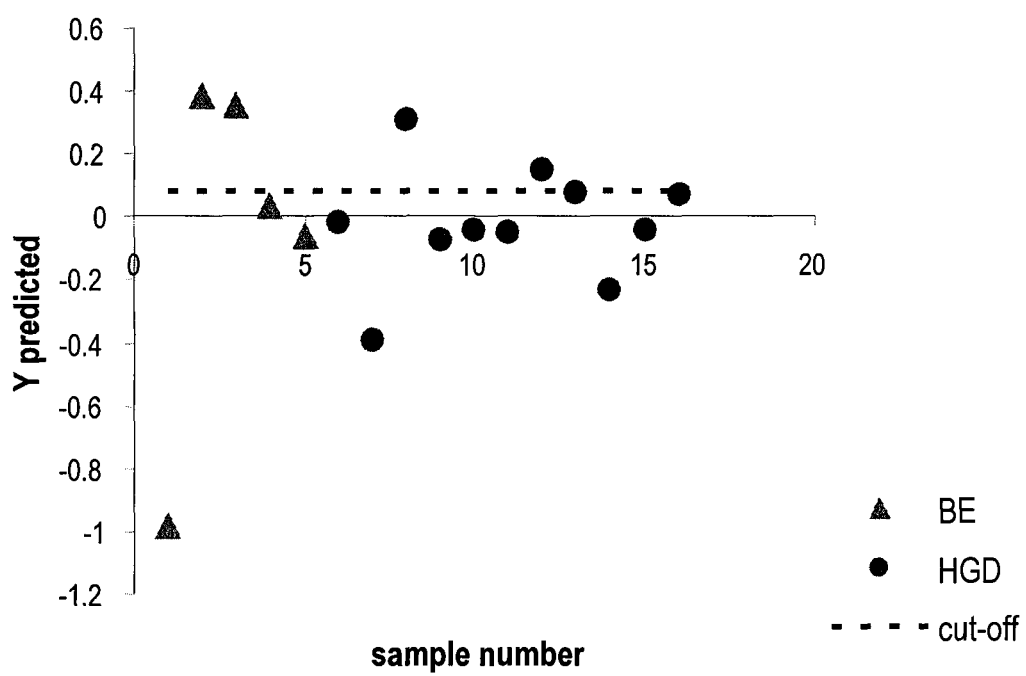
FIG. 5 shows a PLS-DA prediction from the model based on 8 metabolite markers for BE and HGD samples.

To further evaluate the BE and HGD samples, the same PLS-DA model used for predicting the control and EAC samples was applied, and the result is shown as FIG. 5. BE samples gave a mixed result, and no confident conclusion could be made because of the small number of samples, However, 9 out of 11 HGD samples were predicted as EAC in this case, which supported the previous PLS result.

A metabolomics approach based on $^1$H NMR coupled with multivariate statistical methods such as PUS, or PLS-DA, and starting with metabolite identified by employing a univariate statistical method (p-values), provides a powerful approach for metabolic profiling of blood serum to differentiate EAC patients from control subjects. The samples from EAC patients were easily distinguished from those from control subjects by PLS using auto-scaling; this approach using other scaling methods (pareto or log scaling) were not as successful. This result is explained by the contribution of a number of low intensity signals that can contribute to the classification depending on the particular seating method used. However, significant noise also contributes to the low signals that are unidentifiable by standard NMR techniques. The same model without the healthy controls failed to discriminate different ages and genders of esophageal patients, which indicates that age and gender were probably not relevant parameters in the model. The resulting model had high sensitivity and specificity for the prediction of EAC.

Figure 6:
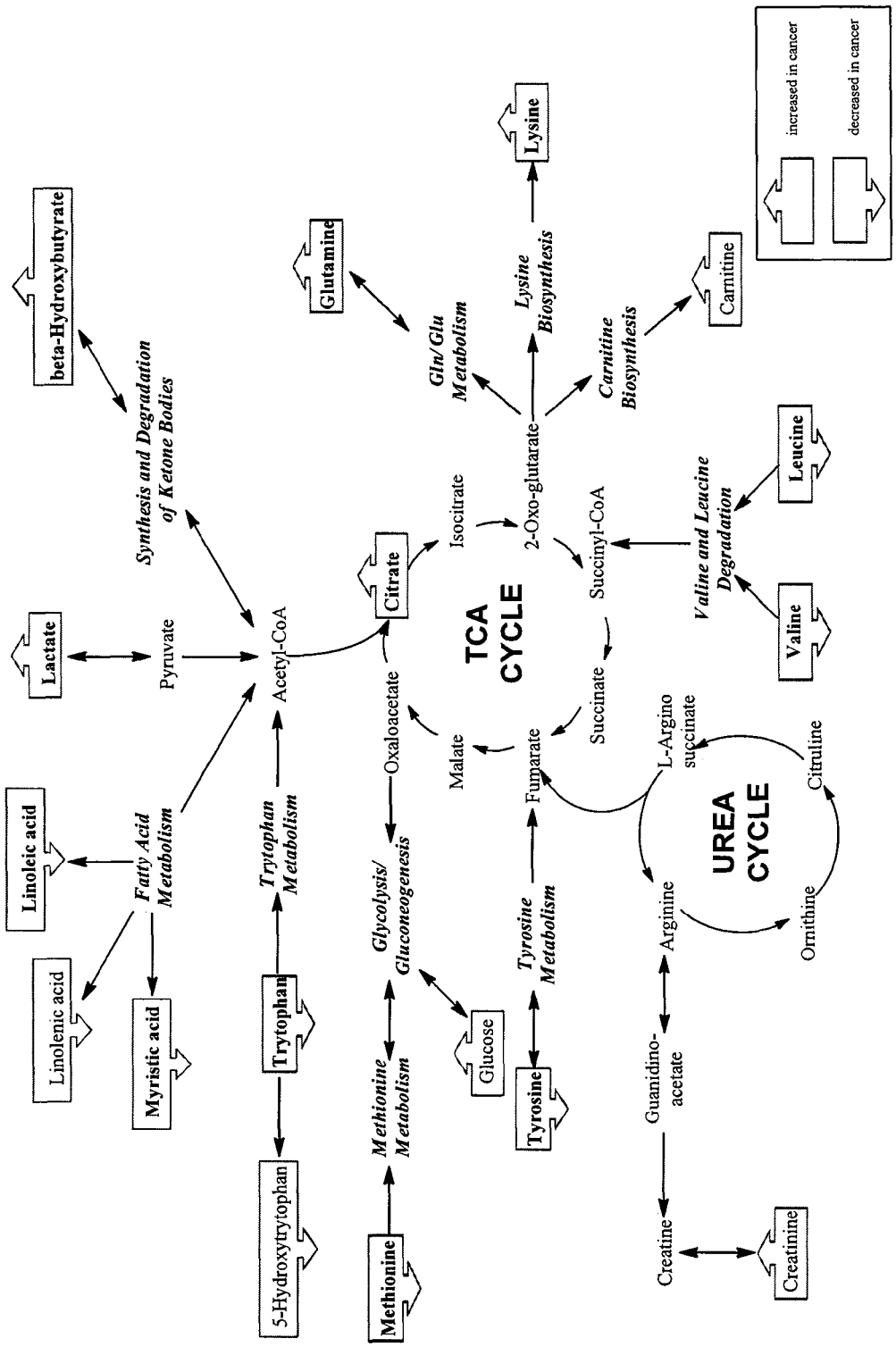
FIG. 6 shows simplified altered metabolism pathways for the most relevant metabolic differences between esophageal cancer patients and control subjects.

Altered metabolic pathways in EAC were identified based on the metabolites that showed significant concentration changes. According to the KEGG online database (http://www.genome.jp/kegg/pathway.html), a simplified pathway map is shown in FIG. 6. The up-regulation of α-glucose and lactate, a common observation in the serum of cancer subjects, was detected in samples from EAC patients. The phenomenon of cancer cells avidly taking up α-glucose and producing lactic acid under aerobic conditions was hypothesized as aerobic glycolysis by Otto Warburg in 1924. The metabolism of α-glucose with a concomitant increase of lactate production has been regarded as a common trait in many rapidly proliferating cancers. A continuous supply of α-glucose is demanded by cancer cells to produce glycoproteins, triglycerides, and glycogen, and as an important source of energy. High molar concentrations of lactate were correlated with a high incidence of distant metastasis even in an early stage of the disease. Numerous recent reports support these data by demonstrating various biological activities of lactate that can enhance the malignant behavior of cancer cells, including epithelial ovarian cancer, cervical cancer, colorectal cancer, and various primary carcinomas in head, neck and colorectal regions. Thus, α-glucose and lactate accumulation mirrors the higher energy demand of tumor malignancy. The average absolute concentration of α-glucose is above the normal range in the cancer patients; however its counterpart, lactate, is nevertheless roughly within the normal range, and thus these markers individually would not point to abnormality (Table 7, below).

TABLE 7

Absolute concentration comparison of glutamine, creatinine, lactate and α-glucose

| | Control samples | | EAC samples | | |
|---|---|---|---|---|---|
| metabolite | mean (mM) | SD [b] (mM) | mean (mM) | SD (mM) | Normal range (mM) [a] |
| glutamine | 0.469 | 0.054 | 0.515 | 0.068 | 0.502-0.670 |
| creatinine | 0.078 | 0.015 | 0.096 | 0.036 | 0.050-0.093 |
| lactate | 2.86 | 0.64 | 3.66 | 0.79 | 1.42-4.53 |
| α-glucose | 5.49 | 0.76 | 6.61 | 1.48 | 4.90-5.70 |

[a] hmdb.ca
[b] Abbreviations: SD, standard deviation.

The organic acids β-hydroxybutyrate and citrate were also found to be increased in samples from EAC patients compared to control samples. Increased amounts of β-hydroxybutyrate may be due to increased energy metabolism in the tumor, which results in large amounts of lactate produced by the tumor. When the lactate is abundant, the Cori cycle might not be able to convert lactate back to α-glucose in the liver, which results in the accumulation of Acetyl-CoA, and the citrate up-regulation in the citrate cycle (TCA cycle) sequentially. In case the Acetyl-CoA is not well accommodated by the TCA cycle, ketogenesis will take place. As a ketone body, β-hydroxybutyrate will be converted by β-hydroxybutyrate dehydrogenase, which results in the increased levels of β-hydroxybutyrate.

Increased levels of lysine, glutamine, and creatinine were also found in the serum of EAC patients. This is consistent with the effects on the TCA cycle and lactate accumulation, which provide precursors for many compounds including lysine, glutamine, and creatinine. It has been reported that the human hepatocellular carcinoma (HCC) tumors have elevated levels of glutamine compared with the non-involved adjacent liver tissues. The elevation of lysine is also in good agreement with the previous findings in the extracellular fluid of human cerebral gliomas and colon carcinoma. Creatinine levels are known to be affected by various cancers, and it was recently observed to be high in a report analyzing oral squamous cell carcinoma (OSCC) tumor samples. Nevertheless, the absolute concentrations of creatinine and glutamine were also not outside of the normal range (Table 7).

TABLE 8

Student's t-test Results For Different Group Comparisons

| | p-value | | | | |
|---|---|---|---|---|---|
| metabolite | N vs early stage EAC | N vs late stage EAC | BE vs early stage EAC | HGD vs early stage EAC | early stage EAC vs late stage EAC |
| leucine | 0.024721 | 0.313715 | 0.000662 | 0.077035 | 0.073545 |
| β-hydroxybutyrate | 0.000527 | 2.16E−07 | 0.041249 | 0.18197 | 0.502322 |
| lysine | 0.000619 | 0.000724 | 0.002146 | 0.046197 | 0.109484 |
| glutamine | 0.001395 | 0.011887 | 0.003983 | 0.031217 | 0.057081 |
| acetone | 0.037976 | 0.815539 | 0.000408 | 0.132797 | 0.036172 |
| acetoacetate | 0.007573 | 0.000492 | 0.0004 | 0.384006 | 0.351773 |
| citrate | 0.000141 | 1.58E−07 | 0.068968 | 0.46012 | 0.697529 |
| Unknown 1 | 3.64E−06 | 3.15E−09 | 0.002581 | 0.049587 | 0.992147 |
| asparagine | 0.008897 | 0.005095 | 0.030033 | 0.218311 | 0.196706 |
| creatinine | 0.026764 | 0.000858 | 0.04385 | 0.309993 | 0.135932 |
| lactate | 0.000396 | 3.25E−05 | 0.596059 | 0.541815 | 0.774796 |
| α-glucose | 0.006117 | 0.000124 | 0.748968 | 0.320462 | 0.45563 |
| unsaturated lipids | 0.287154 | 0.064584 | 0.018676 | 0.226534 | 0.036963 |
| glyceryl of lipids | 0.983398 | 0.052328 | 0.0808 | 0.534725 | 0.284288 |
| lipids C=C—CH2—C=C | 0.980695 | 0.008613 | 0.032628 | 0.455013 | 0.079069 |
| lipids CH2—CO | 0.314499 | 0.037364 | 0.018141 | 0.319495 | 0.036615 |
| lipids CH2—C=C | 0.327037 | 0.232227 | 0.035629 | 0.227064 | 0.100514 |
| lipids CH2—CH2—C=C | 0.223241 | 0.105682 | 0.185913 | 0.886248 | 0.996133 |
| lipids CH2—CH2—CO | 0.393791 | 0.021347 | 0.022544 | 0.285191 | 0.043763 |
| VLDL2/LDL2 | 0.269359 | 0.085373 | 0.048201 | 0.280174 | 0.054369 |
| VLDL1/LDL1 | 0.522948 | 0.021897 | 0.074804 | 0.440976 | 0.081535 |

[1] Abbreviations: N, control sample; BE, Barrett's esophagus; HGD, high-grade dysplasia; C, EAC.

Student's t-test results of comparisons of different combinations of normal control, BE, HGD, early stage EAC and late stage EAC samples are listed in Table 8, above. Twelve metabolites, including leucine, acetone, acetoacetate, asparagine, α-glucose, lactate, citrate, β-hydroxybutyrate, lysine, glutamine, creatinine, and unknown 1, show significant level change between normal control samples and early stage EAC samples. However, compared to the early stage EAC samples, the levels of these metabolites do not change too much in the late stage EAC samples.

Figure 7A:
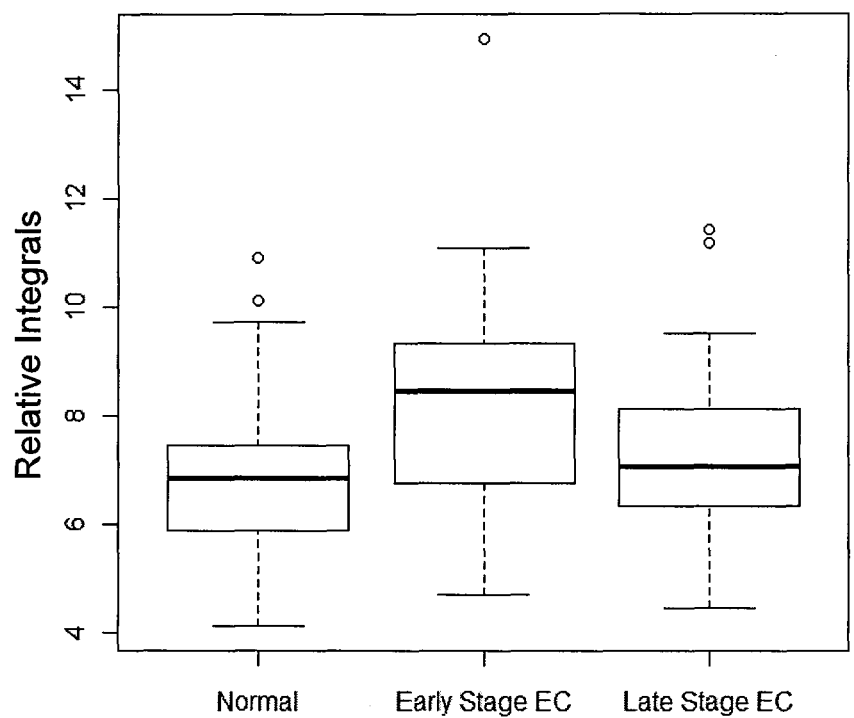
FIG. 7A-FIG. 7S show box-and-whisker plots comparing the groups "Normal," "Early Stage EC" and "Late Stage EC" for several biomarkers, in which the y axis for each plot indicates the relative concentration level of each metabolite normalized by the internal standard TSP.
Figure 7B:
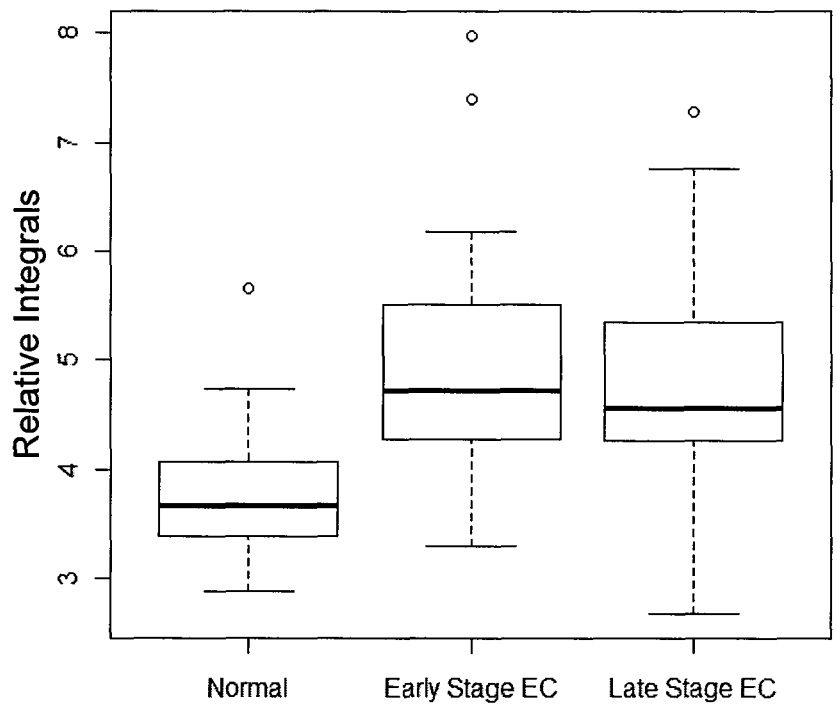
FIG. 7B, β-hydroxybutyrate.
Figure 7C:
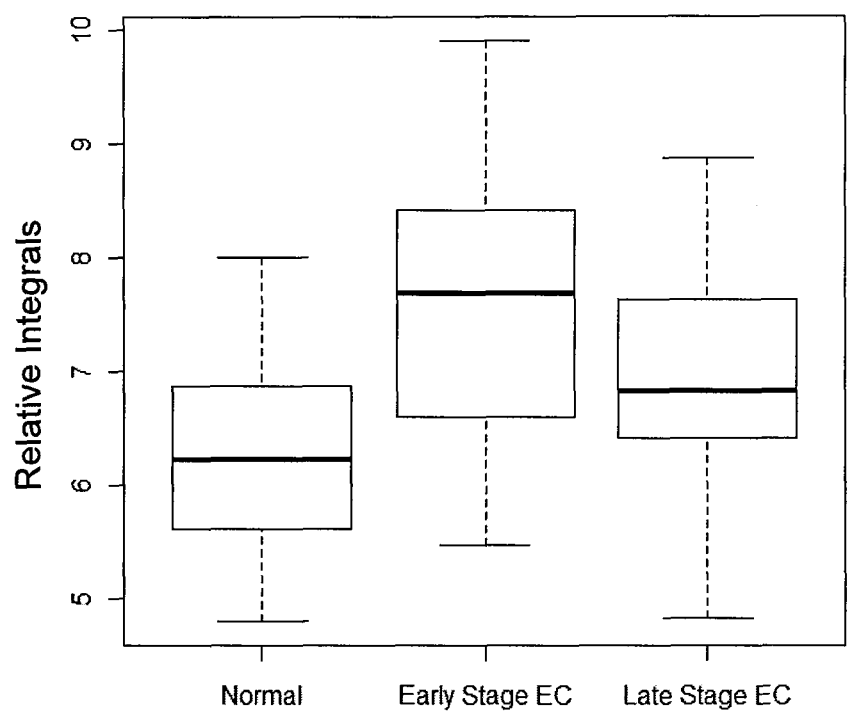
FIG. 7C, lysine.
Figure 7D:
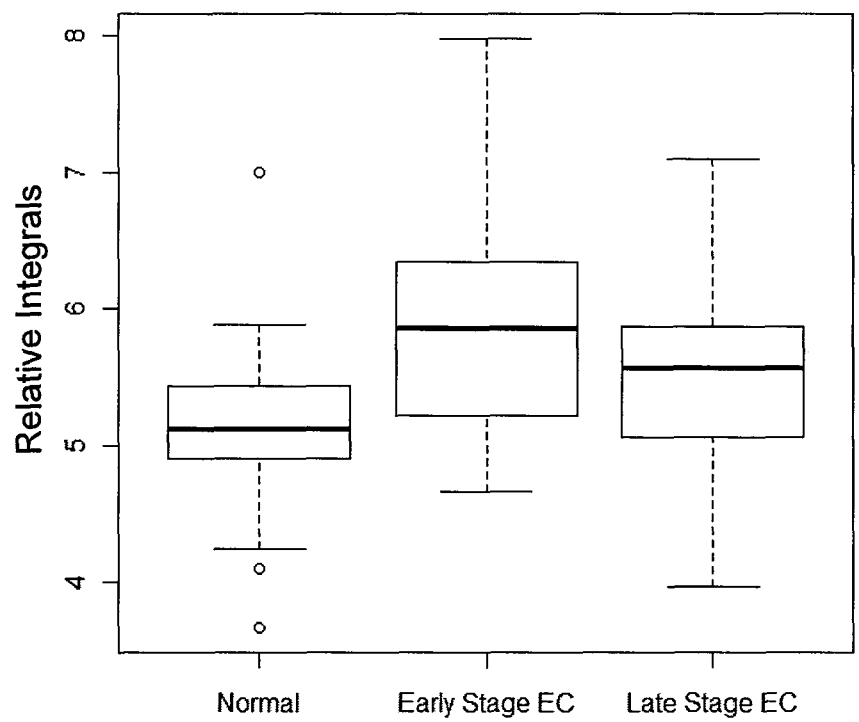
FIG. 7D, glutamine.
Figure 7E:
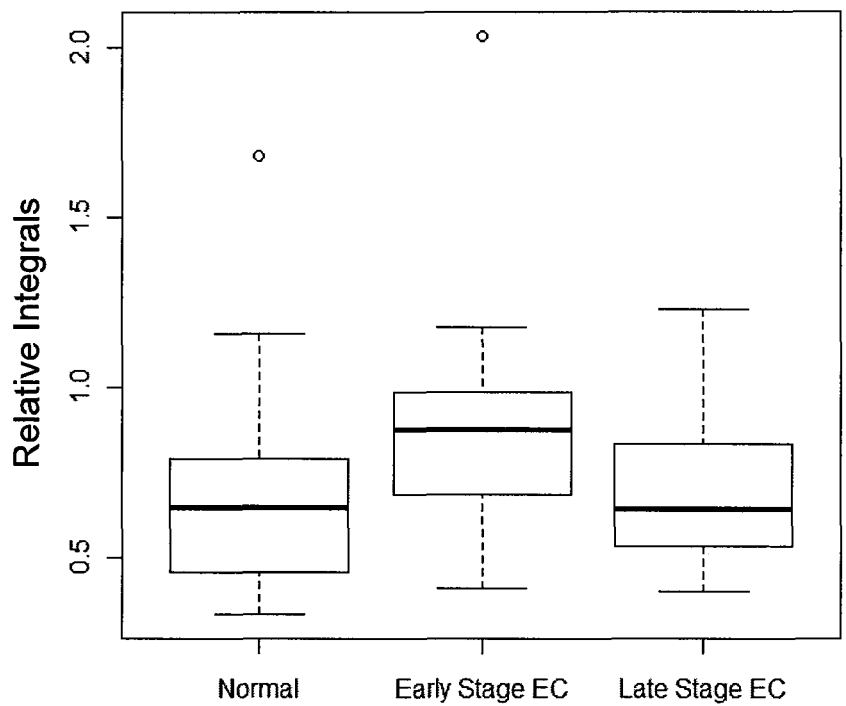
FIG. 7E, acetone.
Figure 7F:
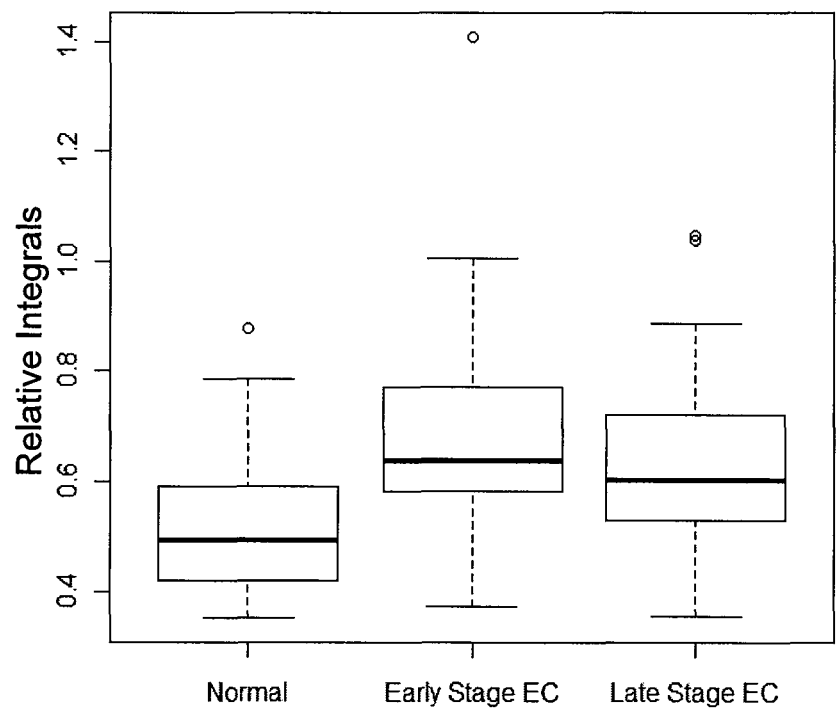
FIG. 7F, acetoacetate.
Figure 7G:
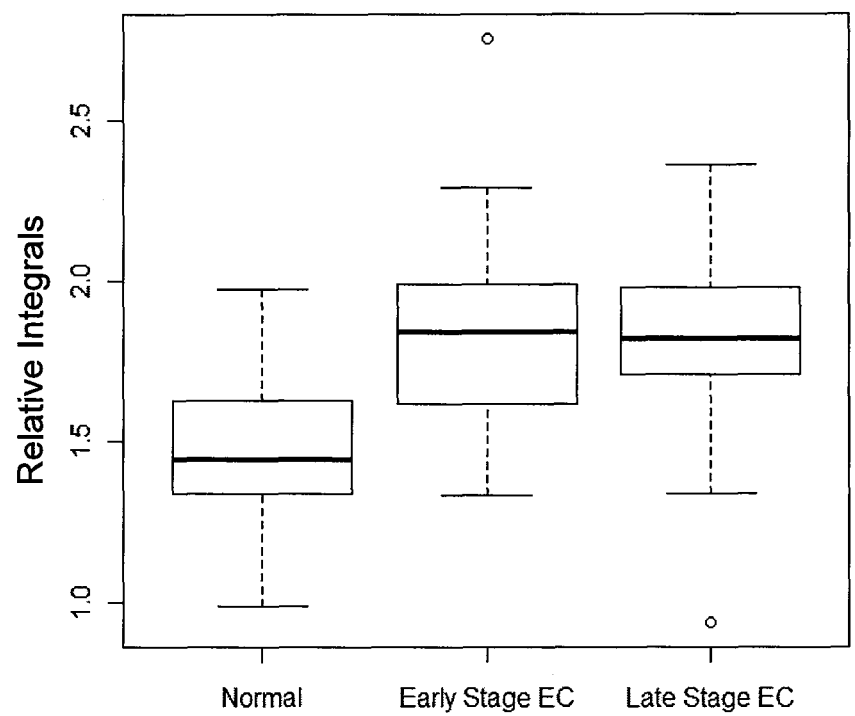
FIG. 7G, citrate.
Figure 7H:
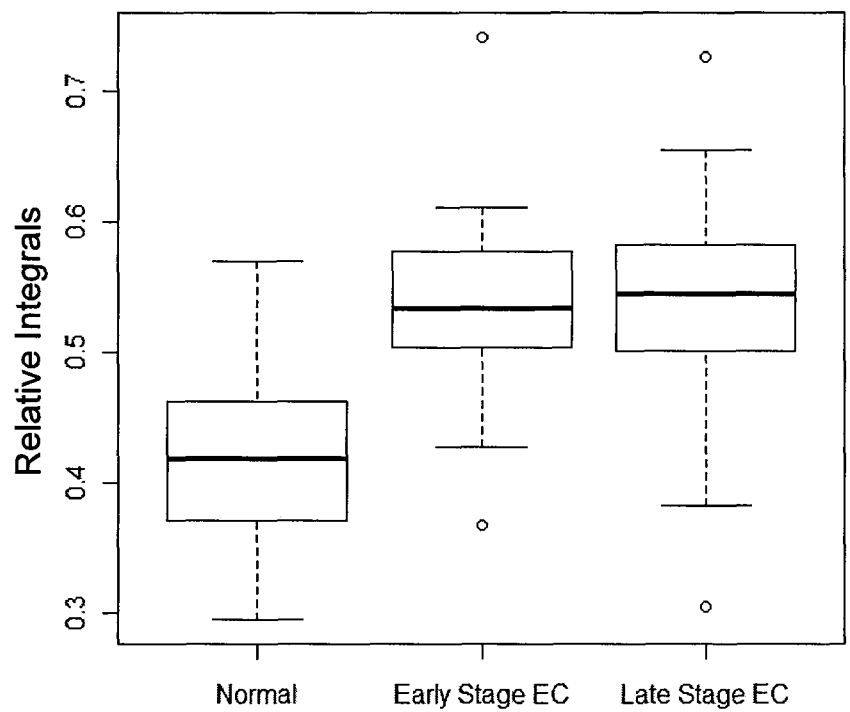
FIG. 7H, unknown 1.
Figure 7I:
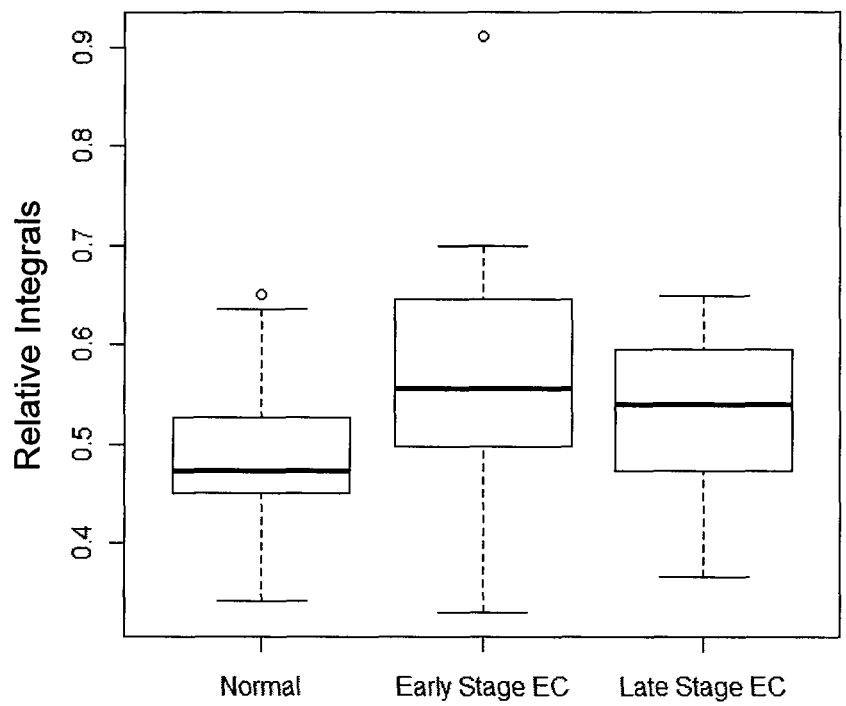
FIG. 7I, asparagine.
Figure 7J:
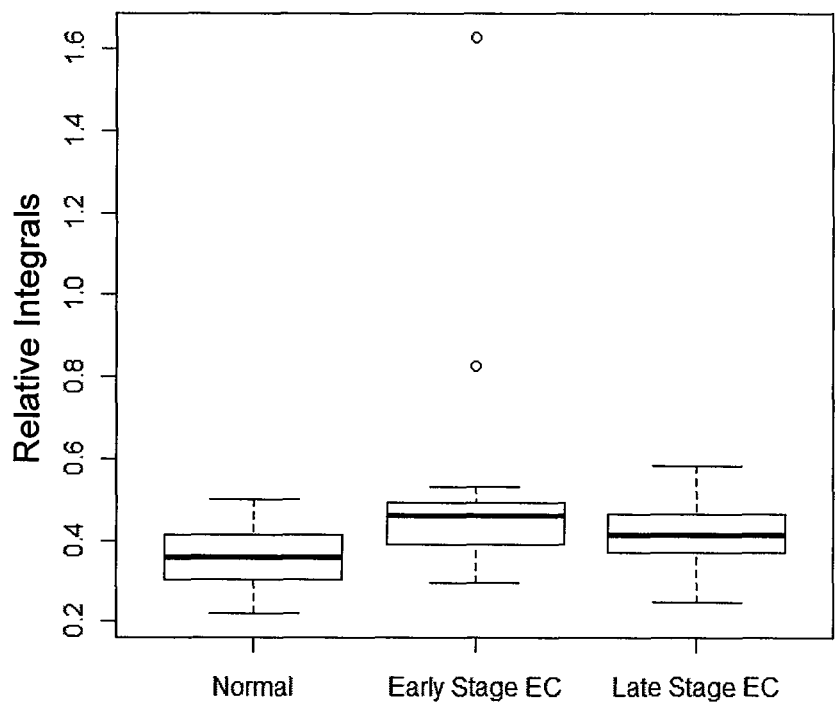
FIG. 7J, creatinine FIG. 7K, lactate.
Figure 7K:
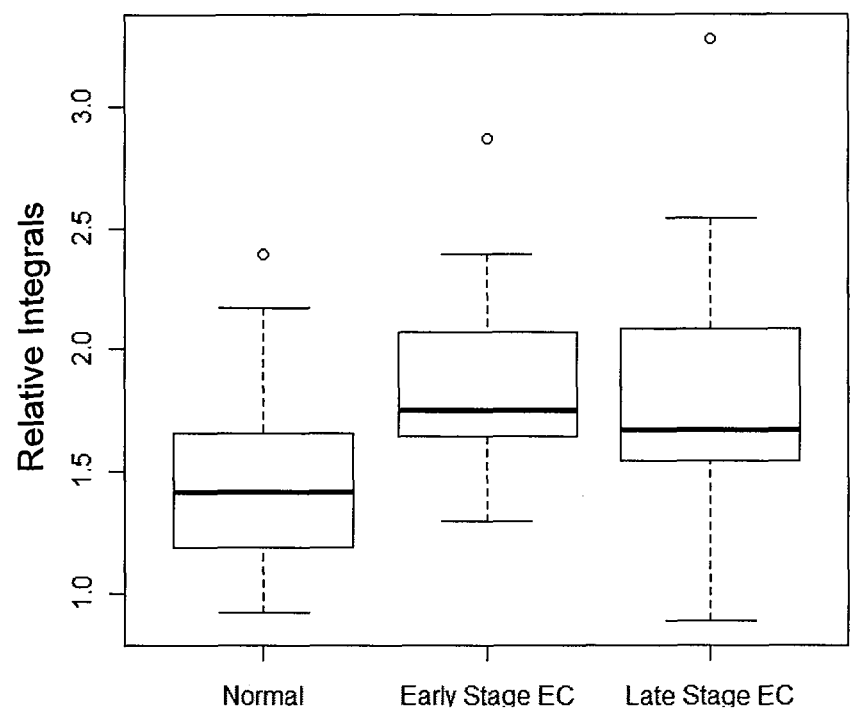
FIG. 7L, α-glucose.
FIG. 7M, VLDL1/LDL1.
FIG. 7N, VLDL2/LDL2.
FIG. 7O, lipids CH2-CH2-CO.
FIG. 7P, lipids CH2-C=C.
FIG. 7Q, lipids CH2-CO.
FIG. 7R, lipids C=C—CH2-C=C.
Figure 7L:
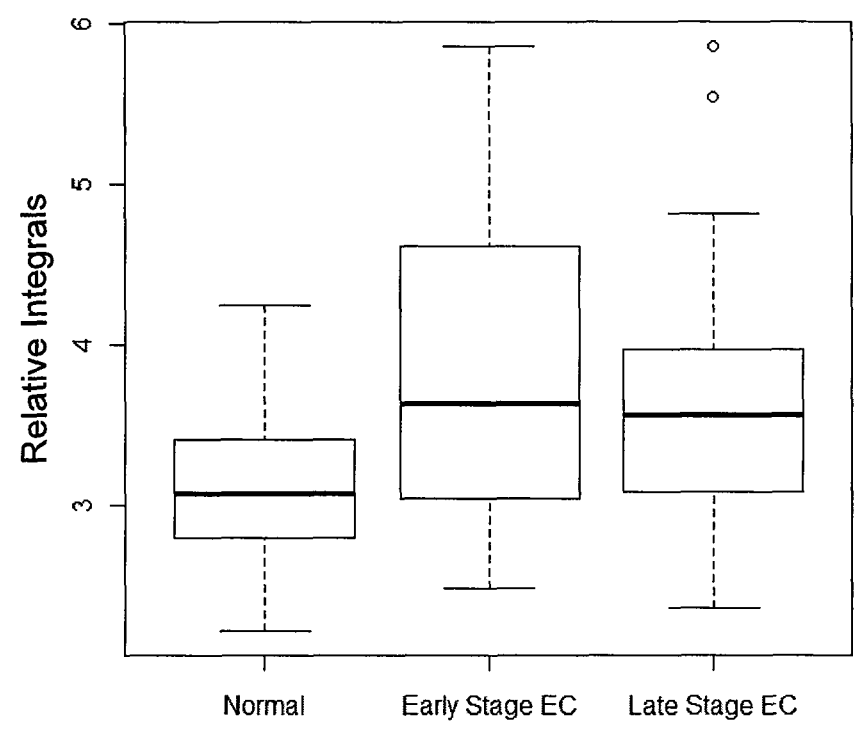
Figure 7M:
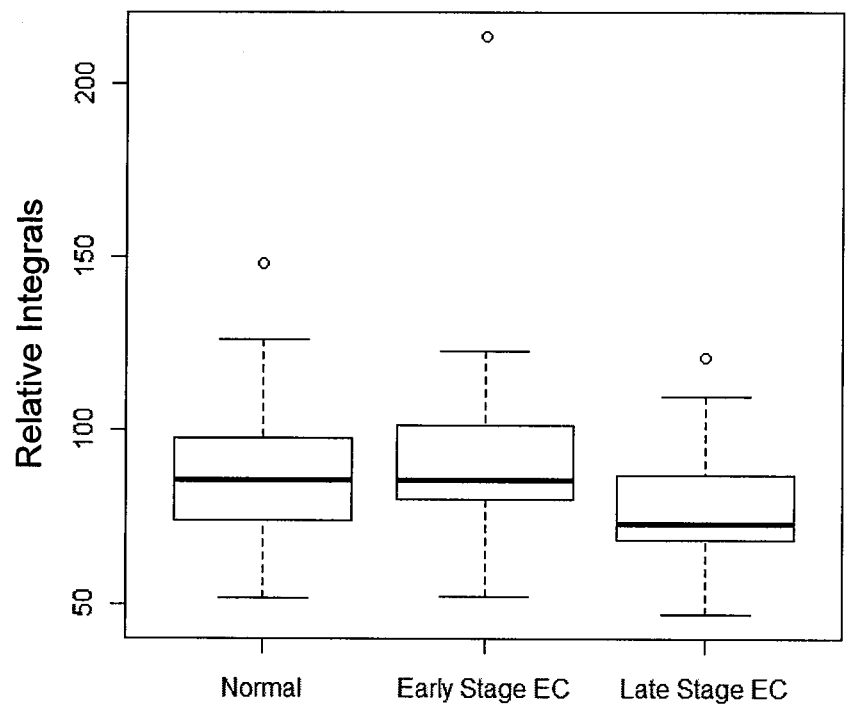
Figure 7N:
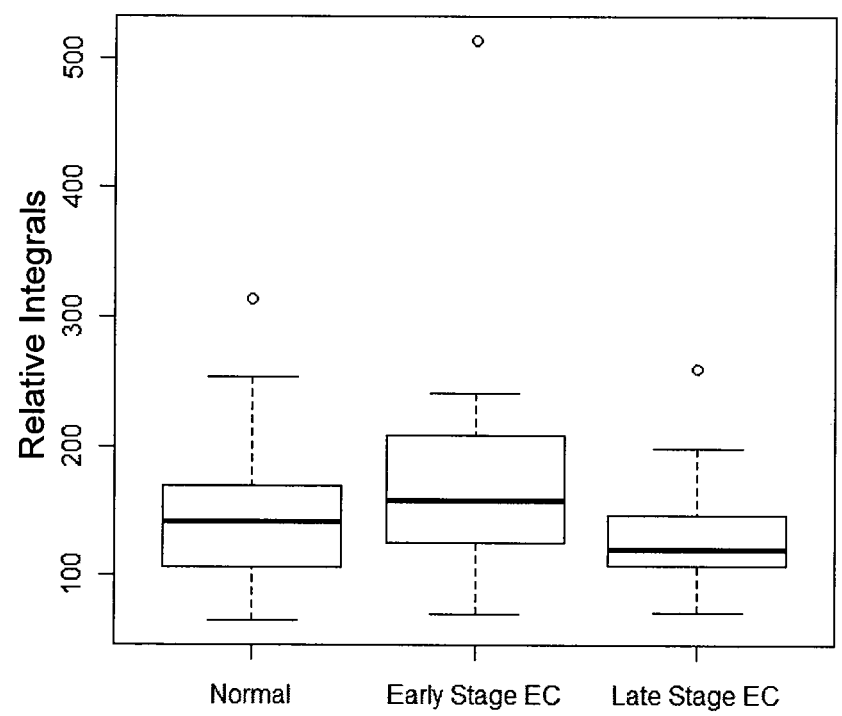
Figure 7O:
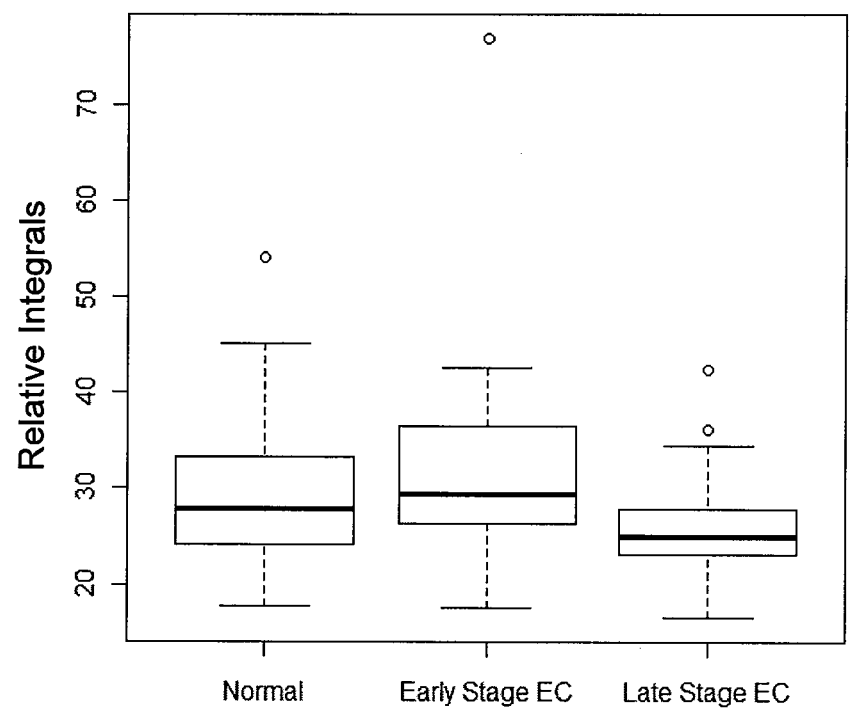
Figure 7P:
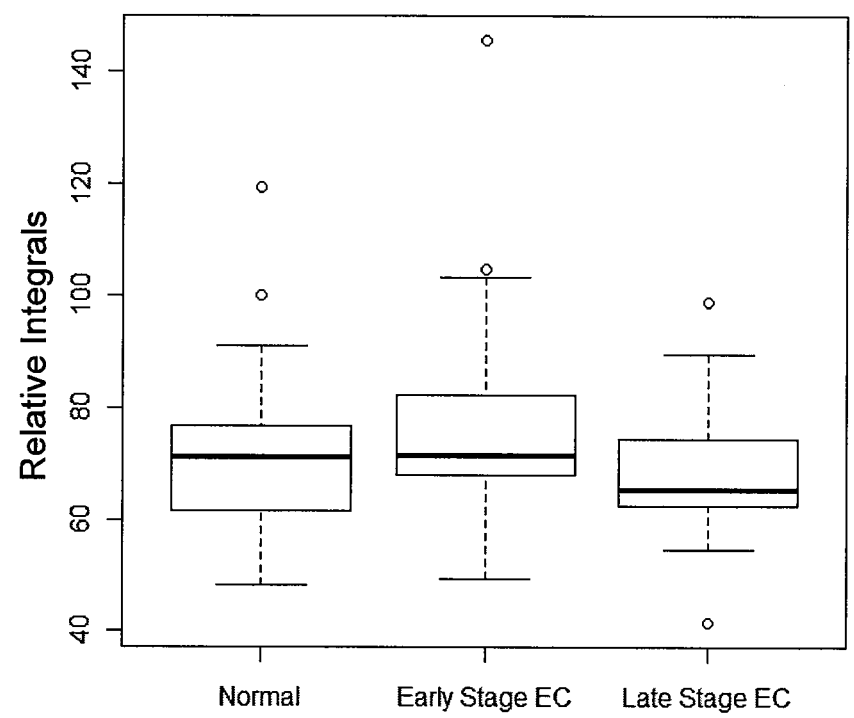
Figure 7Q:
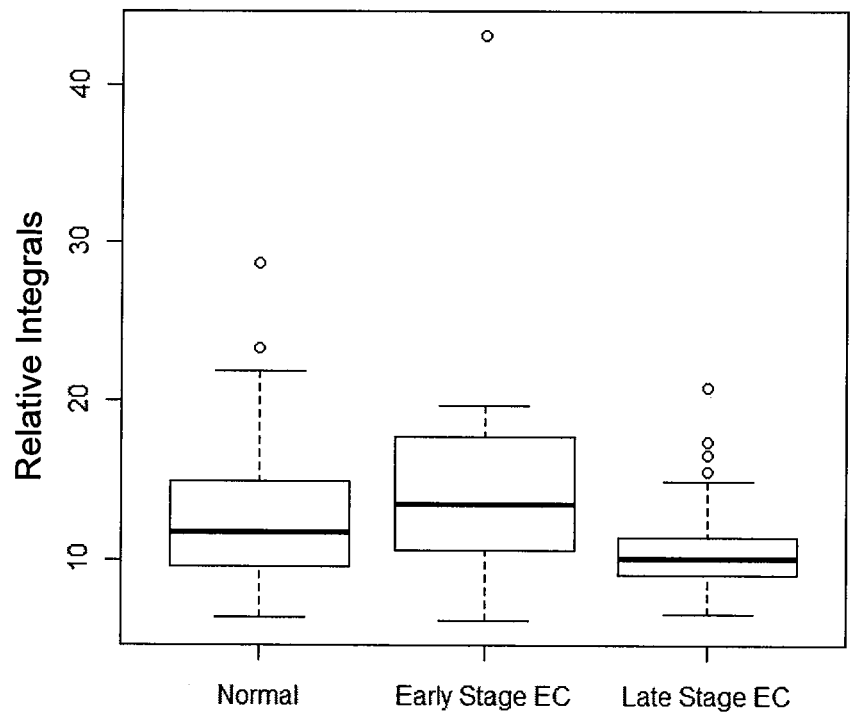
Figure 7R:
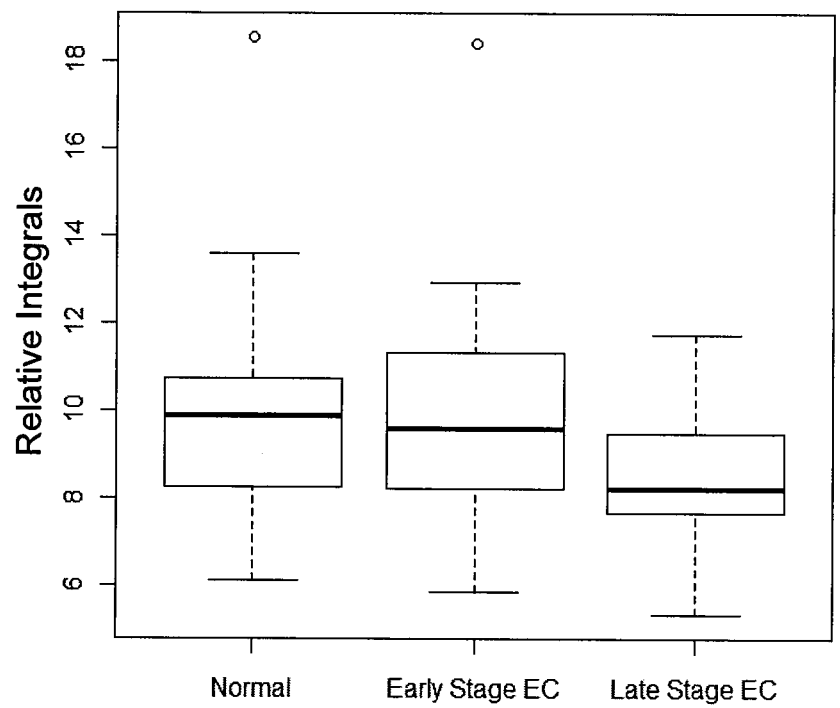
Figure 7S:
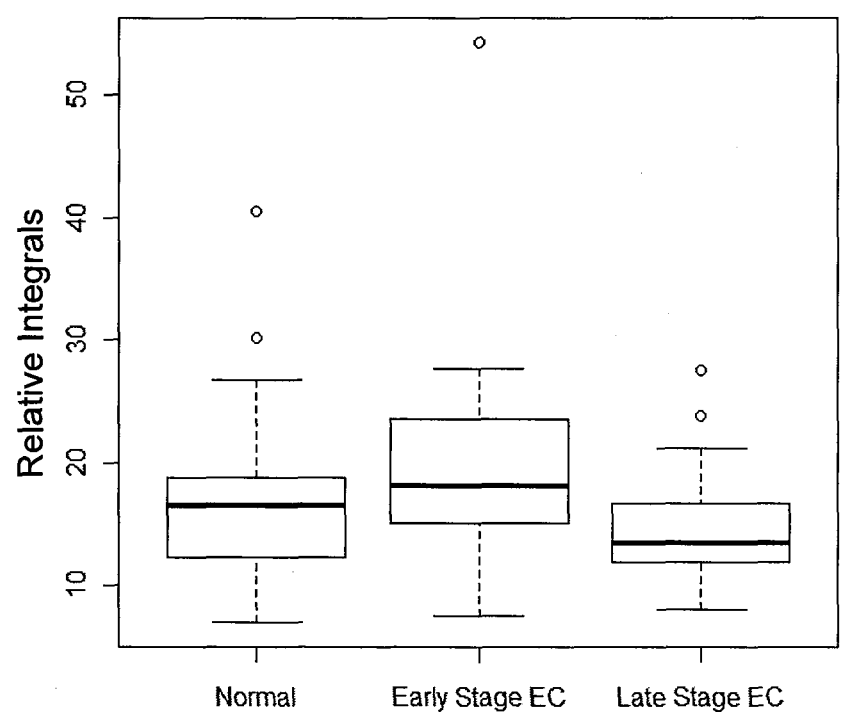

The ranges of the concentration of each metabolite biomarker for control, early stage EAC and late stage EAC samples are shown as box-and-whisker plots in FIG. 7A-FIG. 7S. The comparisons are consistent with the t-test results. FIG. 7A-FIG. 7S show box-and-whisker plots comparing the groups "Normal," "Early Stage EC" and "Late Stage EC" for several biomarkers, in which the y axis represents the relative concentration level of each metabolite normalized by the internal standard TSP. FIG. 7A, leucine; FIG. 7B, β-hydroxybutyrate; FIG. 7C, lysine; FIG. 7D, glutamine; FIG. 7E, acetone; FIG. 7F, acetoacetate; FIG. 7G, citrate; FIG. 7H, unknown 1; FIG. 7I, asparagine; FIG. 7J, creatinine: FIG. 7K, lactate; FIG. 7L, α-glucose; FIG. 7M, VLDL1/LDL1; FIG. 7N, VLDL2/LDL2; FIG. 7O, lipids $CH_2$—$CH_2$—CO; FIG. 7P, lipids $CH_2$—C=C; FIG. 7Q, lipids $CH_2$—CO; FIG. 7R, lipids C=C—$CH_2$—C=C; and FIG. 7S, unsaturated lipids. The box-and-whisker plots in FIG. 7M-FIG. 7S show that lipid levels increased a little in the EAC early stage, and dropped down significantly in late stage.

Example 2

The LC-MS spectrum for each serum sample consisted of more than 5000 features of which nearly 1400 peaks were assigned to metabolites using the Agilent database. Peaks from the spectra that were missing in more than 10% of the samples from any group were omitted from further analysis. The use of this filter and the Agilent chemical library resulted in a total of approximately 200 identified metabolites common to all the groups. These identified metabolites were analyzed using univariate analysis. The results showed that 40 metabolites varied significantly (p<0.05) between either EAC and normal controls, EAC and high-risk patients (BE and HGD patients), or high-risk patients and normal controls. Thirteen of these metabolites could be verified from the mass spectra and retention times of the authentic commercial compounds.

Table 9 lists the verified metabolites from LC-MS along with their formulae, masses and retention times. Similarly, as shown in Table 10, fifteen patient-class differentiating metabolites with low p-values (p<0.05) obtained by integrating the relevant NMR peaks were confirmed by matching the observed chemical shifts and multiplicities with the results of Example 1.

TABLE 9

Identification information for Metabolites detected using LC-MS

| Compound Name | Formula | m/z Calculated (Da) | m/z Detected (Da) | Delta m/z (ppm) | RT Authentic Pooled (min) | RT Detected (min) | Delta RT (min) |
|---|---|---|---|---|---|---|---|
| lactic acid | $C_3H_6O_3$ | 90.0317 | 90.0318 | −1.1774 | 0.51 | 0.49 | 0.02 |
| valine | $C_5H_{11}NO_2$ | 117.0790 | 117.0790 | 0 | 0.38 | 0.42 | −0.04 |
| pyroglutamic acid | $C_5H_7NO_3$ | 129.0426 | 129.0429 | −2.4023 | 0.56 | 0.55 | 0.01 |
| leucine | $C_6H_{13}NO_2$ | 131.0946 | 131.0944 | 1.7468 | 0.59 | 0.62 | −0.03 |
| methionine | $C_5H_{11}NO_2S$ | 149.0511 | 149.0514 | −2.3482 | 0.41 | 0.47 | −0.06 |

TABLE 9-continued

Identification information for Metabolites detected using LC-MS

| Compound Name | Formula | m/z Calculated (Da) | m/z Detected (Da) | Delta m/z (ppm) | RT Authentic Pooled (min) | RT Detected (min) | Delta RT (min) |
|---|---|---|---|---|---|---|---|
| carnitine | $C_7H_{15}NO_3$ | 161.1052 | 161.1049 | 1.8001 | 0.33 | 0.37 | −0.04 |
| tyrosine | $C_9H_{11}NO_3$ | 181.0739 | 181.0734 | 2.7061 | 0.49 | 0.51 | −0.02 |
| tryptophan | $C_{11}H_{12}N_2O_2$ | 204.0899 | 204.0898 | 0.3920 | 1.38 | 1.43 | −0.05 |
| 5-hydroxytryptophan | $C_{11}H_{12}N_2O_3$ | 220.0848 | 220.0852 | −1.8629 | 0.64 | 0.71 | −0.07 |
| myristic acid | $C_{14}H_{28}O_2$ | 228.2089 | 228.2092 | −1.1831 | 12.34 | 12.36 | −0.02 |
| margaric acid | $C_{17}H_{34}O_2$ | 270.2559 | 270.2562 | −1.1841 | 12.93 | 12.95 | −0.02 |
| linolenic acid | $C_{18}H_{30}O_2$ | 278.2246 | 278.2252 | −2.2284 | 11.29 | 11.33 | −0.04 |
| linoleic acid | $C_{18}H_{32}O_2$ | 280.2402 | 280.2405 | −0.9635 | 12.71 | 12.75 | −0.04 |

TABLE 10

Identification information for Metabolites detected using NMR

| chemical shift (ppm)[a] | multiplicity[b] | assignment |
|---|---|---|
| 1.48 | d | alanine |
| 2.02 | s | N-acetylated protein |
| 2.09 | m | glutamine |
| 2.39 | m | β-hydroxybutyrate |
| 2.44 | m | glutamate |
| 2.53 | d | citrate |
| 2.63 | m | Unknown 1[c] |
| 2.91 | m | Unknown 2[d] |
| 3.00 | t | lysine |
| 3.35 | m | proline |
| 4.05 | s | creatinine |
| 4.11 | q | lactate |
| 5.22 | d | α-glucose |
| 7.03 | s | histidine |
| 7.18 | d | tyrosine |

[a,b]The chemical shift and multiplicity are NMR-dependent quantities that indicate the spectral peak position and number of peaks, respectively, and allow the spectroscopist to identify the chemical compound (s = singlet; d = doublet; t = triplet; q = quartet; m = complex multiplet).
[c]Unknown 1 was discovered by comparing the control group with EAC patients as reported in Example 1.
[d]Unknown 2 was discovered by comparing the normal subjects with BE and HGD patients.

The summary of the verified metabolite biomarker candidates from LC-MS and NMR with their p-values and fold changes are shown in Table 11. The sensitivity, specificity and AUROC values from the PLS-DA models of each comparison are listed in Table 12. Comparison of MS and NMR data using statistical analysis, separately, showed no significant differences due to gender, age or cancer stage.

Table 1it lists 26 measured compounds that the present studies have found to differ in concentration at the p<0.05 level for the three comparisons, Control vs. EAC, EAC vs, High-risk (BE+HEM), and Control vs. High-risk (BE+HGD). The compounds are lactic acid, leucine, methionine, carnitine, tyrosine, tryptophan, 5-hydroxytryptophan, myristic acid, margaric acid, linolenic acid, linoleic acid, pyroglutamic acid, glutamine, β-hydroxybutyrate, citrate, unknown compound 1 appearing at 2.63 ppm, lysine, creatinine, α-glucose, N-acetylated protein, proline, histidine, alanine, glutamate, and unknown compound 2 appearing at 2.91 ppm. Panels of metabolic biomarkers at the p<0.05 level range in size from 5 metabolic biomarkers for the Control vs. High-risk (BE+HGD) comparison (three of which have been identified to date: lactic acid, proline and pyroglutamic acid) to 18 identified metabolic biomarkers for the Control vs. EAC comparison.

TABLE 11

Differentiating metabolites among EAC, high-risk (BE + HGD) and control groups.

| Metabolite | Detection | Control vs EAC | | EAC vs High-risk (BE + HGD) | | Control vs High risk (BE + HGD) | |
|---|---|---|---|---|---|---|---|
| | | p-value[a] | FC[b] | p-value[a] | FC[b] | p-value[a] | FC[b] |
| lactic acid | LC-MS | 1.2E−07 | 1.6 | 3.4E−02 | 1.6 | | |
| | NMR | 2.7E−03 | 1.3 | | | 1.6E−02 | 1.4 |
| valine | LC-MS | 2.9E−07 | −1.6 | 1.0E−02 | 1.6 | | |
| | NMR | | | 3.7E−02 | 1.2 | | |
| leucine | LC-MS | 2.7E−07 | −1.2 | 4.2E−02 | 1.2 | | |
| methionine | LC-MS | 2.0E−05 | −1.6 | 2.4E−02 | −1.6 | | |
| carnitine | LC-MS | 5.7E−05 | 1.2 | | | | |
| tyrosine | LC-MS | 4.0E−03 | −1.1 | | | | |
| | NMR | | | 3.7E−02 | 1.2 | | |
| tryptophan | LC-MS | 3.2E−05 | −1.2 | | | | |
| 5-hydroxytryptophan | LC-MS | 2.6E−02 | −1.1 | | | | |
| myristic acid | LC-MS | 1.2E−03 | −1.4 | 1.8E−02 | −1.4 | | |
| margaric acid | LC-MS | 9.5E−03 | 1.3 | | | | |
| linolenic acid | LC-MS | 1.5E−02 | −1.4 | 4.3E−02 | −1.2 | | |
| linoleic add | LC-MS | 1.1E−04 | −1.5 | | | | |
| pyroglutamic acid | LC-MS | | | 9.2E−06 | 2.0 | 1.4E−04 | −2.2 |
| glutamine | NMR | 3.0E−02 | 1.1 | | | | |
| β-hydroxybutyrate | NMR | 2.3E−05 | 1.3 | | | | |
| citrate | NMR | 3.3E−04 | 1.3 | | | | |
| Unknown 1 | NMR | 3.0E−05 | 1.3 | | | | |
| lysine | NMR | 9.6E−04 | 1.1 | 2.8E−02 | 1.2 | | |
| creatinine | NMR | 2.2E−02 | 1.2 | | | | |

TABLE 11-continued

Differentiating metabolites among EAC, high-risk (BE + HGD) and control groups.

| Metabolite | Detection | Control vs EAC p-value[a] | FC[b] | EAC vs High-risk (BE + HGD) p-value[a] | FC[b] | Control vs High risk (BE + HGD) p-value[a] | FC[b] |
|---|---|---|---|---|---|---|---|
| α-glucose | NMR | 1.5E−04 | 1.2 | | | | |
| N-acetylated protein | NMR | | | 6.4E−04 | 1.2 | 3.7E−02 | −1.1 |
| proline | NMR | | | 3.1E−03 | −2.7 | 1.3E−02 | 2.1 |
| histidine | NMR | | | 7.4E−03 | 1.3 | | |
| alanine | NMR | | | 9.2E−03 | 1.3 | | |
| glutamate | NMR | | | 3.6E−02 | 1.2 | | |
| Unknown 2 | NMR | | | | | 1.4E−02 | −1.5 |

[a]p-value determined from Student's t-test;
[b]FC: fold change between esophageal adenocarcinoma (EAC) and normal controls.
Positive sign indicates a higher level in EAC and a negative value indicates a lower level.

TABLE 12

Comparison of sensitivity, specificity and AUROC values from different PLS-DA models using differentiating metabolites detected individually by NMR or MS and their combination.

| Comparison | Number of candidate markers MS | NMR | Sensitivity | Specificity | AUROC |
|---|---|---|---|---|---|
| Control vs EAC | 12 | — | 77% | 86% | 0.82 |
|  | — | 8 | 82% | 88% | 0.86 |
|  | 12 | 8 | 91% | 91% | 0.95 |
|  | 8 | 4 | 89% | 90% | 0.92 |
| EAC vs High-risk (BE + HGD) | 7 | — | 83% | 80% | 0.87 |
|  | — | 8 | 77% | 77% | 0.72 |
|  | 7 | 8 | 67% | 97% | 0.82 |
|  | 8 | 4 | 75% | 70% | 0.78 |
| Control vs High-risk (BE + HGD) | 1 | — | 74% | 75% | 0.76 |
|  | — | 4 | 68% | 92% | 0.80 |
|  | 1 | 4 | 65% | 92% | 0.80 |

Comparing Metabolic Profiles Between EAC Patients and Normal Controls:

As shown in Table 11, twelve metabolite biomarker candidates detected by LC-MS and confirmed with authentic compounds differentiated EAC patients and normal controls. FIG. 12A-FIG. 12J show the box-and-whisker plots for the peak intensities of the twelve differentiating biomarker candidates. As seen in Table 11 and FIG. 12A-FIG. 12J, the levels of lactic acid, carnitine and margaric acid were higher, and those of valine, leucine, methionine, tyrosine, tryptophan, 5-hydroxytryptophan, myristic acid, linolenic acid and linoleic acid were lower in EAC patients compared to normal controls.

The biomarker candidates from $^1$H NMR analysis have been reported in Example 1. The concentration of eight metabolites, β-hydroxybutyrate, lysine, glutamine, citrate, creatinine, lactate, α-glucose and an unknown molecule was higher in EAC specimens than in control samples, and the difference was statistically significant at the p<0.05 level (Table 11).

Comparison of Metabolic Profiles from Normal Controls with Those from EAC Patients:

FIG. 8A-FIG. 8I show results of the comparison of performance of metabolic profiles between EAC patients and normal controls. A PLS-DA model using the twelve LC-MS derived metabolites (and leave-one-out cross valuation) provided 77% sensitivity and 86% specificity with an AUROC of 0.82. Similar analysis using the eight NMR-derived metabolites provided 82% sensitivity and 88% specificity with an AUROC of 0.86. However, when the metabolite data were analyzed combining the 12 metabolite biomarkers detected using LC-MS and the 8 metabolite biomarkers detected using NMR, both the sensitivity and the specificity of the model improved to 91%, with an AUROC of 0.95.

Figure 8A:
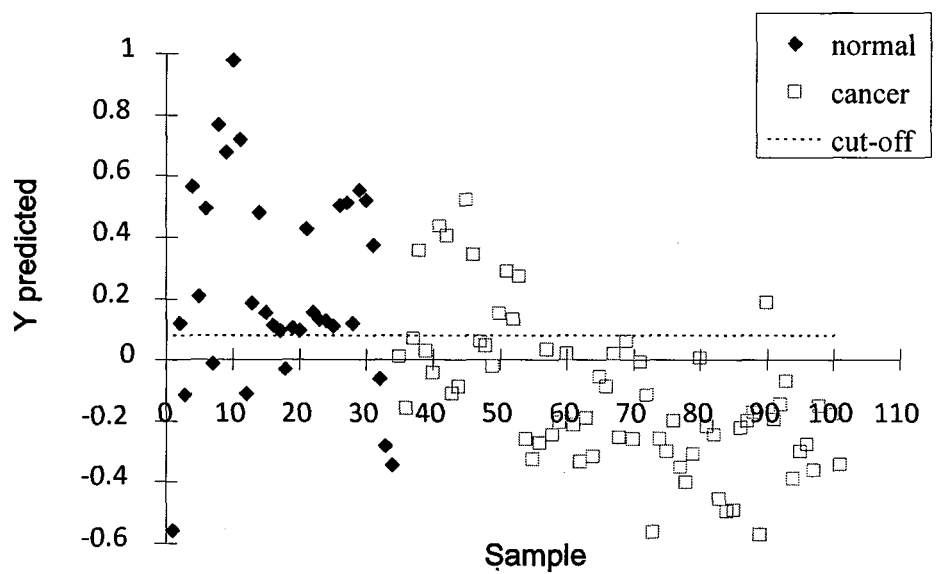
FIG. 8A-FIG. 8I show the results of a performance comparison of metabolic profiles from EAC patients and those from normal controls.
Figure 8B:
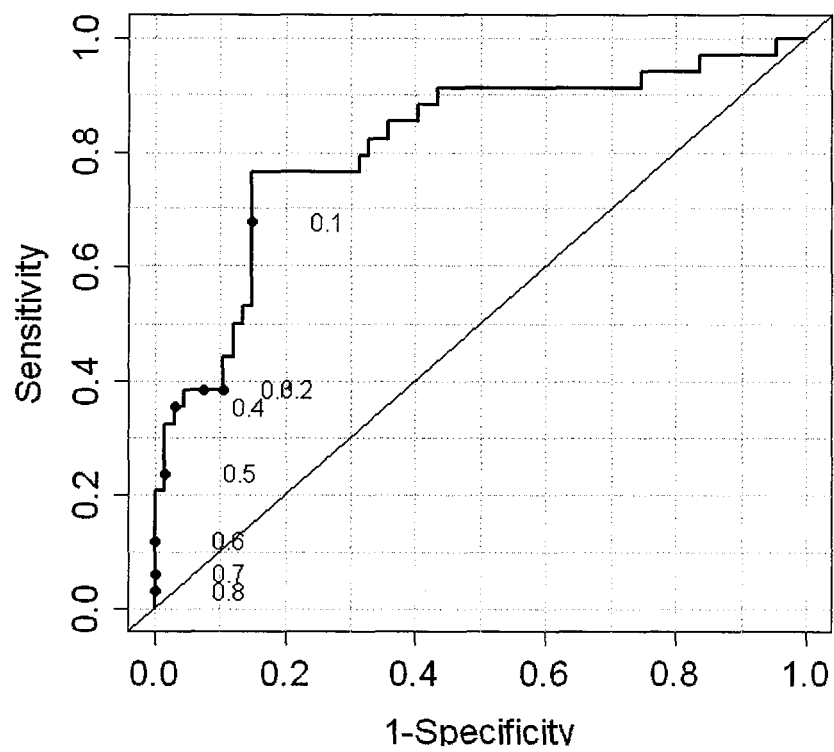
Figure 8C:
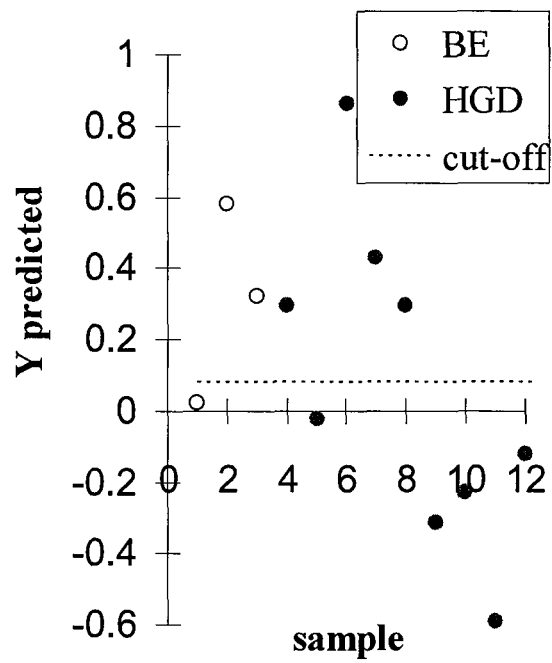

FIG. 8A shows the results of the PLS-DA model from the 12 metabolite markers from LC-MS analyses; FIG. 8B shows the ROC curve using the cross-validated predicted class values (AUROC=0.82). FIG. 8C shows the PLS-DA prediction of BE and HGD samples from the LC-MS model comparing EAC and normal controls. The BE samples gave a mixed result, and no confident conclusion could be made because of the small number of samples. However, most (⅝) of the HGD samples were below the cutoff, and would be predicted as similar to EAC samples in this case.

Figure 8D:
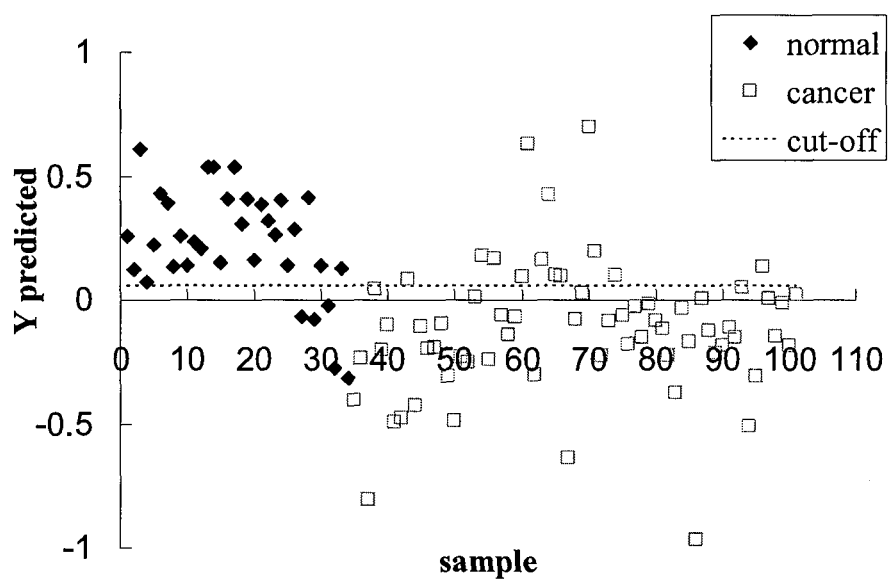
Figure 8E:
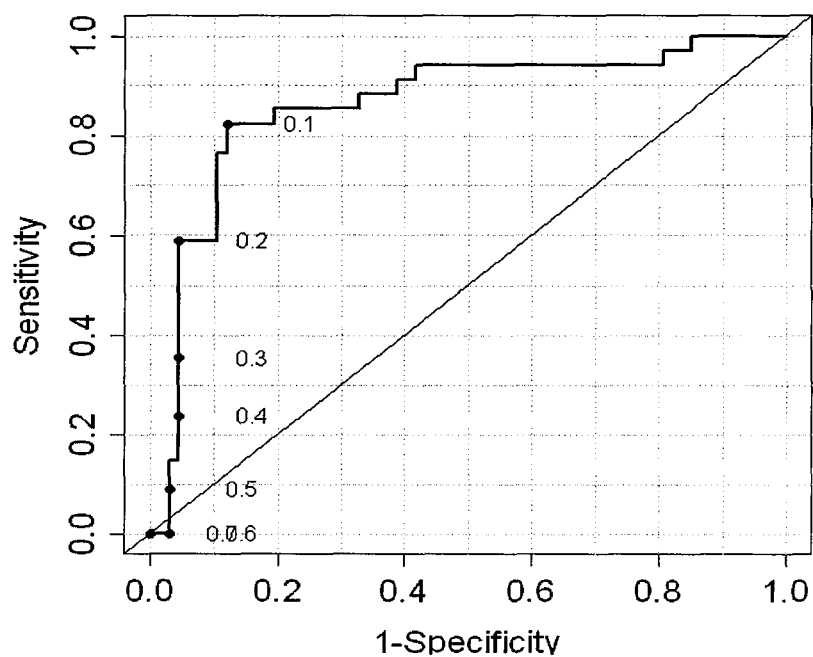
Figure 8F:
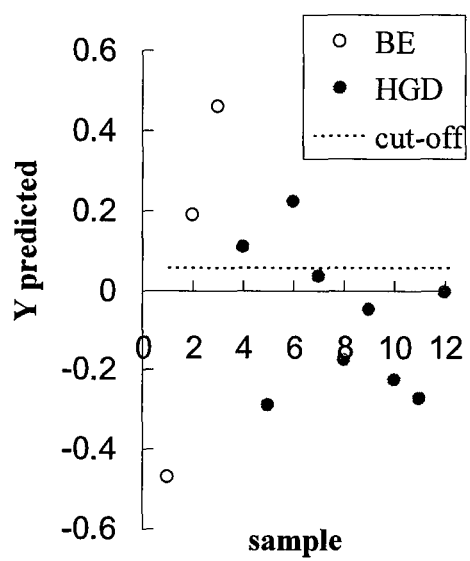

Models that included the biomarkers that were identified by NMR, either alone or in combination with the biomarkers that were identified by LC-MS increased the number of HGD samples that were predicted to fall below the EAC cutoff For a PLS-DA model based on metabolite biomarkers detected using NMR only, 7 out of 9 samples from HGD patients were indicated as being similar to EAC samples. FIG. 8D shows the results of the PLS-DA model using the 8 metabolite markers from NMR analyses; FIG. 8E shows the ROC curve using the cross-validated predicted class values (AUROC=0.86); FIG. 8F shows the PLS-DA prediction of BE and HGD samples from the NMR model comparing EAC and normal controls.

Figure 8G:
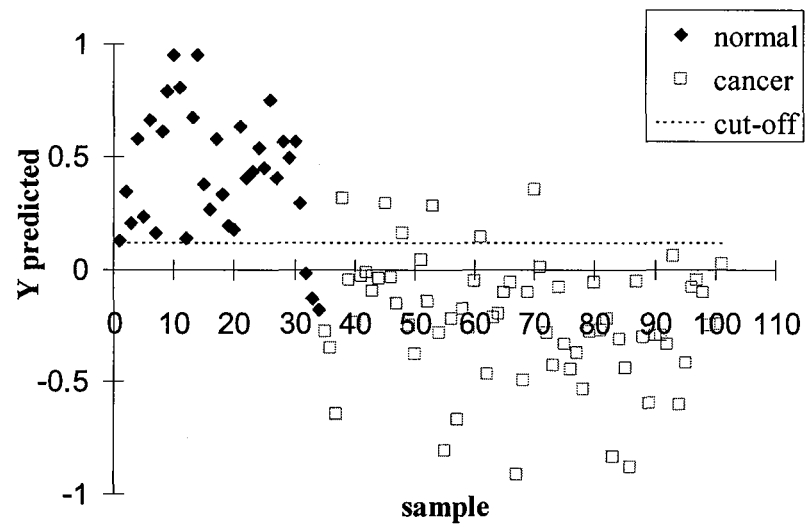
Figure 8H:
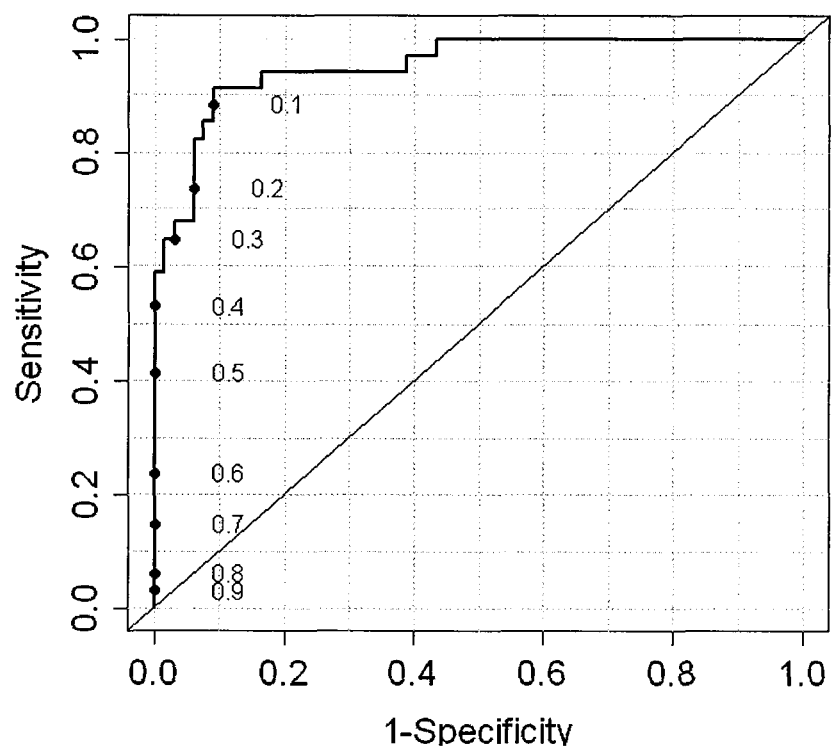
Figure 8I:
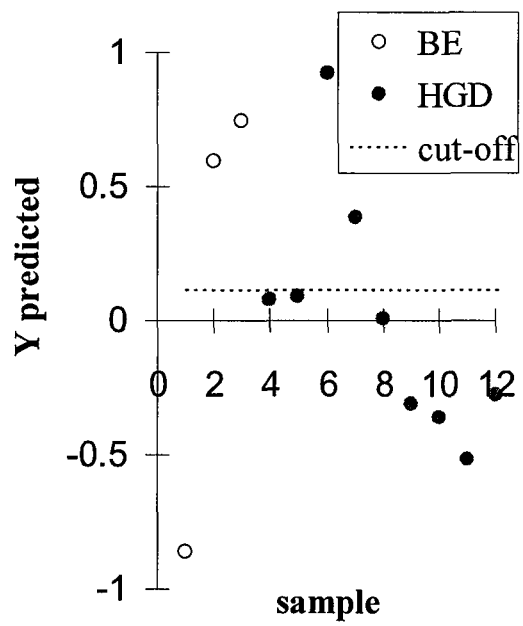

For a PLS-DA model based on a combination of the metabolite biomarkers detected using LC-MS and NMR, 7 out of 9 samples from HGD patients were indicated as being similar to EAC samples. FIG. 8G shows the results of the PLS-DA model using the combination of LC-MS and NMR detected metabolite markers. FIG. 8H shows the ROC curve using the cross-validated predicted class values (AUROC=0.95) and FIG. 8I shows the PLS-DA prediction of BE and HGD samples from the LC-MS AND NMR model comparing EAC and normal controls.

Comparison of Metabolic Profiles from EAC with High-Risk Patients:

The data for high-risk patients (BE and HGD patients) were combined for the analysis because of their small sample numbers. Univariate analysis of the data showed that 7 LC-MS and 8 metabolite biomarkers detected using NMR varied significantly between EAC and the high-risk patients. The results are summarized in Table 11, above.

PLS-DA models were built using the LC-MS and NMR derived metabolite signals, separately and in combination, to test the classification accuracy for the two patient groups.

Figure 9A:
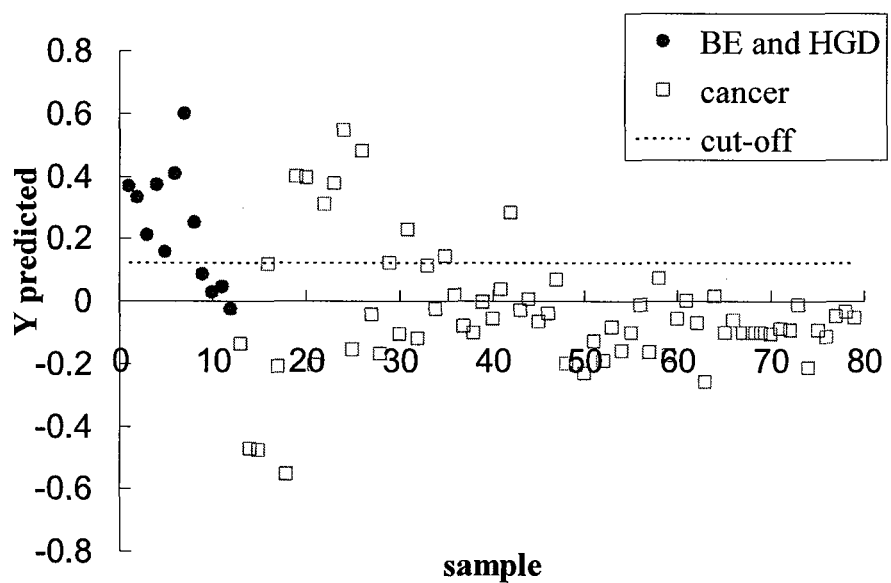
FIG. 9A-FIG. 9I show the results of a performance comparison of metabolic profiles from EAC patients and those with high risk esophageal diseases (BE+HGD).
Figure 9B:
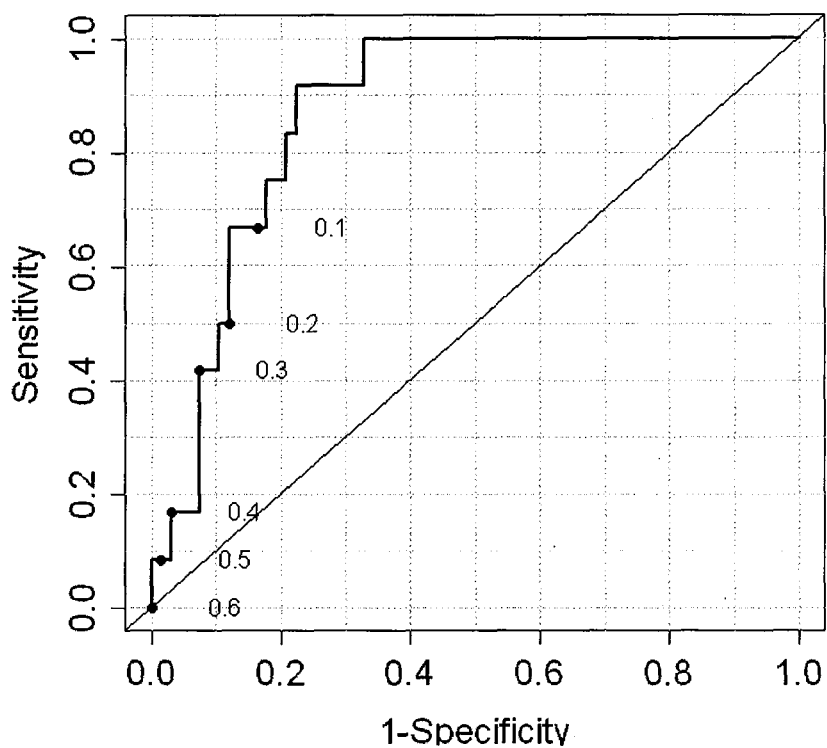
Figure 9C:
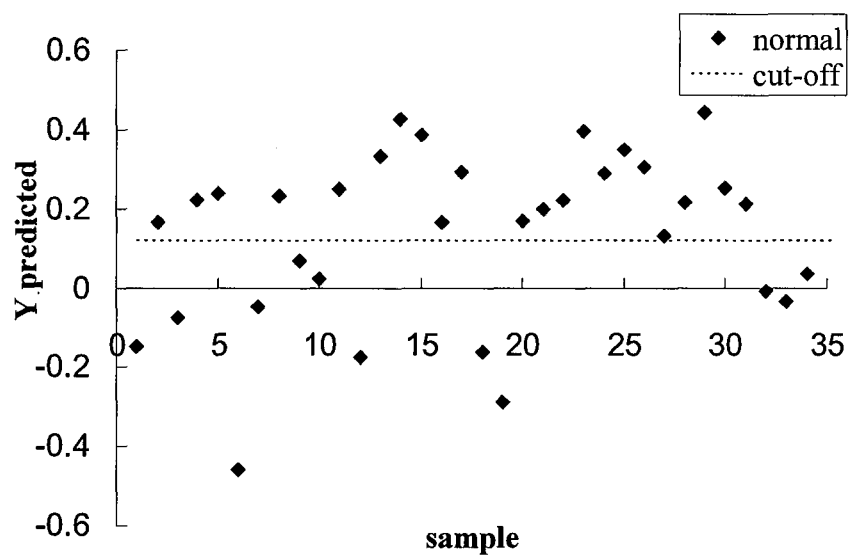

FIG. 9A shows the results of the PLS-DA model from the 7 metabolite markers from LC-MS analyses; FIG. 9B shows the ROC curve using the cross-validated predicted class values (AUROC=0.87); FIG. 9C shows the PLS-DA prediction for normal controls samples from the LC-MS model comparing EAC and BE+HGD.

Figure 9D:
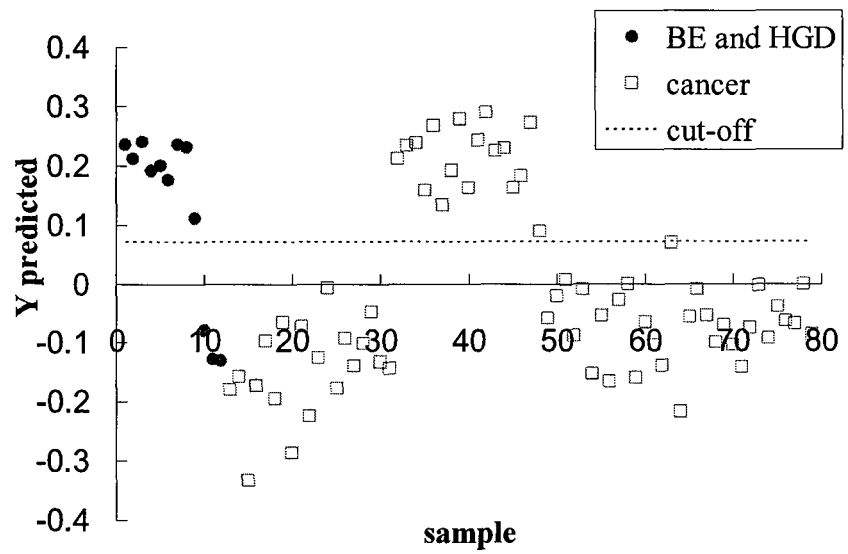
Figure 9E:
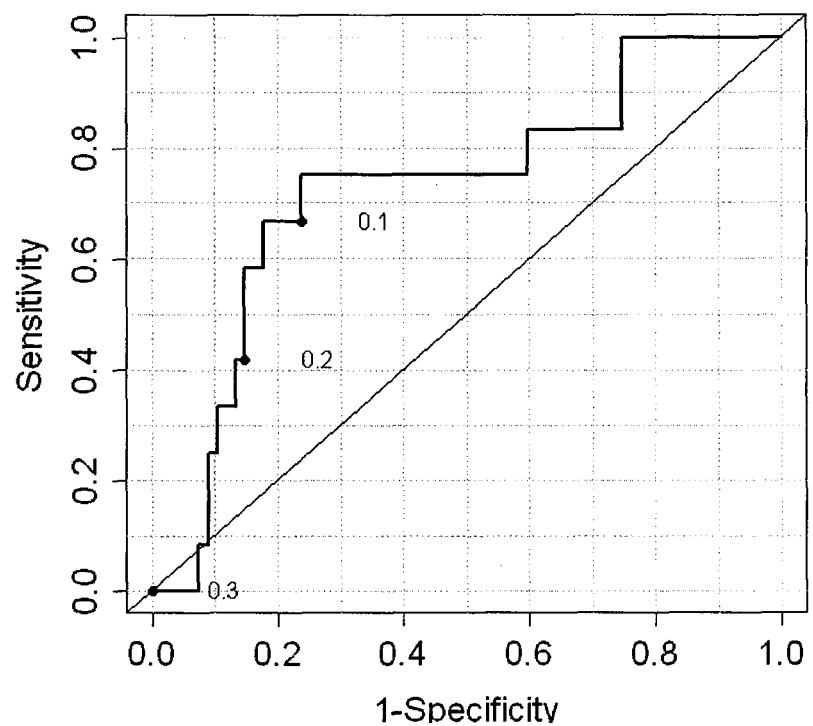
Figure 9F:
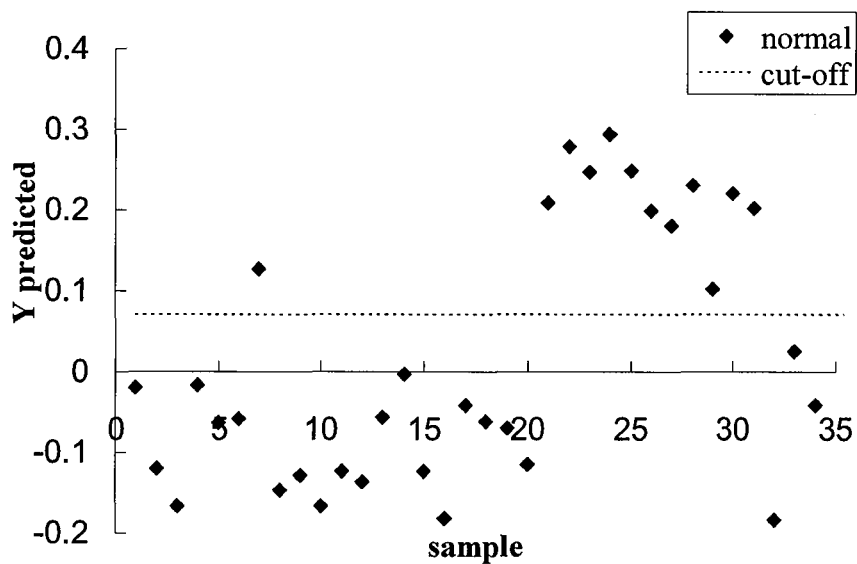

FIG. 9D shows the results of the PLS-DA model using the 8 metabolite markers from NMR analyses; FIG. 9E shows the ROC curve using the cross-validated predicted class values (AUROC=072); FIG. 9F shows the PLS-DA prediction of normal controls samples from the NMR model comparing EAC and BE+HGD.

Figure 9G:
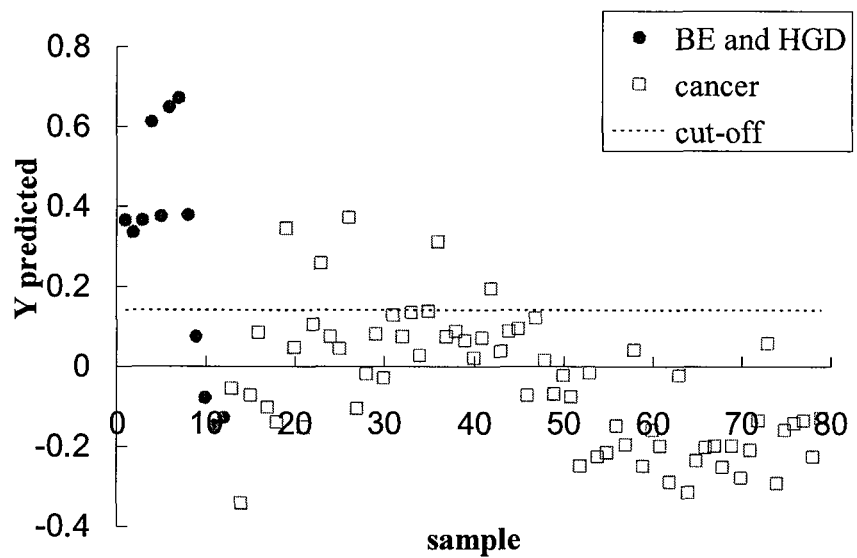
Figure 9H:
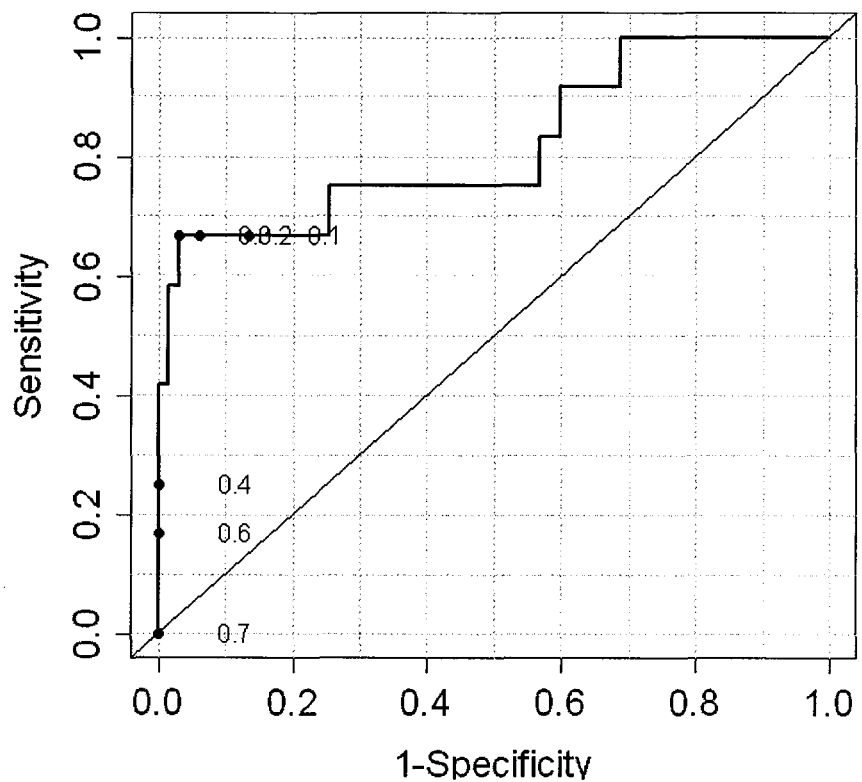
Figure 9I:
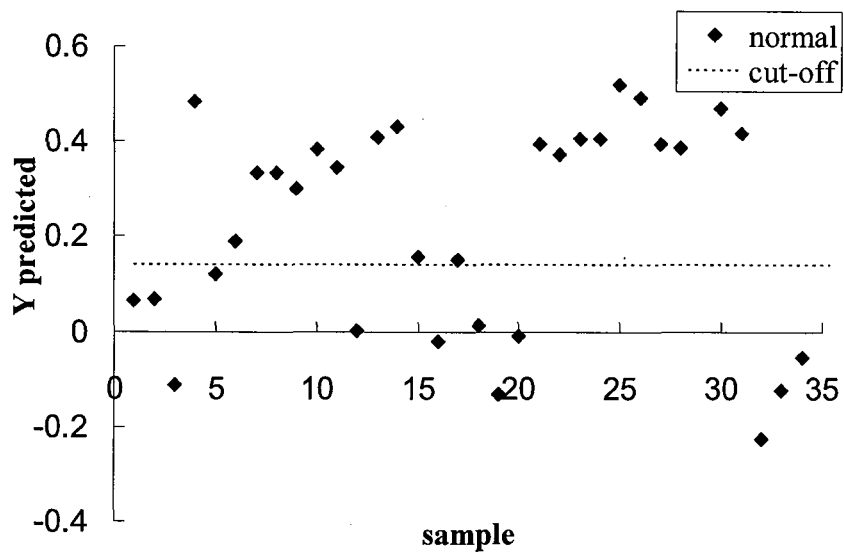

FIG. 9G shows the results of the PLS-DA model using the combination of LC-MS and NMR detected metabolite markers; FIG. 9H shows the ROC curve using the cross-validated predicted class values (AUROC=0.82); FIG. 9I shows the PLS-DA prediction of normal controls samples from the LC-MS AND NMR model comparing EAC and BE+HGD.

In summary, the model based on metabolite biomarkers identified using LC-MS provided sensitivity and specificity of 83% and 80%, respectively, with an AUROC of 0.87. The model based on metabolite biomarkers identified using NMR provided both sensitivity and specificity of 77% with an AUROC of 0.72. When the model was based on the combination of the metabolite biomarkers identified using either LC-MS and NMR, a sensitivity and specificity of 67% and 97% were obtained, respectively, with an AUROC of 0.82. Although the performance of the model from the combined data was slightly better than that from NMR data alone, the model derived from the metabolite biomarkers identified using LC-MS showed the best performance. When testing the controls using the same PLS-DA models derived from the LC-MS detected, NMR detected and combined metabolites, 22, 12 and 22 of 34 controls were above the cut-off value, respectively, and were therefore classified as not being similar to EAC patients.

Comparison of Metabolic Profiles from Normal Controls with High-Risk Patients:

Only one metabolite biomarker, pyroglutamic acid, detected by LC-MS, and three metabolite biomarkers detected using NMR, proline, lactic acid and an unknown metabolite, differed significantly (p<0.05) in a comparison of samples from high-risk patients and those from normal controls (Table 11). In addition, a peak arising from an N-acetylated protein in the NMR spectra showed a significant difference between the two groups. While the levels of pyroglutamic acid, proline and lactic acid were higher in the high-risk group, the others were lower.

The LC-MS and NMR data for the high-risk individuals and normal controls were compared using PLS-DA analysis. The lone distinguishing metabolite detected by LC-MS, pyroglutamic acid, had a sensitivity and specificity of 74% and 75%, respectively, with an AUROC of 0.76. A PLS-DA model based on the metabolites detected using NMR provided a sensitivity and specificity of 68% and 92%, respectively, with an AUROC of 0.80. The combined analysis of the data from the two analytical methods provided results similar to that NMR alone. However, all the models failed to give a clear prediction of the EAC patients.

Trending Markers:

Levels of the metabolites between the three groups, EAC, BE+HGD, and normal controls were compared using box-and-whisker plots. Interestingly, the average levels for twelve of the metabolites, including lactic acid, valine, leucine, methionine, tyrosine, tryptophan, myristic acid, linoleic acid, β-hydroxybutyrate, lysine, glutamine and citrate progressively changed with the average levels for BE and HGD patients falling in between the levels for normal controls and EAC. While the levels for lactic acid, β-hydroxybutyrate, lysine, glutamine and citrate increased, the levels for valine, leucine, methionine, tyrosine, tryptophan, myristic acid and linoleic acid decreased progressively.

Figure 10A:
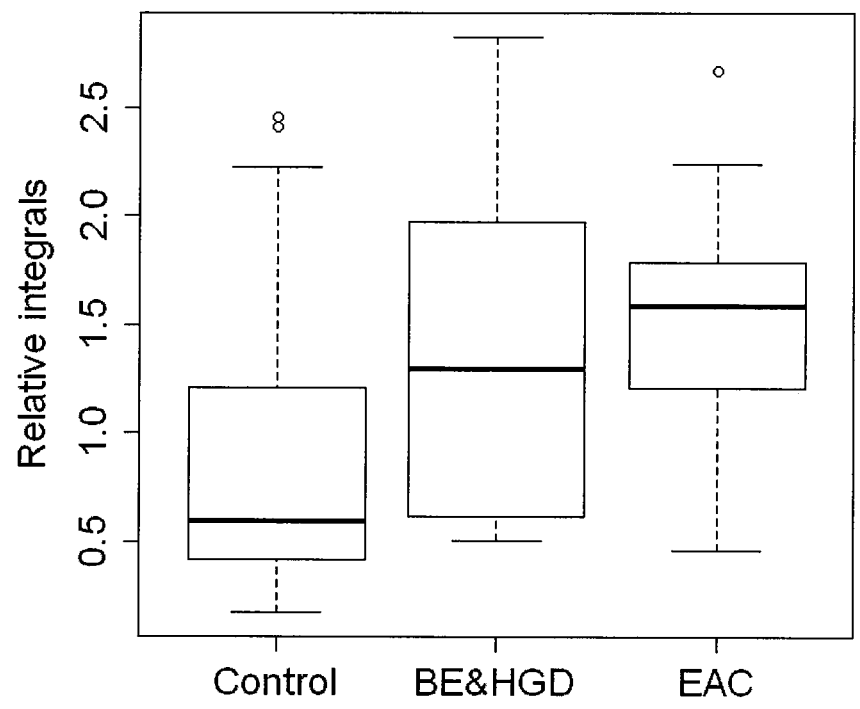
FIG. 10A-FIG. 10L show box-and-whisker plots illustrating progressive changes of the mean metabolite levels in high-risk patients (BE and HGD) and esophageal adenocarcinoma (EAC) patients relative to normal controls, in which the y axis for each plot indicates the relative concentration level of each metabolite normalized by the internal standard. The first eight markers were detected by LC-MS, and the remaining four were detected by NMR, FIG. 10A, lactic acid.
Figure 10B:
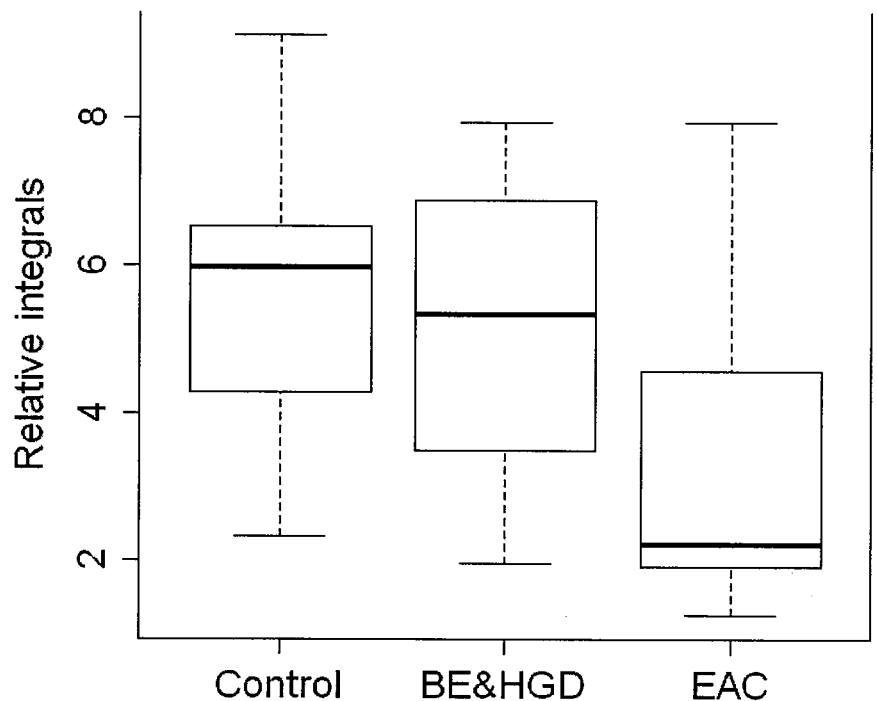
Figure 10C:
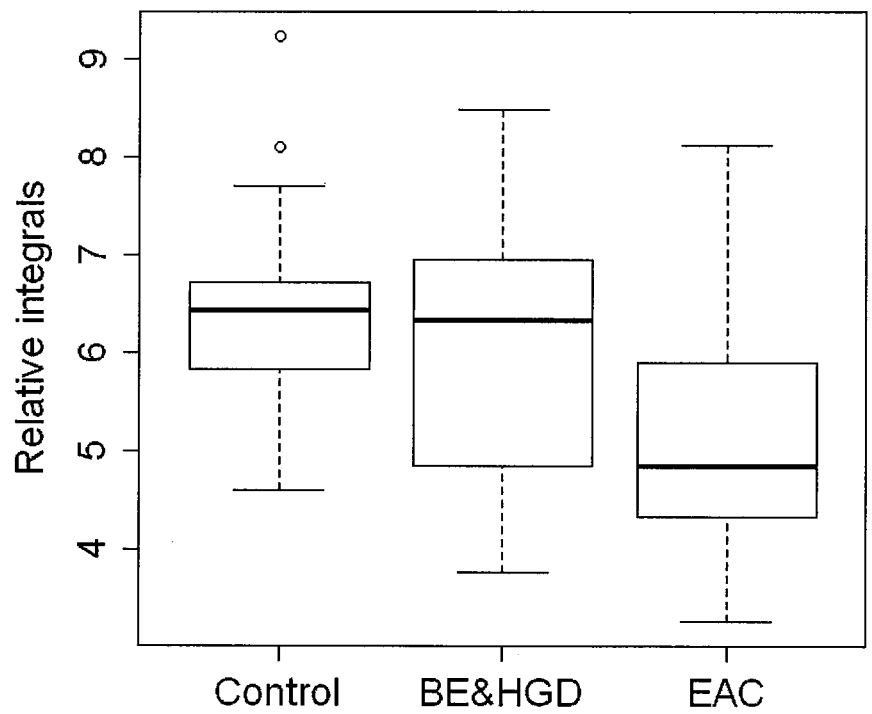
Figure 10D:
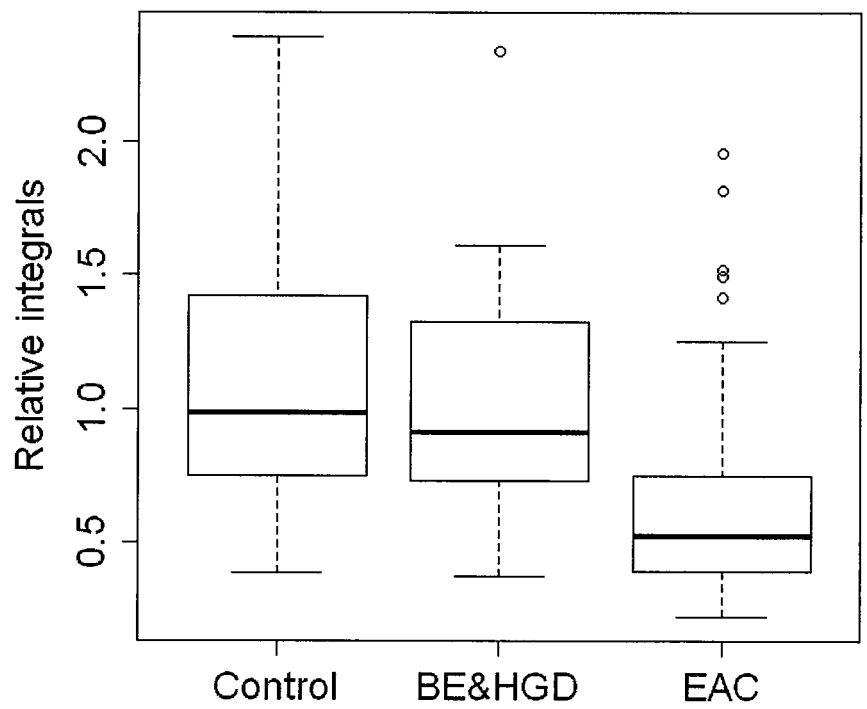
Figure 10E:
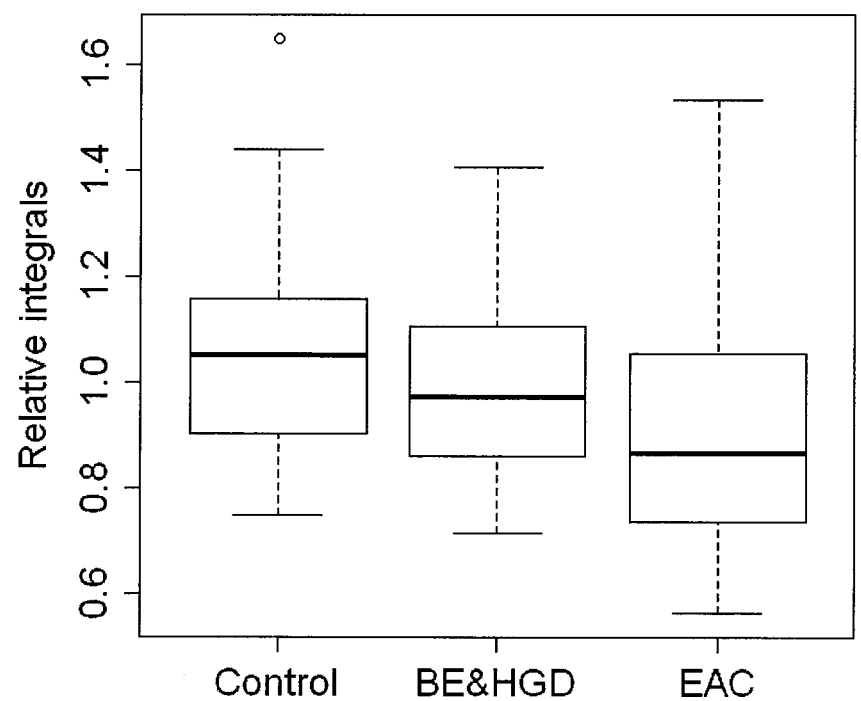
Figure 10F:
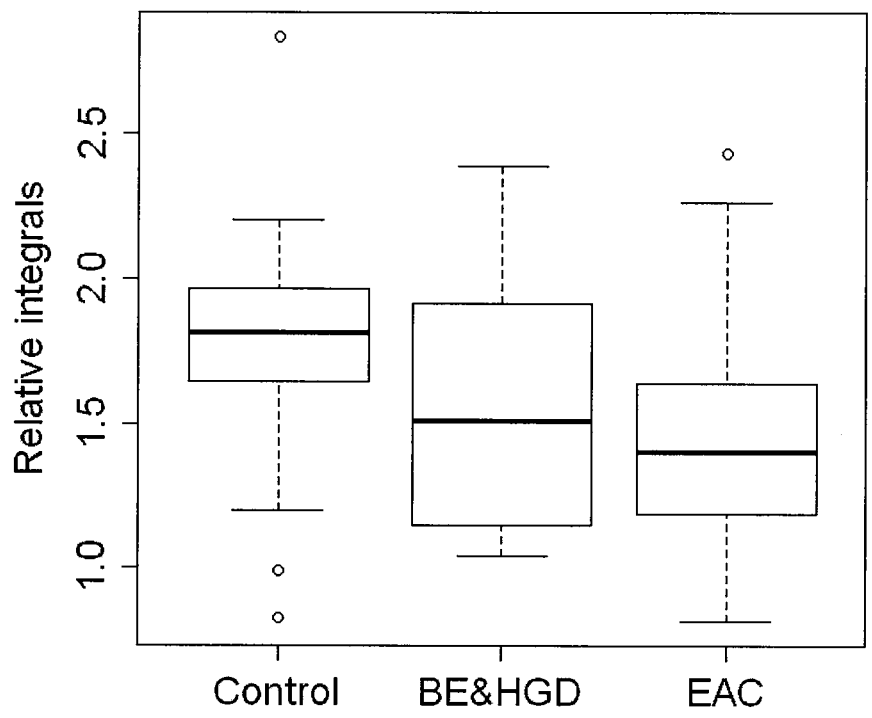
Figure 10G:
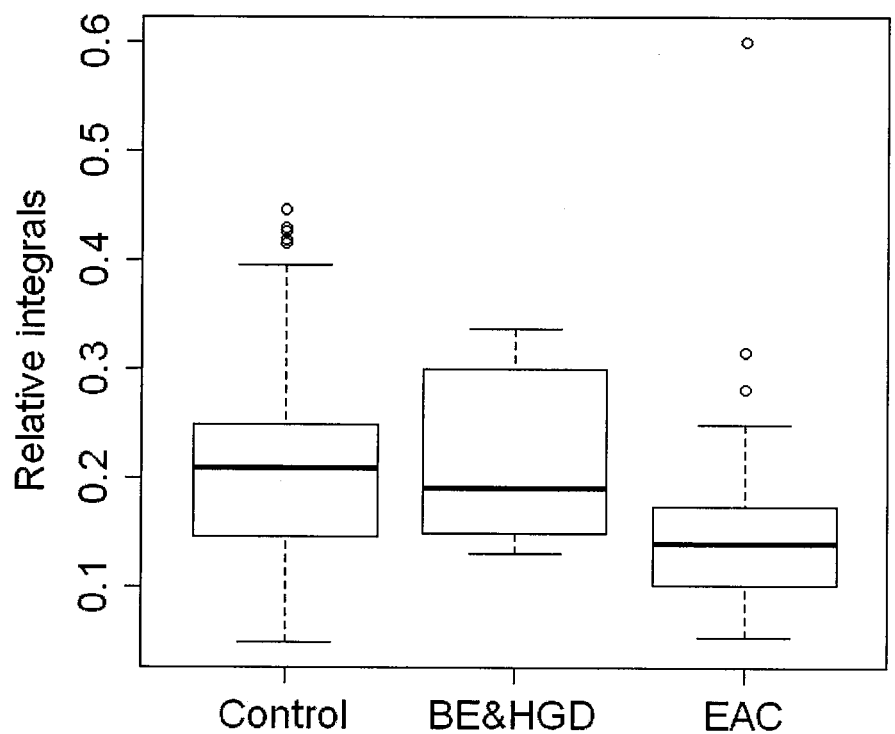
Figure 10H:
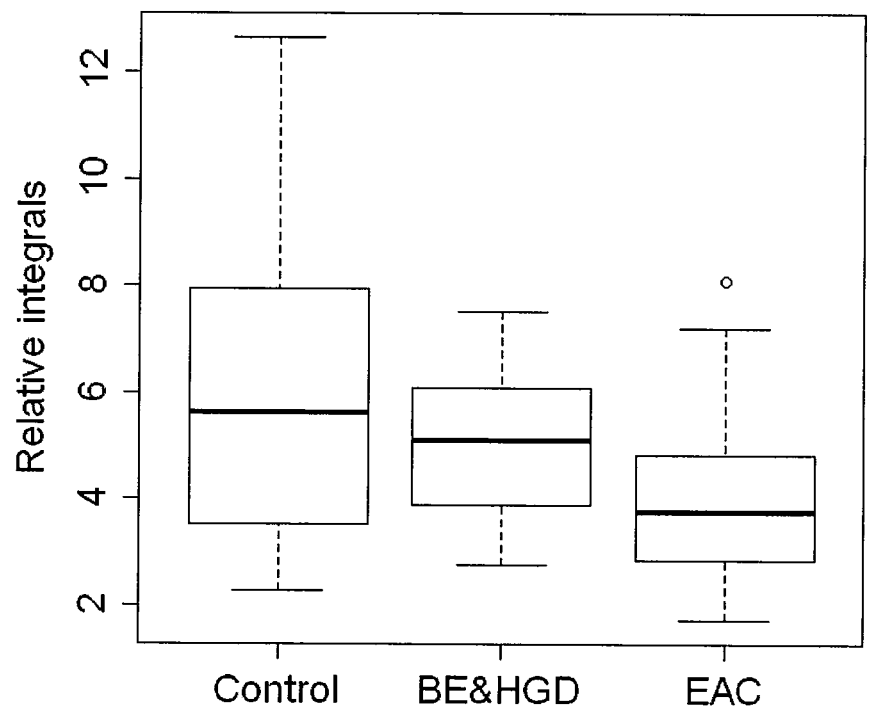
Figure 10I:
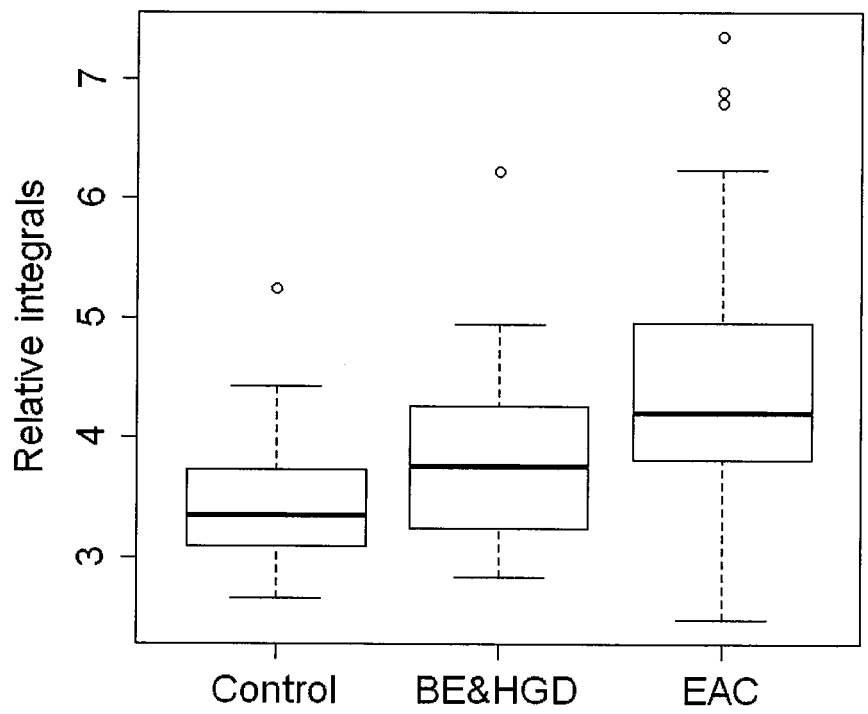
Figure 10J:
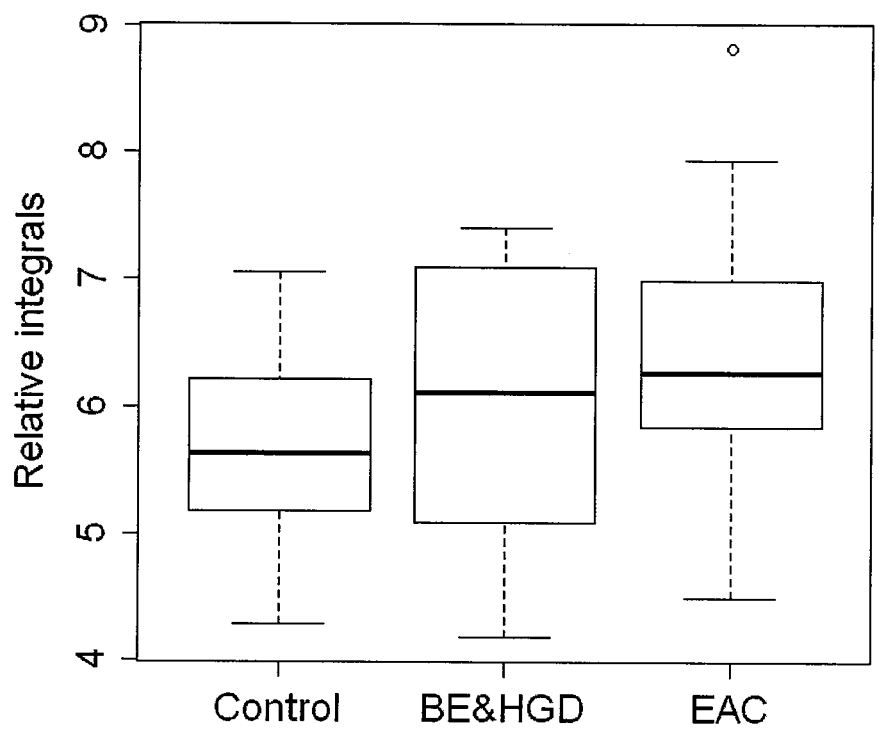
Figure 10K:
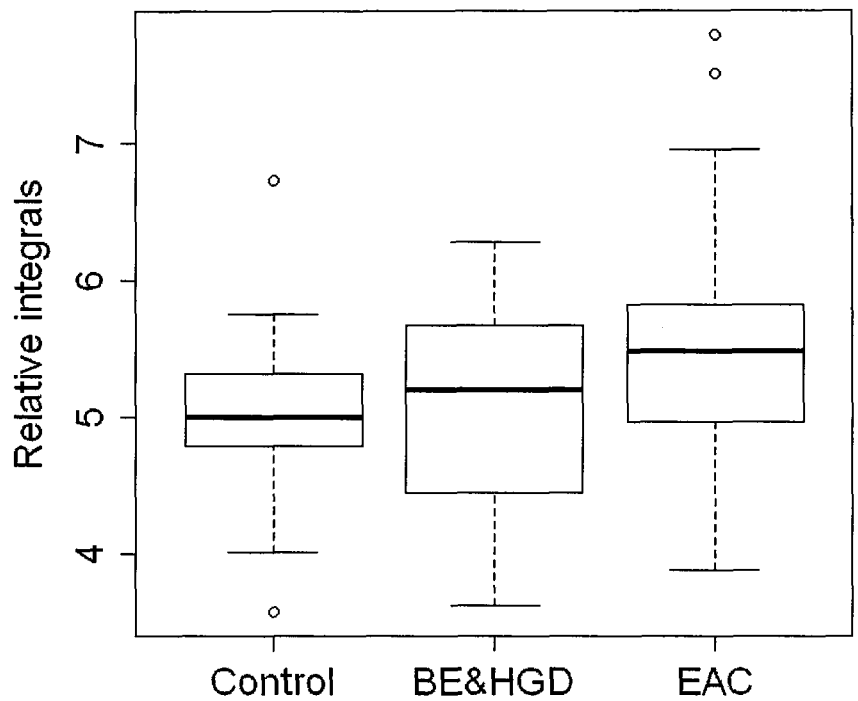
Figure 10L:
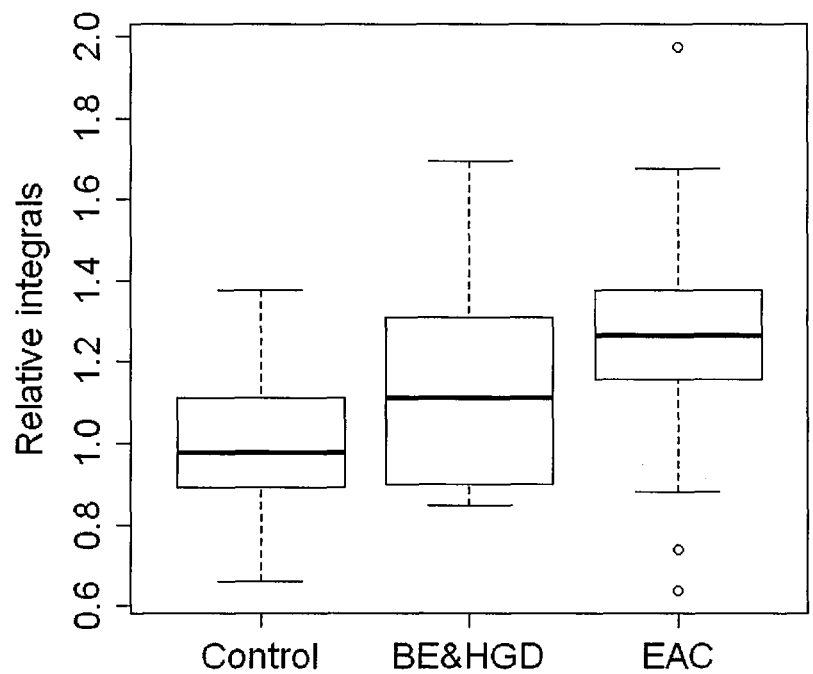

FIG. 10A-FIG. 10L show box-and-whisker plots illustrating progressive changes of the mean metabolite levels in high-risk patients (BE and HGD) and esophageal adenocarcinoma (EAC) patients relative to normal controls, in which the y axis for each plot indicates the relative concentration level of each metabolite normalized by the internal standard. The first eight markers were detected by LC-MS, and the remaining four were detected by NMR. FIG. 10A, lactic acid; FIG. 10B, valine; FIG. 10C, leucine; FIG. 10D, methionine; FIG. 10E, tyrosine; FIG. 10F tryptophan; FIG. 10G, myristic acid; FIG. 10H, linoleic acid; FIG. 10I, β-hydroxybutyrate; FIG. 10J, lysine; FIG. 10K, glutamine; and FIG. 10L, citrate.

Using these twelve markers, PLS-DA models were again built using LC-MS and NMR separately and in combination, to test the classification accuracy for each of the two group comparisons. A PLS-DA model for EAC compared to the normal controls was used to predict values for the high-risk patients. The model provided a sensitivity and specificity of 89% and 90%, respectively, with an AUROC of 0.92. However, the predictive model for BE and HGD did not improve over that using the previous PLS-DA model (FIG. 8A-FIG. 8F). FIG. 4B shows the PLS-DA model comparing EAC and the high-risk patient group.

Figure 11A:
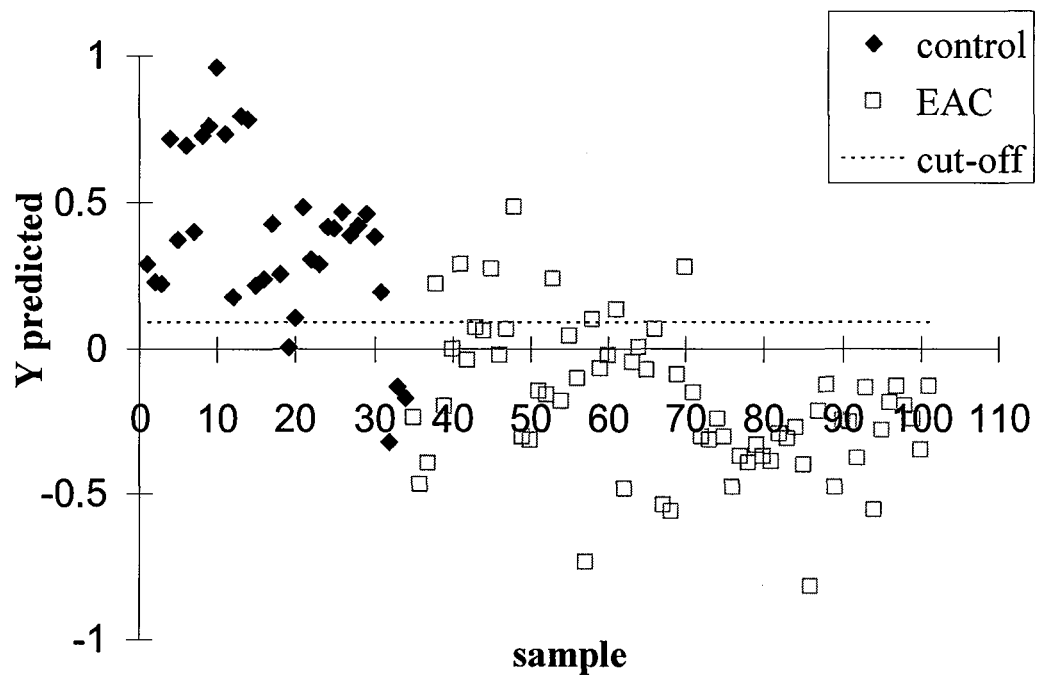
FIG. 11A-FIG. 11F show PLS-DA models comparing two patient groups, their corresponding ROC curves, and the prediction of the models for the other (third) patient group using the 12 trending markers of FIG. 10A-FIG. 10L.
Figure 11B:
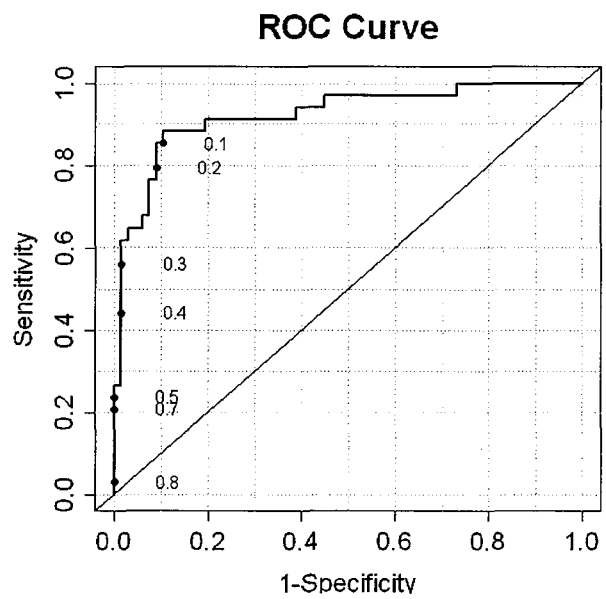
Figure 11C:
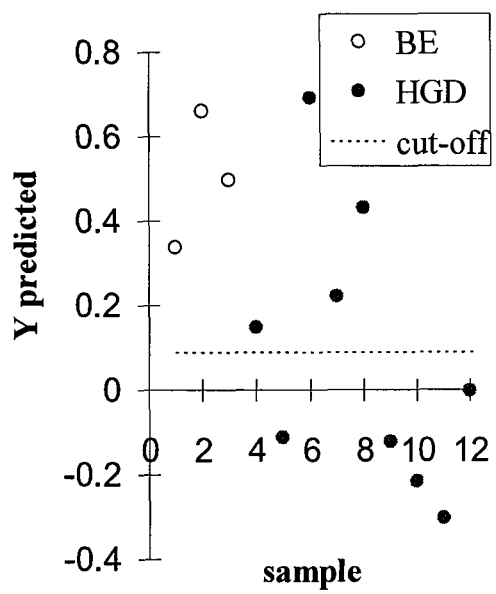
Figure 11D:
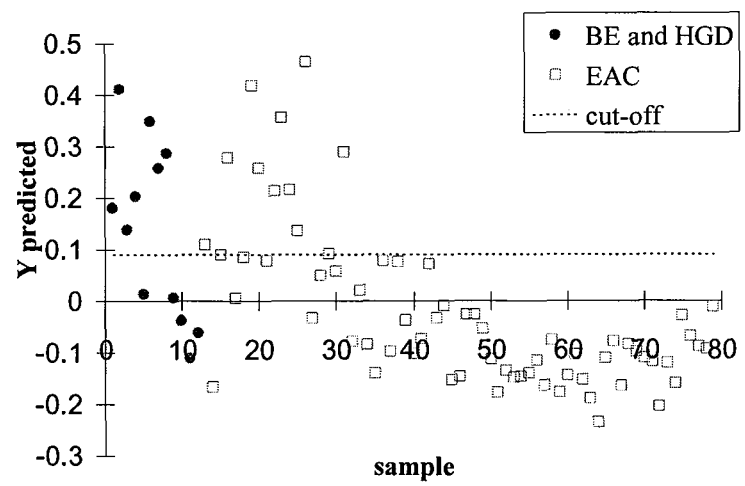
Figure 11E:
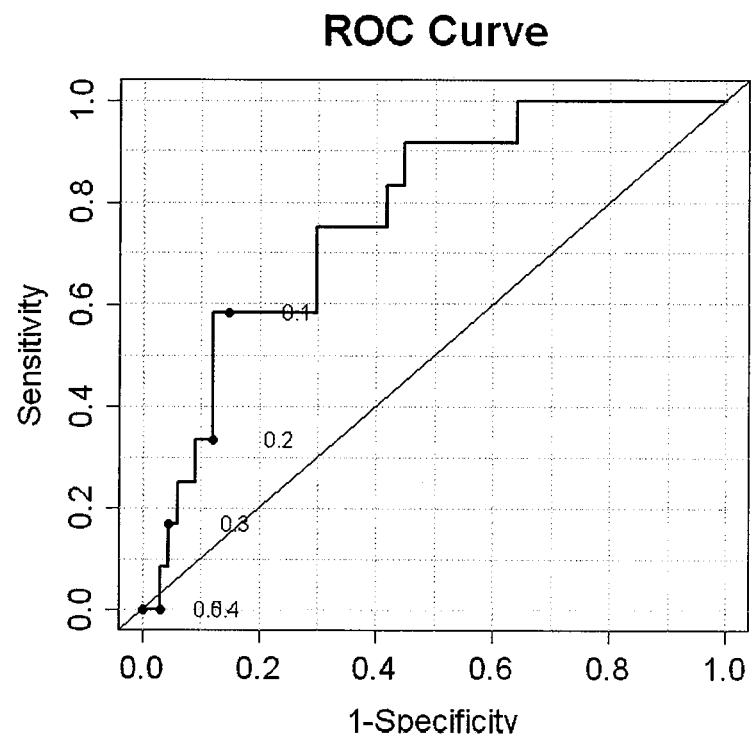
Figure 11F:
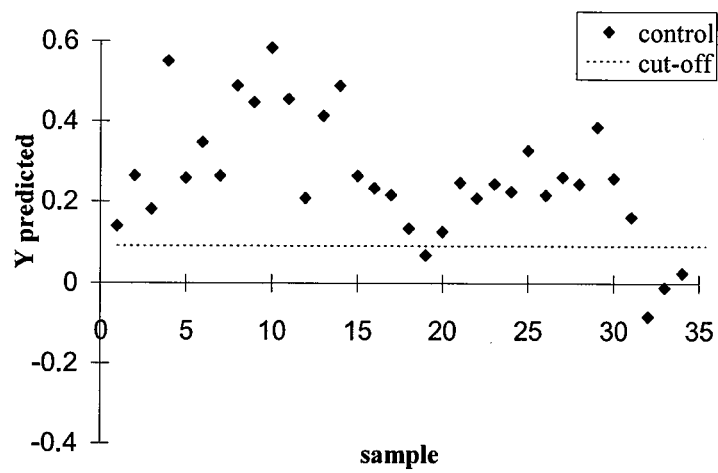

FIG. 11A-FIG. 11F show PLS-DA models comparing two patient groups, their corresponding ROC curves, and the prediction of the models for the other (third) patient group using the 12 trending markers of FIG. 10A-FIG. 10E. FIG. 11A shows the results of the performance comparison of metabolic profiles between EAC patients and normal controls; FIG. 11B shows the ROC curve using the cross-validated predicted class values (AUROC=0.92); FIG. 11C shows the PLS-DA prediction for BE+HGD samples from the model comparing EAC and normal controls. FIG. 11D shows the results of the performance comparison of metabolic profiles between EAC patients and normal controls; FIG. 11E shows the ROC curve using the cross-validated predicted class values (AUROC=0.78); FIG. 11F shows the PLS-DA prediction for normal controls samples from the model comparing EAC and BE+HGD patients. This model provided a sensitivity, specificity and AUROC of 76% 70% and 0.78, respectively. In this case an improvement in the predictive testing of the control subjects was obtained, with 30 out of 34 controls appearing above the cut-off line (non-EAC like). However, these twelve markers could not be used to generate a clear classification between normal controls and at risk patients using PLS-DA.

Figure 12A:
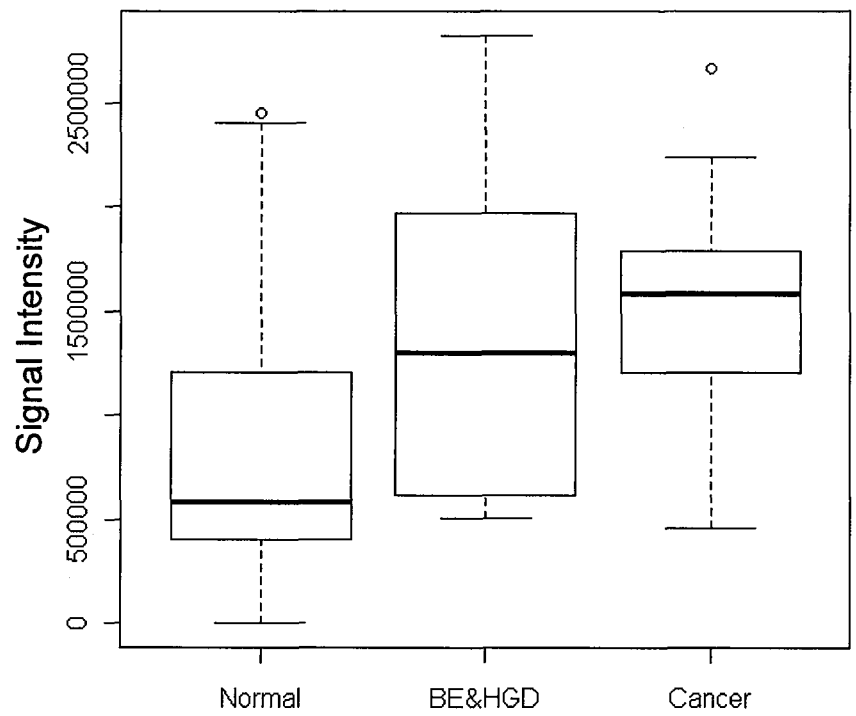
FIG. 12A-FIG. 12L show box-and-whisker plots illustrating differences between EAC patients, high-risk patients (BE and HUD) and normal controls, for the 12 markers detected by LC-MS, in which the y axis for each plot indicates the signal intensity.
Figure 12B:
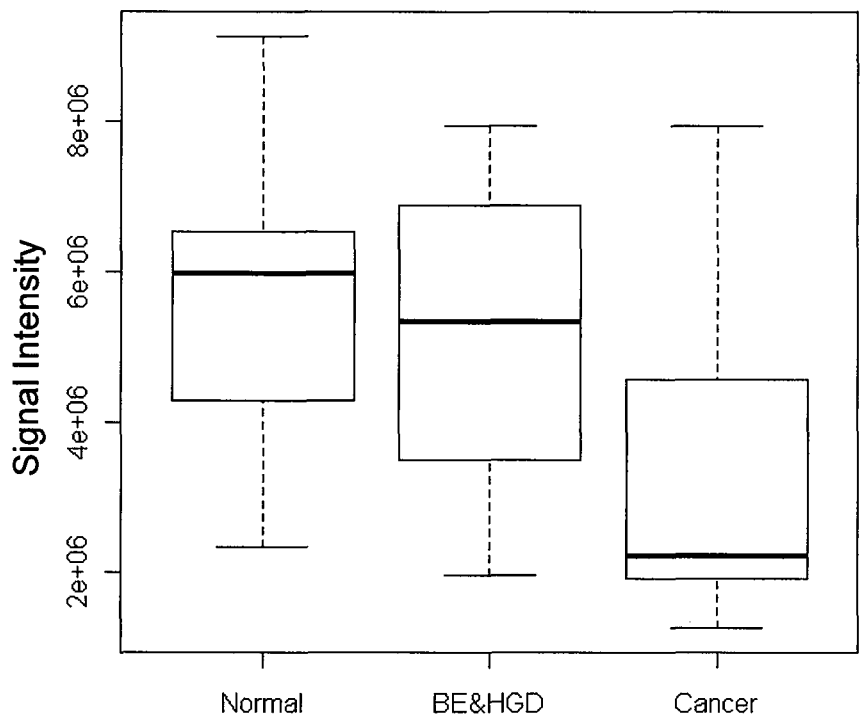
Figure 12C:
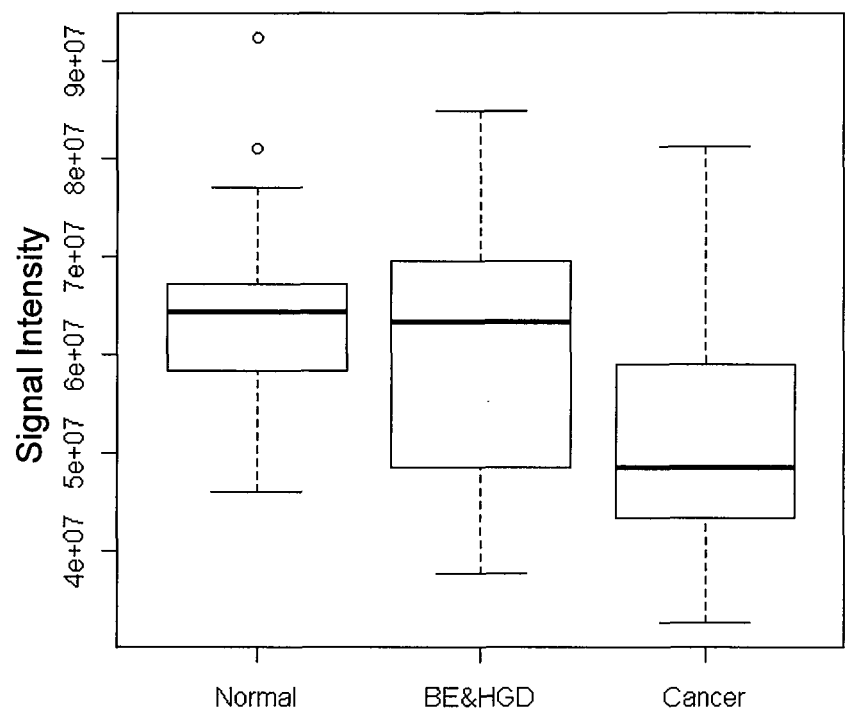
Figure 12D:
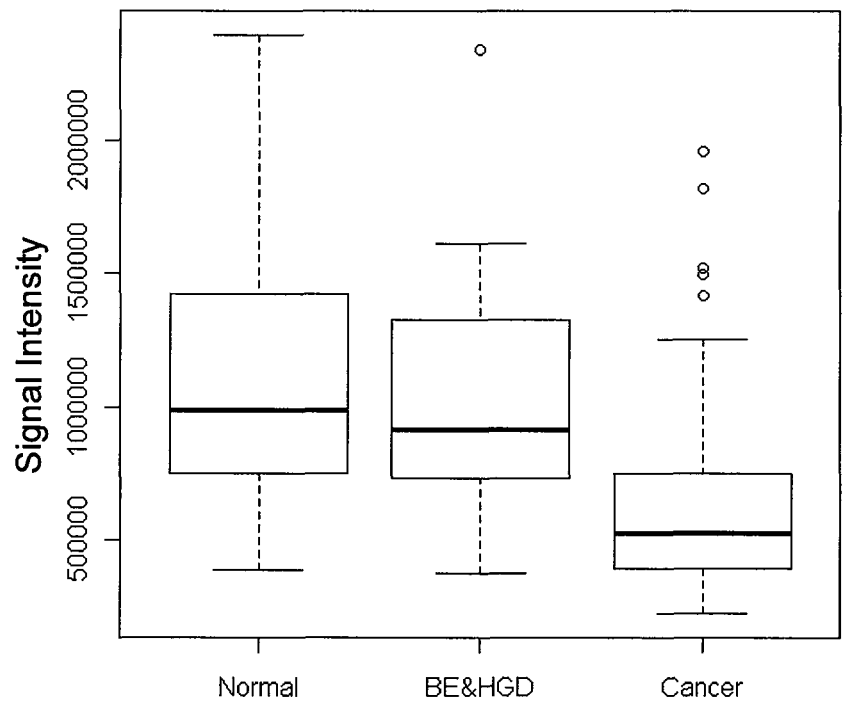
Figure 12E:
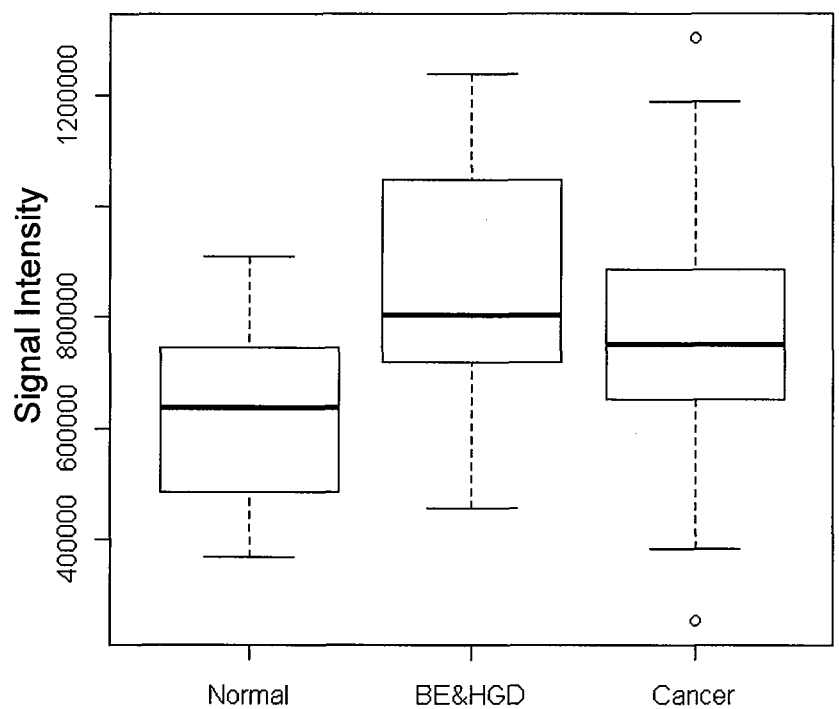
Figure 12F:
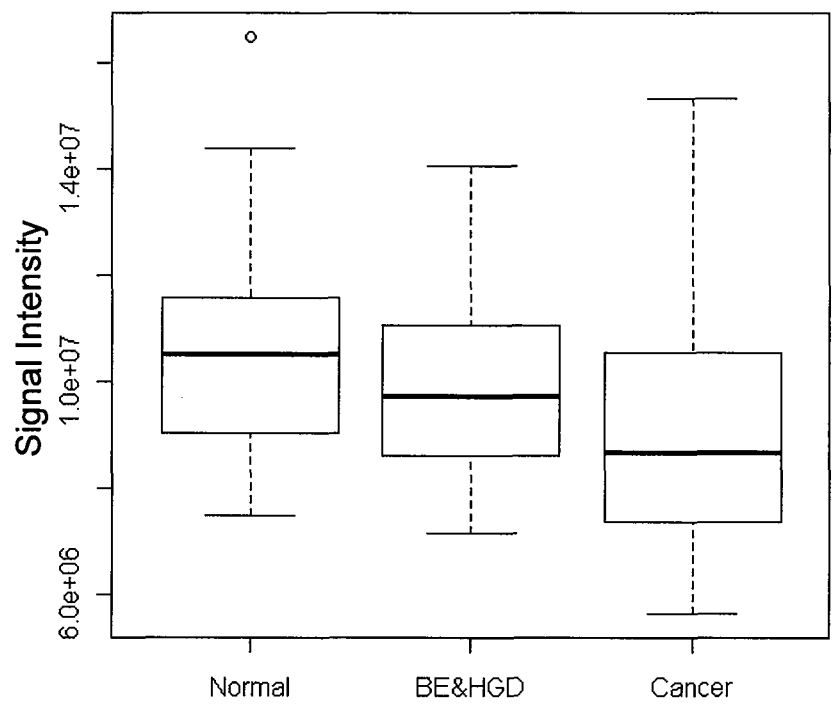
Figure 12G:
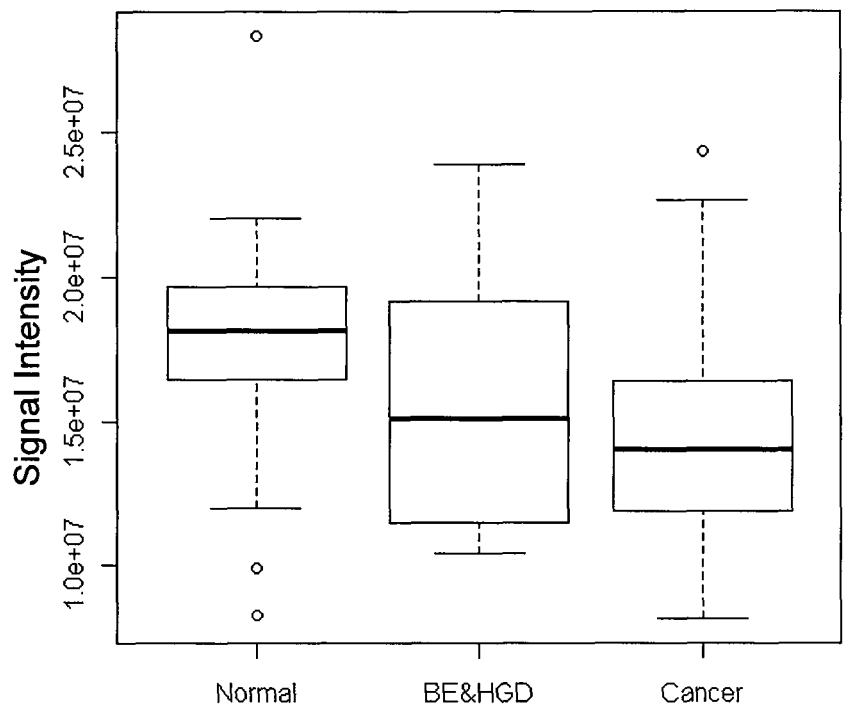
Figure 12H:
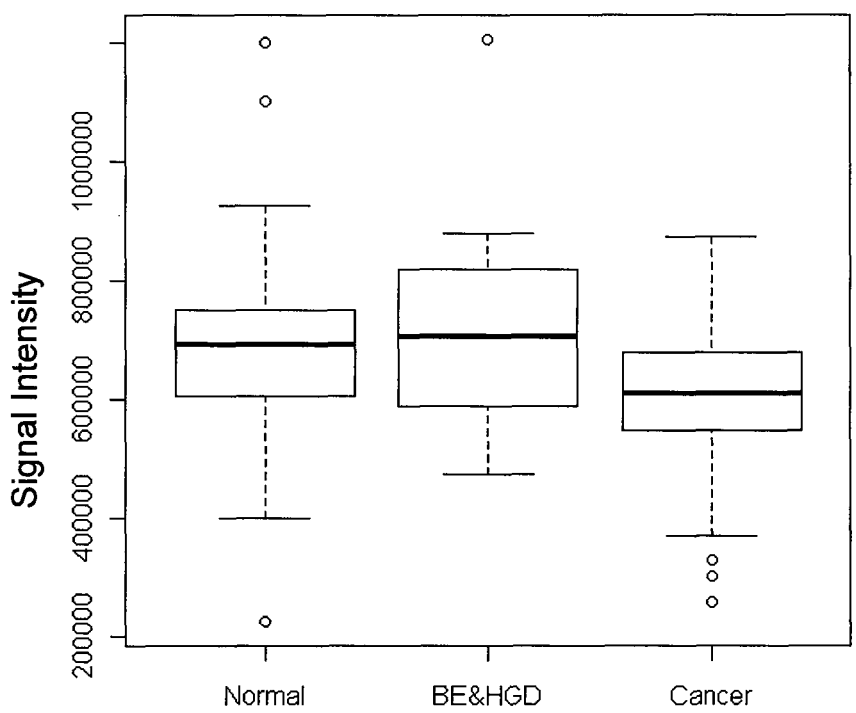
Figure 12I:
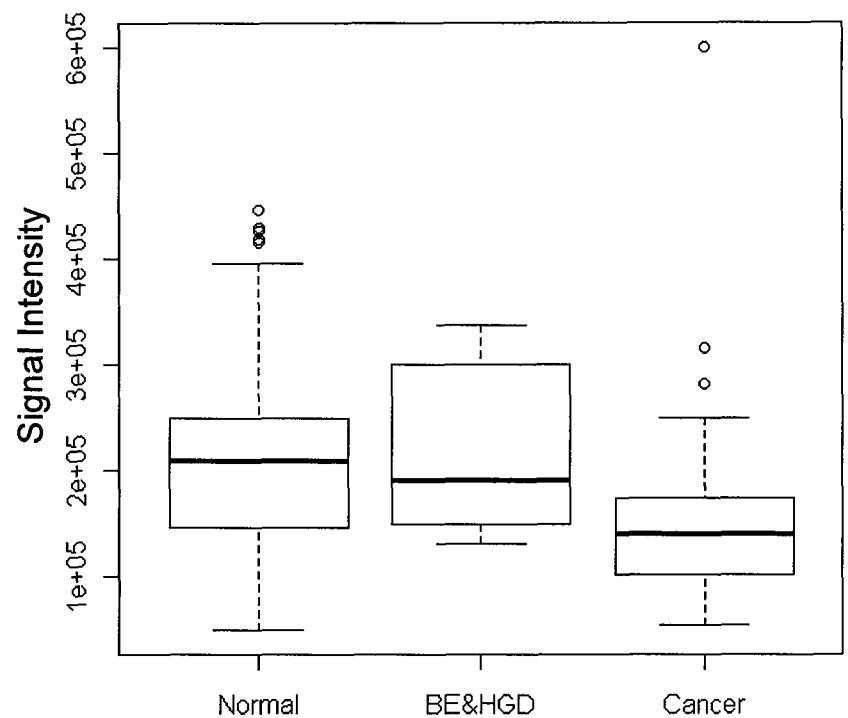
Figure 12J:
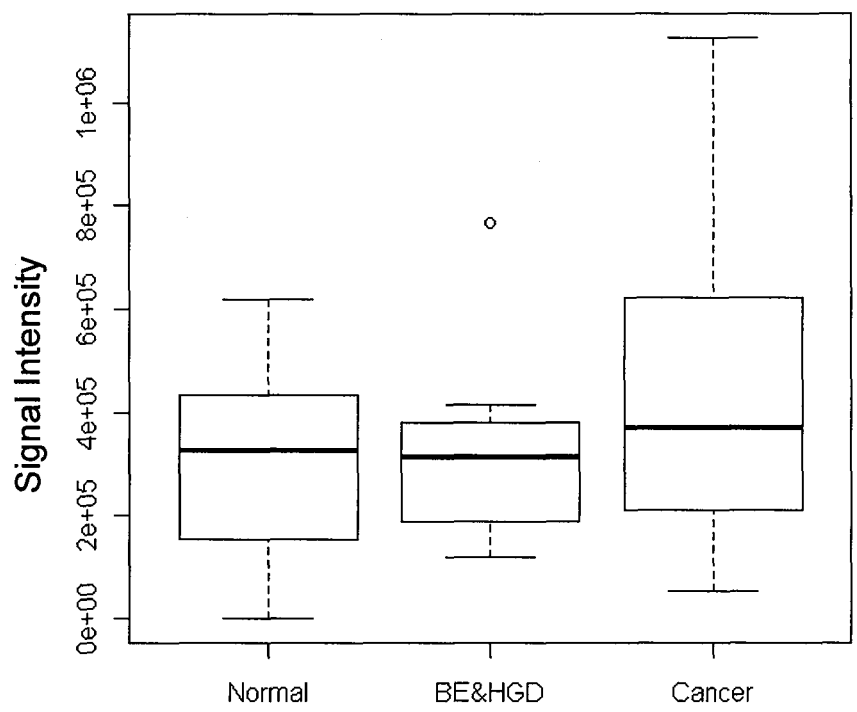
Figure 12K:
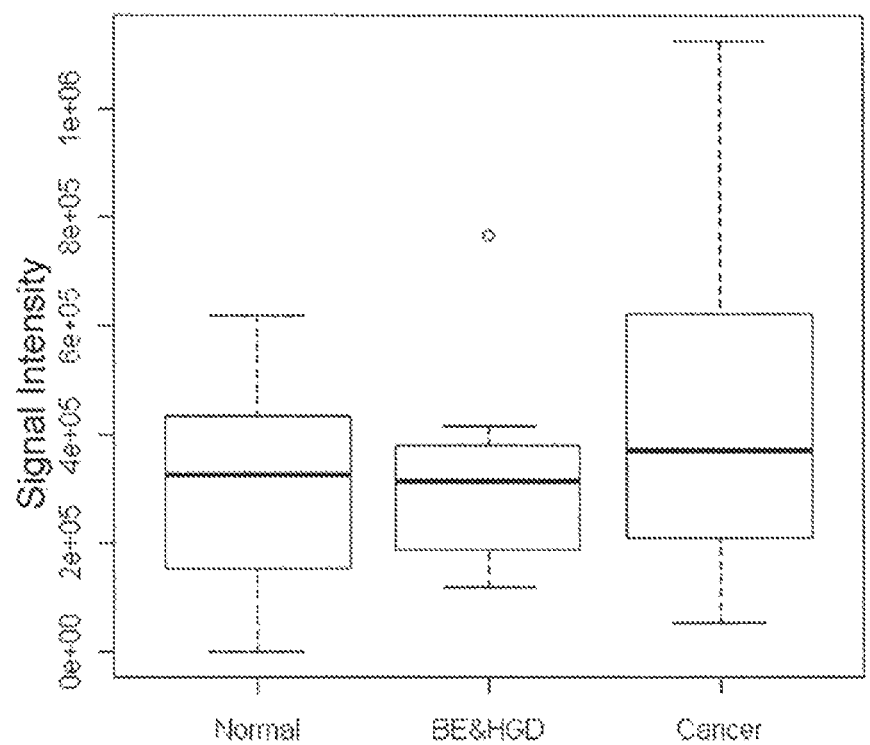
Figure 12L:
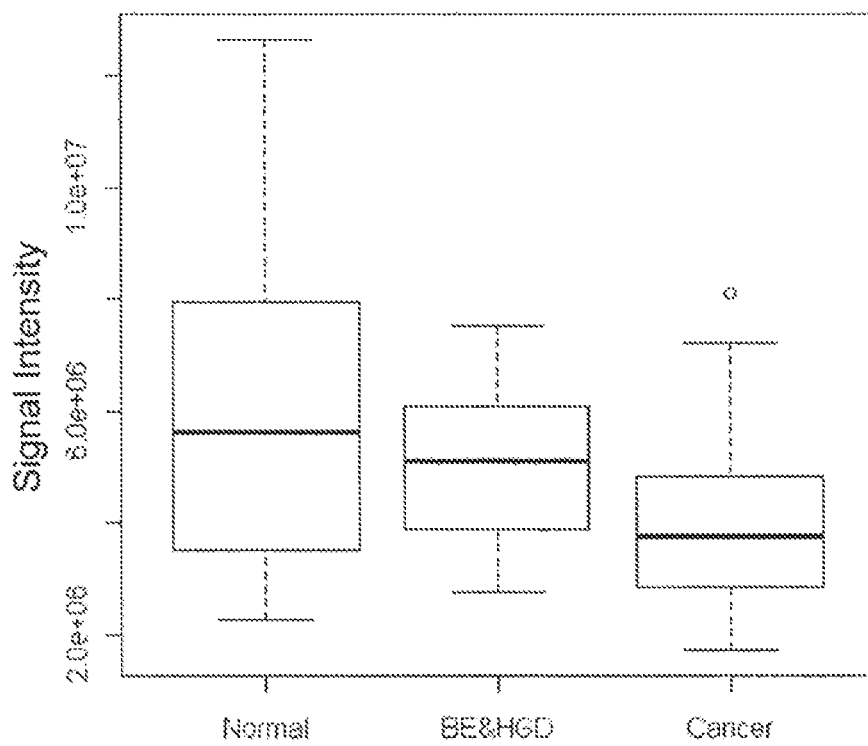
Figure 12M:
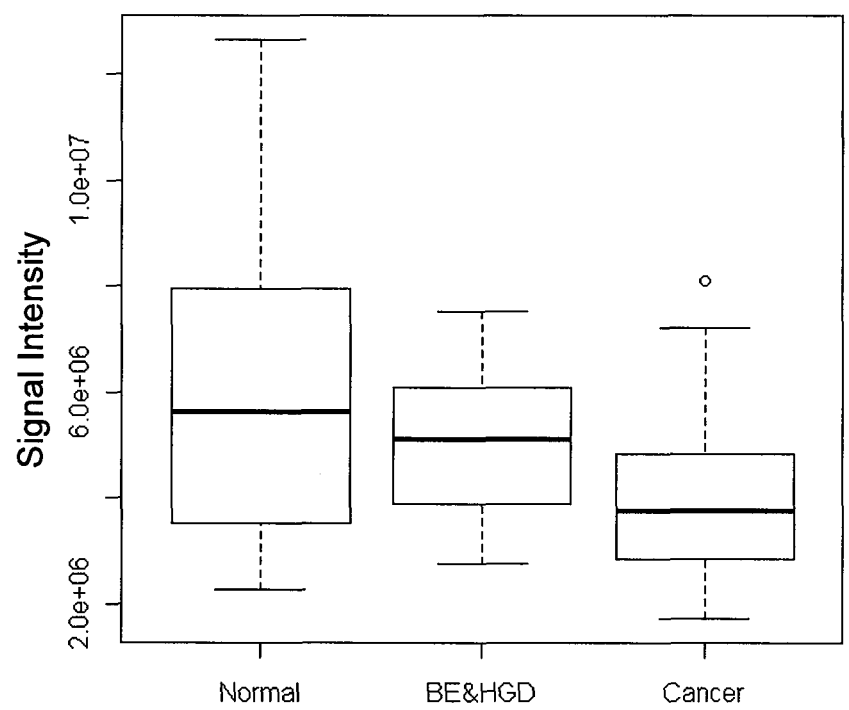

FIG. 12A-FIG. 12L show box-and-whisker plots illustrating differences between EAC patients, high-risk patients (BE and HGD) and normal controls, for the 12 markers detected by LC-MS, in which the y axis for each plot indicates the signal intensity. FIG. 12A, lactic acid; FIG. 12B, valine; FIG. 12C, leucine; FIG. 12D, methionine; FIG. 12E, carnitine; FIG. 12F, tyrosine; FIG. 12G, tryptophan; FIG. 12H, 5-hydroxytryptophan; FIG. 12I, myristic acid; FIG. 12J, margaric acid; FIG. 12K, linolenic acid; and FIG. 12L, linoleic acid.

Figure 13A:
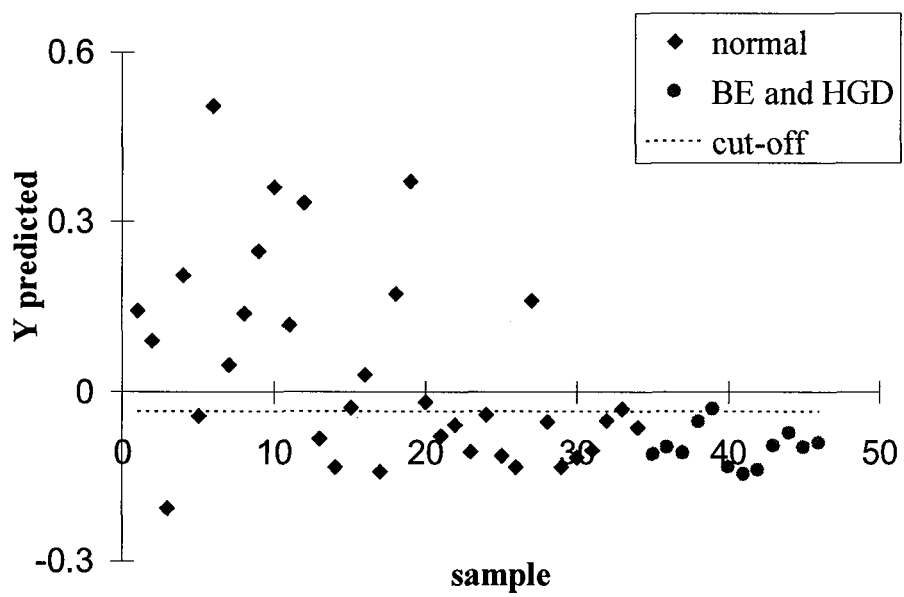
FIG. 13A-FIG. 13I show the results of a performance comparison of metabolic profiles from normal controls and high-risk (BE+HGD) patients.
Figure 13B:
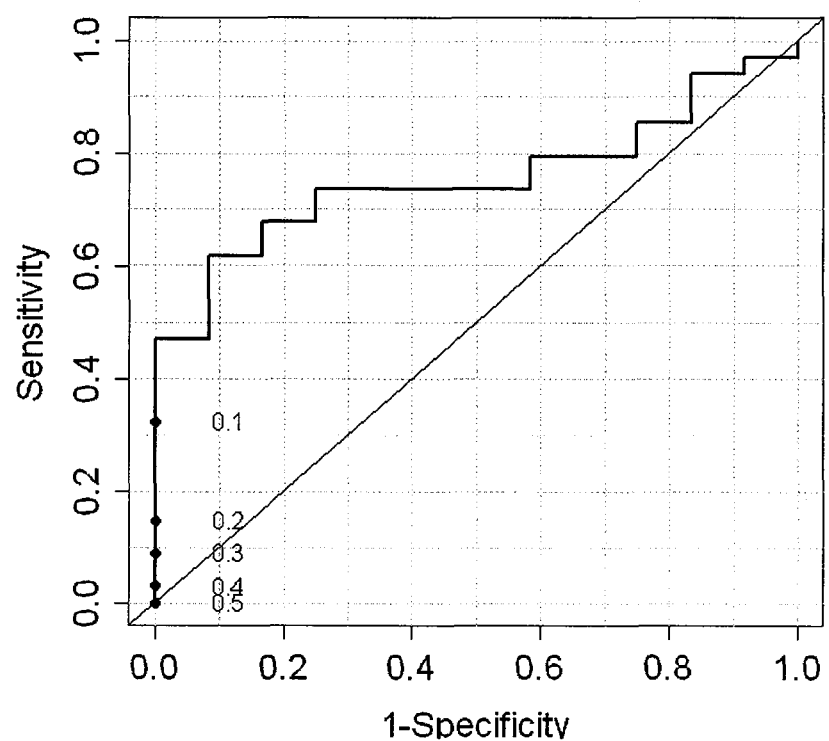
Figure 13C:
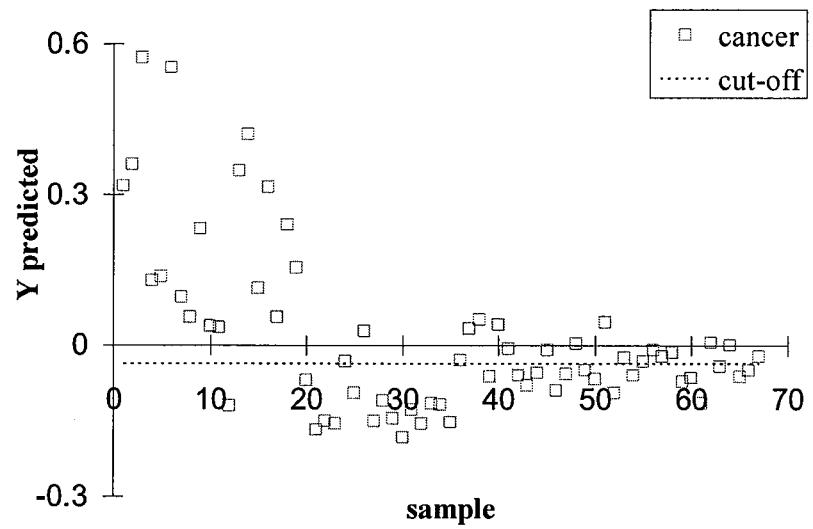

FIG. 13A-FIG. 13I show the results of a performance comparison of metabolic profiles from normal controls and high-risk (BE+HGD) patients. FIG. 13A shows the results of the PLS-DA model for comparing normal controls and high-risk (BE+HGD) patients using the one metabolite biomarker from LC-MS analyses; FIG. 13B shows the ROC curve using the cross-validated predicted class values (AUROC=0.76); FIG. 13C shows the PLS-DA prediction for EAC samples using the same metabolite and cutoff.

Figure 13D:
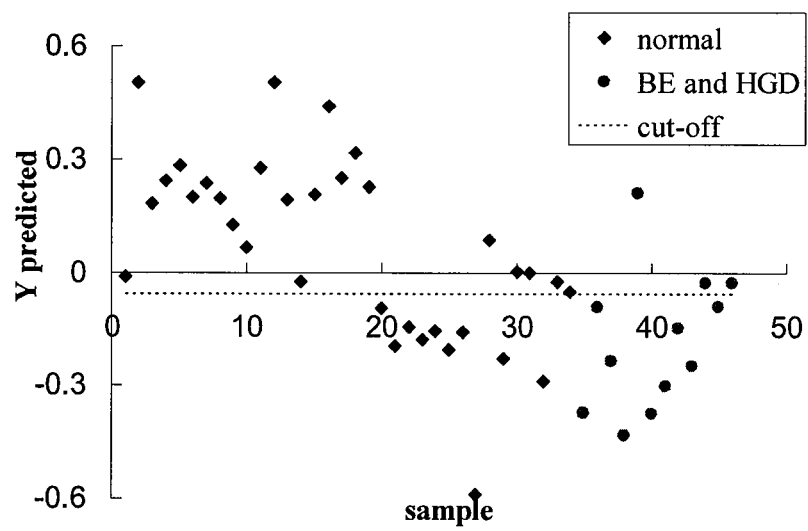
Figure 13E:
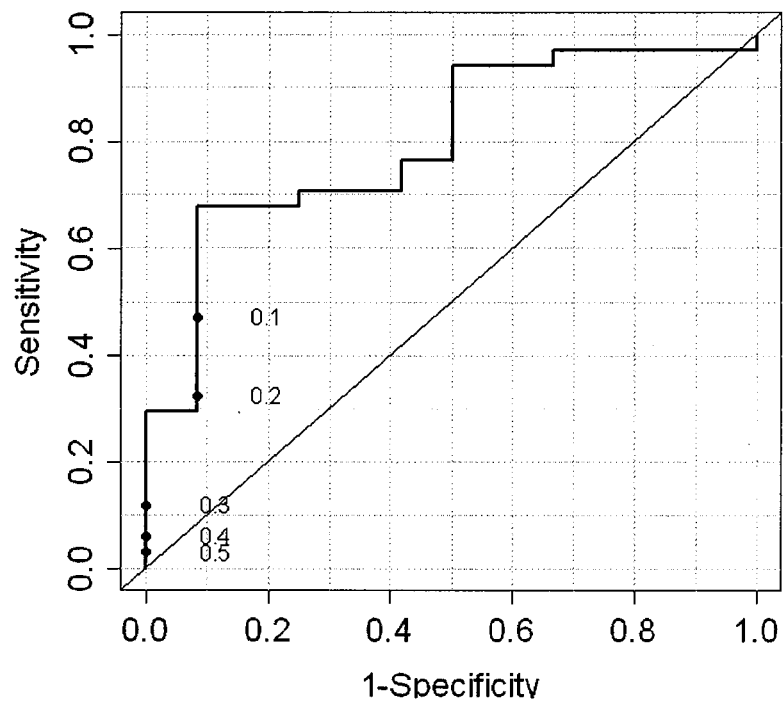
Figure 13F:
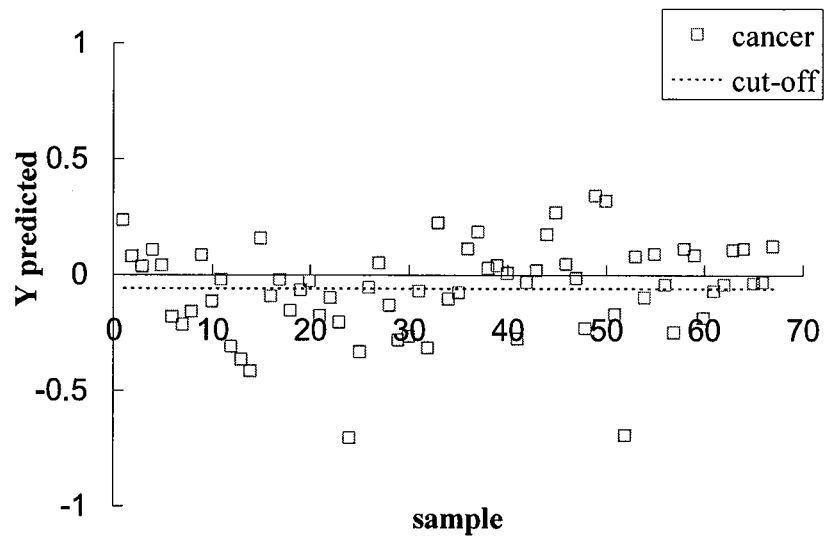

FIG. 13D shows the results of the PLS-DA model comparing normal controls and high-risk (BE+HGD) patients using the 4 metabolite markers identified by NMR analyses; FIG. 13E shows the ROC curve using the cross-validated predicted class values (AUROC=0.80); FIG. 13F shows the PLS-DA prediction for EAC samples from the NMR model comparing normal controls and high-risk (BE+HGD) patients.

Figure 13G:
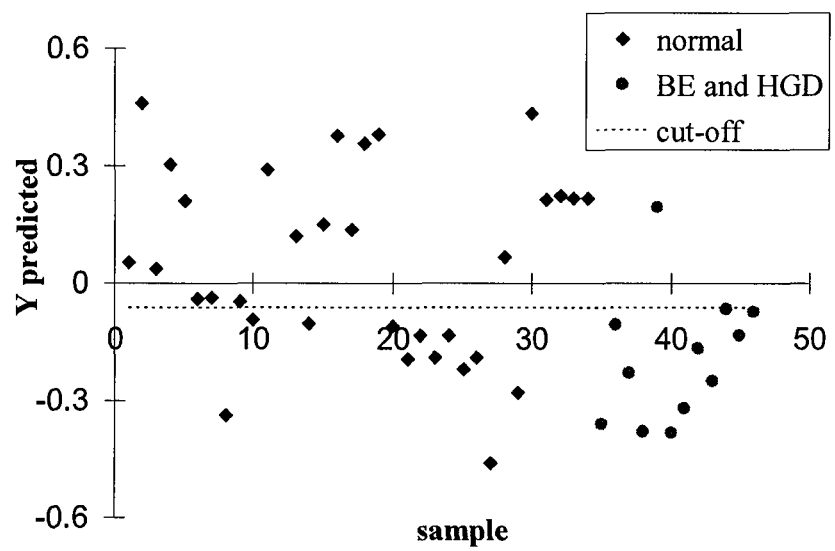
Figure 13H:
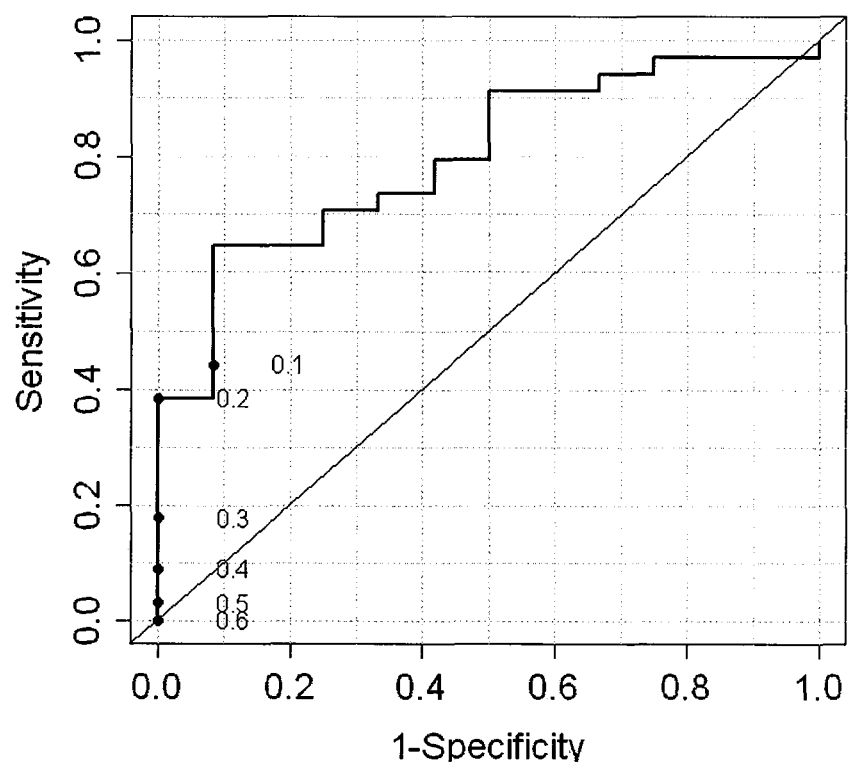
Figure 13I:
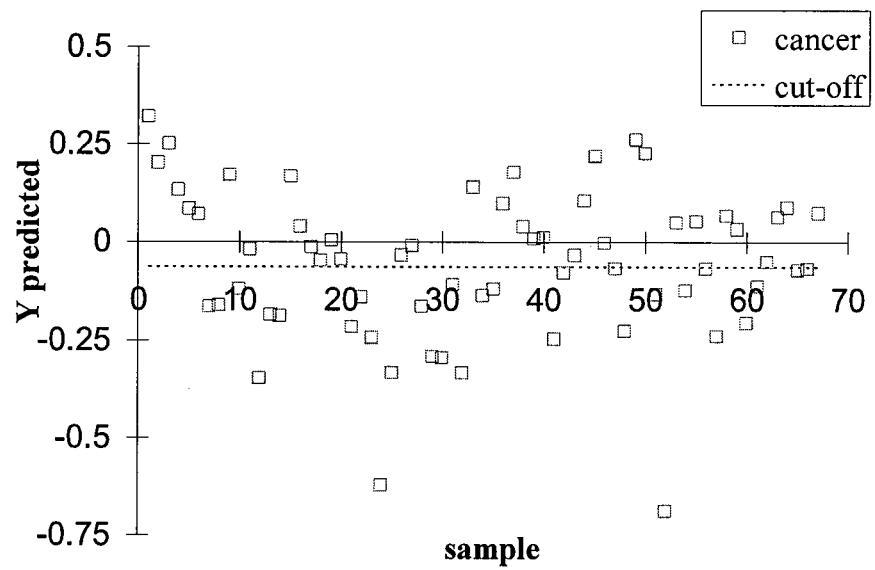

FIG. 13G shows the results of the PLS-DA model using the combination of the five LC-MS and NMR detected metabolite markers; FIG. 13H shows the ROC curve using the cross-validated predicted class values (AUROC=0.80); FIG. 13I shows the PLS-DA prediction for EAC samples from the LC-MS AND NMR model comparing normal controls and high-risk (BE+HGD) patients.

As summarized above, Table 11 lists 26 measured compounds that the present studies have found to differ in concentration at the p<0.05 level for the three comparisons, Control vs. EAC, EAC vs. High-risk (BE+HGD), and Control vs. High-risk (BE+HGD). The compounds are lactic acid, valine, leucine, methionine, carnitine, tyrosine, tryptophan, 5-hydroxytryptophan, myristic acid, margaric acid, linolenic acid, linoleic acid, pyroglutamic acid, glutamine, β-hydroxybutyrate, citrate, unknown compound 1 appearing at 2.63 ppm, lysine, creatinine, α-glucose, N-acetylated protein, proline, histidine, alanine, glutamate, and unknown compound 2 appearing at 2.91 ppm. Panels of metabolic biomarkers at the p<0.05 level range in size from 5 metabolic biomarkers for the Control vs. High-risk (BE+HGD) comparison (three of which have been identified to date: lactic acid, proline and pyroglutamic acid) to 18 identified metabolic biomarkers for the Control vs. EAC comparison. The set of chemically identified metabolic biomarkers at the p<0.05 level for at least one of the three comparisons is lactic acid, valine, leucine, methionine, carnitine, tyrosine, tryptophan, 5-hydroxytryptophan, myristic acid, margaric acid, linolenic acid, linoleic acid, pyroglutamic acid, glutamine, β-hydroxybutyrate, citrate, lysine, creatinine, α-glucose, proline, histidine, alanine, and glutamate.

Table 13 summarizes the metabolic biomarkers that have been shown in ten comparisons Example 1 and Example 2 above to be useful in distinguishing at the p<0.05 level the conditions in comparisons across the indicated transitions. Panels of identified compounds that have concentration changes that have been found to be useful in characterizing the indicated transitions and states in the progression from normal tissue to EAC are:

Normal control vs. EAC (Table 4, Table 5) glutamine, β-hydroxybutyrate, citrate, lysine, creatinine, lactate, and α-glucose.

Normal control vs. EAC (Table 11) glutamine, β-hydroxybutyrate, citrate, unknown 1, creatinine, lactate, α-glucose, leucine, valine, methionine, carnitine, tyrosine, tryptophan, 5-hydroxytryptophan, myristic acid, margaric acid, linolenic acid, and linoleic acid.

Control vs. HGD (Table 5,) β-hydroxybutyrate, citrate, creatinine, lactate, and α-glucose.

Control vs. High-risk (BE+HGD) (Table 11) lactate, pyroglutamic acid, N-acetylated protein, and proline.

EAC vs. High-risk (BE+HGD) (Table 11) lysine, lactate, leucine, valine, methionine, tyrosine, myristic acid, linolenic acid, pyroglutamic acid, N-acetylated protein, proline, histidine, alanine, and glutamate.

BE vs. EAC (Table 5,) glutamine, and β-hydroxybutyrate.

Control vs. early stage EAC (Table 8, p<0.05) glutamine, β-hydroxybutyrate, citrate, lysine, creatinine, lactate, α-glucose leucine, acetone, acetoacetate, and asparagine, Control vs late stage EAC (Table 8) glutamine, β-hydroxybutyrate, citrate, lysine, creatinine, lactate, α-glucose, acetoacetate, and asparagine.

BE vs. early stage EAC (Table 8) glutamine, lysine creatinine acetone, acetoacetate, and asparagine.

HGD vs. early stage EAC (Table 8) Lysine and glutamine.

TABLE 13

Differentiating Metabolite Biomarkers (p <0.05)

| Comparison | C vs. EAC | C vs. HGD | C vs. High-risk | EAC vs. High-risk | EAC vs. BE | C vs. Early EAC | C vs. Late EAC | BE vs. Early EAC | HGD vs. Early EAC | Early EAC vs. Late EAC |
|---|---|---|---|---|---|---|---|---|---|---|
| See Table | 4, 5, 11 | 5 | 11 | 11 | 5 | 8 | 8 | 8 | 8 | 8 |

Amino Acids & Amino Acid Metabolites

| | | | | | | | | | | |
|---|---|---|---|---|---|---|---|---|---|---|
| glutamine | ▓ | | | | | ▓ | ▓ | | | |
| asparagine | | | | | | ▓ | ▓ | | | |
| proline | | | ▓ | ▓ | | | | | | |
| histidine | | | | ▓ | | | | | | |
| alanine | | | | ▓ | | | | | | |
| glutamate | | | | ▓ | | | | | | |
| valine | ▓ | | | ▓ | | | | | | |
| leucine | ▓ | | | ▓ | | | | ▓ | | |
| methionine | ▓ | | | ▓ | | | | | | |
| lysine | ▓ | | | ▓ | | | | ▓ | | |
| tyrosine | ▓ | | | ▓ | | | | | | |
| tryptophan | ▓ | | | | | | | | | |
| creatinine | ▓ | ▓ | | | | | | ▓ | | |
| carnitine | ▓ | | | | | | | | | |
| 5-hydroxytryptophan | ▓ | | | | | | | | | |
| pyroglutamic acid | | | ▓ | ▓ | | | | | | |

TABLE 13-continued

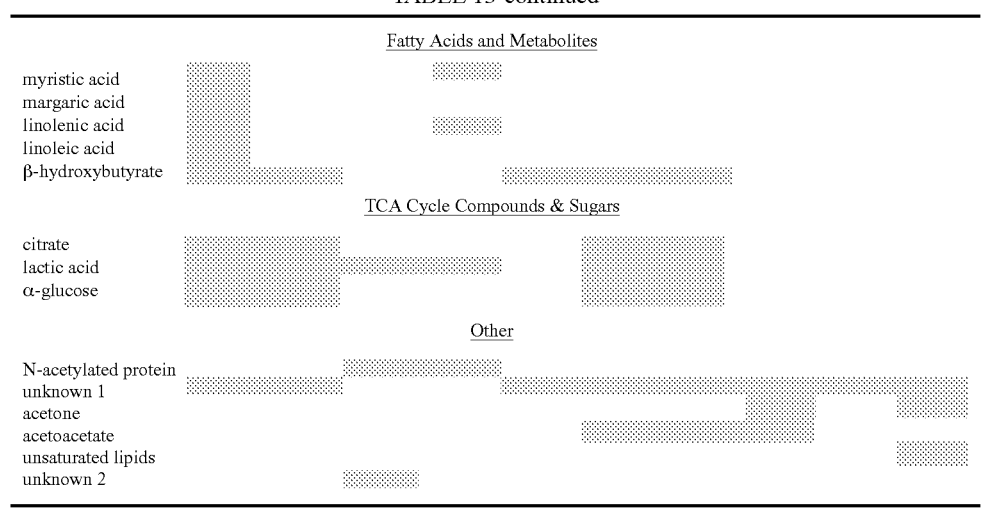

Comparison of the individual metabolites and the statistical models developed using the differentiating metabolites in the three groups showed that metabolic profiles of the high-risk (BE+HGD) patients were different from both EAC patients and normal controls. Progressive changes in the levels of twelve metabolites derived from LC-MS and NMR methods indicate the potential utility for identifying high-risk (BE+HGD) patients who may develop EAC (FIG. 10A-FIG. 10L). This is particularly important since BE and HGD are major risk factors for the development of EAC. Identification of metabolites in these patients, which are potentially predictive of the development of EAC is particularly important for the management of at risk patients.

Identification of metabolic pathways associated with altered metabolites can improve the understanding of the biology and pathology in the trajectory from normal to esophageal disease and ultimately EAC. FIG. 6 shows a detailed metabolic pathway map associated with changes concentration of the metabolite markers identified using either MS, NMR, or both MS and NMR methods. Altered pathways include changes in amino acid metabolism, biosynthesis and degradation (glutamine, lysine, carnitine, valine, leucine, methionine, tryptophan, 5-hydroxytryptophan, and tyrosine), glycolysis (lactate and α-glucose), ketone bodies synthesis and degradation (β-hydroxybutyrate), tricarboxylic acid (TCA) cycle (citric acid cycle) and fatty acid metabolism (linoleic acid, linolenic acid and myristic acid).

Energy metabolism and the TCA cycle dominate the altered biochemistry of EAC. Accumulation of lactate, which is common in many cancers (Walenta, S., et al. High Lactate Levels Predict Likelihood of Metastases, Tumor Recurrence, and Restricted Patient Survival in Human Cervical Cancers, Cancer Res, 2000, 60:916-921), mirrors the demand for higher energy in tumor malignancy. The increase of carnitine in the EAC patients indicates increased activity of carnitine, lysine and glutamine biosynthesis connected with the TCA cycle via lactate accumulation, again in response to the higher energy demand of the tumor. Many serum amino acids, including valine, leucine, tyrosine, methionine, tryptophan and 5-hydroxytryptophan, were down-regulated in EAC patients compared with normal controls, which indicates an increased demand for and over-utilization of amino acids in the tumor tissue, as further evidenced by other reports on the cancer as welt as other malignant tumors. Fatty acid metabolism is also altered in the cancer patient sera, as seen by the reduced levels of a number of fatty acids, and which is also in accordance with findings in serum from other cancers such as colorectal cancer.

We also noticed that valine and tyrosine were decreased in the sera of patients in the current study, but increased in the tissue of EAC patients. The differential regulation of certain metabolites in biofluids versus tissue samples for the same disease has been reported in other disease metabolic profiling studies as well. For example, while histidine has been reported to be increased in colorectal cancer patient tissue, it has been reported to be depleted in urine.

The results of the present study have shown that the metabolic profiling of serum using a combination of and $^1$H NMR, along with multivariate statistical methods can provide a detailed picture of metabolic changes in EAC and patients with high cancer risk (BE+HGD), compared with normal controls. These patient groups can be distinguished from one another with good accuracy. Since these two analytical methods largely detect different metabolites, their combined use for global metabolic profiling is advantageous. Progressive changes in a number of metabolites between the three groups are particularly noteworthy since these metabolites, which vary gradually from normal controls to high-risk (BE+HGD) patients and EAC patients can be useful biomarkers for the early detection of EAC.

Technical and scientific terms used herein have the same meaning as is commonly understood by one of skill in the art to which this disclosure belongs. It should be noted that the terms "first," "second," and the like herein do not denote any order or importance, but rather are used to distinguish one element from another. The terms "a" and "an" herein do not denote a limitation of quantity, but rather denote the presence of at least one of the referenced items. The terms "bottom" and "top" are used herein, unless otherwise noted, merely for convenience of description, and are not limited to anyone position or spatial orientation. In addition, the modifier "about" used in connection with a quantity is inclusive of the stated value and has the meaning dictated by the context (e.g., includes the degree of error associated with measurement of the particular quantity). Unless otherwise noted, the ends of a range are included in the range of values, e.g. "integers from 3 to 7" includes the values 3, 4, 5, 6, and 7.

While the disclosure has been described with reference to an exemplary embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

What is claimed is:

1. A method of determining a stage in the progression of an esophageal adenocarcinoma in a subject, comprising the steps of:
    measuring the concentrations of the at least two components of a panel of a plurality of metabolic biomarkers consisting of lysine, lactate, leucine, valine, methionine, tyrosine, myristic acid, margaric acid, linolenic acid, pyroglutamic acid, proline, histidine, alanine and glutamate in a test sample of a biofluid from the subject to be tested for a stage in the progression of an esophageal adenocarcinoma, wherein the components of the panel have been selected from a population of metabolic biomarkers that have been shown to significantly distinguish a first stage from a second stage in the progression of an esophageal adenocarcinoma; and
    wherein a statistical model has been constructed using the combined measured concentration differences of each component in the panel of a plurality of biomarkers in a first sample from a subject in the first stage and the measured concentration of each component of the panel of a plurality of biomarkers in a second sample from a subject in the second stage, wherein the statistical model distinguishes the first sample from the second sample;
    using the statistical model to determine the relationship of the concentrations of the components of the panel of metabolic biomarkers measured in the test sample to the concentrations of the components of the panel of metabolic biomarkers that are characteristic of the first stage and characteristic of the second stage;
    thereby determining the stage in the progression of the esophageal adenocarcinoma in a subject.

2. The method of claim 1 wherein the step of measuring the concentrations further includes measuring the concentration of at least two components of a panel of a plurality of metabolic biomarkers in a sample of a biofluid from a control source, wherein the metabolic biomarker is a component of a panel of a plurality of biomarkers; and
    wherein the statistical model is a partial least squares model.

3. The method of claim 1 wherein the stages in the progression of esophageal adenocarcinoma being determined are:
    a. the first stage is normal and the second stage is esophageal adenocarcinoma, or
    b. the first stage is normal and the second stage is high grade dysplasia, or
    c. the first stage is normal and the second stage is high risk (Barrett's esophagus or high grade dysplasia), or
    d. the first stage is high risk (Barrett's esophagus or high grade dysplasia) and the second stage is esophageal adenocarcinoma, or
    e. the first stage is Barrett's esophagus and the second stage is esophageal adenocarcinoma, or
    f. the first stage is normal and the second stage is late stage esophageal adenocarcinoma, or
    g. the first stage is normal and the second stage is early stage esophageal adenocarcinoma, or
    h. the first stage is Barrett's esophagus and the second stage is early stage esophageal adenocarcinoma, or
    i. the first stage is high grade dysplasia and the second stage is early stage esophageal adenocarcinoma.

4. The method of claim 1 wherein the panel comprises biomarkers that have been identified by a plurality of methods selected from nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis mass spectrometry.

5. The method of claim 4 wherein the panel comprises biomarkers that have been identified by the combination of techniques of nuclear magnetic resonance (NMR) spectrometry and liquid chromatography-mass spectrometry (LC-MS).

* * * * *